United States Patent [19]
Terasawa et al.

[11] Patent Number: 5,767,296
[45] Date of Patent: Jun. 16, 1998

[54] DEACETOXYTAXOL DERIVATIVES

[75] Inventors: Hirofumi Terasawa; Tsunehiko Soga; Kiyoshi Nakayama, all of Tokyo, Japan

[73] Assignee: Daiichi Pharmaceutical Co., Ltd., Tokyo, Japan

[21] Appl. No.: 750,374

[22] PCT Filed: Jun. 9, 1995

[86] PCT No.: PCT/JP95/01163

§ 371 Date: Dec. 6, 1996

§ 102(e) Date: Dec. 6, 1996

[87] PCT Pub. No.: WO95/33740

PCT Pub. Date: Dec. 14, 1995

[30] Foreign Application Priority Data

Jun. 9, 1994 [JP] Japan ................................. 6-127334
Feb. 20, 1995 [JP] Japan ................................. 7-030949

[51] Int. Cl.[6] ............................................. C07D 305/14
[52] U.S. Cl. ............................................. 549/510; 549/511
[58] Field of Search ................................. 549/510, 511

[56] References Cited

FOREIGN PATENT DOCUMENTS 3-505725  12/1991  Japan .......................... C07D 305/14
7-502981  3/1995   Japan .......................... C07D 305/14

*Primary Examiner*—Ba K. Trinh
*Attorney, Agent, or Firm*—Sughrue, Mion, Zinn, Macpeak & Seas, PLLC

[57] ABSTRACT

A novel taxol derivative having the formula (I), in which the 10-position is modified to have a carbon-carbon bond, is disclosed. The taxol derivative of the present invention has an antitumor activity.

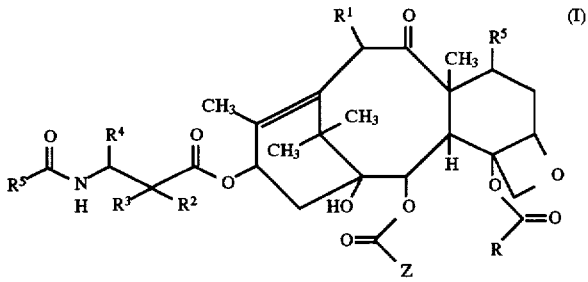

22 Claims, No Drawings

DEACETOXYTAXOL DERIVATIVES

This is a 371 application of PCT/JP95/01163 filed on Jun. 9, 1995.

TECHNICAL FIELD

The present invention relates to novel taxol derivatives having an antitumor activity.

BACKGROUND ART

Taxol is a natural substance represented by the following chemical formula (i) and is obtainable in a small quantity from the bark of the Pacific yew tree, *Taxus breviofolia*, Taxaceae.

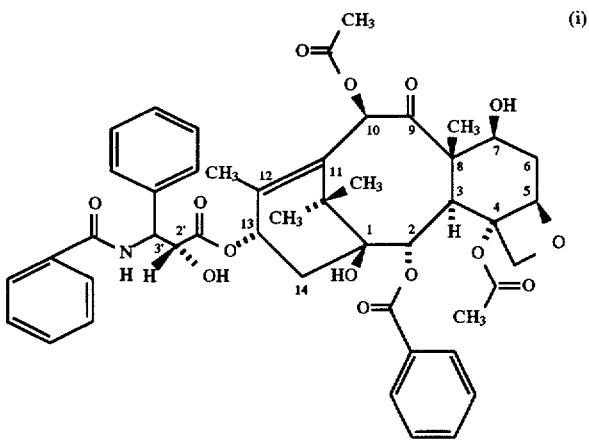

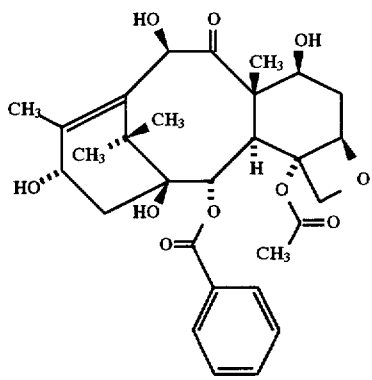

In particular, an attention has been drawn to Taxotere® having the following formula (iii) in view of its antitumor activity which is equal to or higher than that of taxol, and at present development of Taxotere® as an antitumor agent is in progress.

Taxol has been known to have an antitumor activity, and the unique mechanism of its action is based on an inhibitory activity on the disassembly of microtubules in cytokinesis. Thus, clinical application of taxol is expected as a new type of antitumor agent different from conventional antitumor agents.

Hitherto, only a very small quantity of taxol has been obtained from a natural source. However, in recent years, semi-synthesized taxol derivatives using, as a starting material, 10-O-deacetylbaccatin III represented by the following formula (ii) as a taxol precursor which is obtained relatively in a large quantity from needles of the Pacific yew tree have been reported (JP-A-03-505725). (The term "JP-A" as used herein means an unexamined published Japanese patent application.)

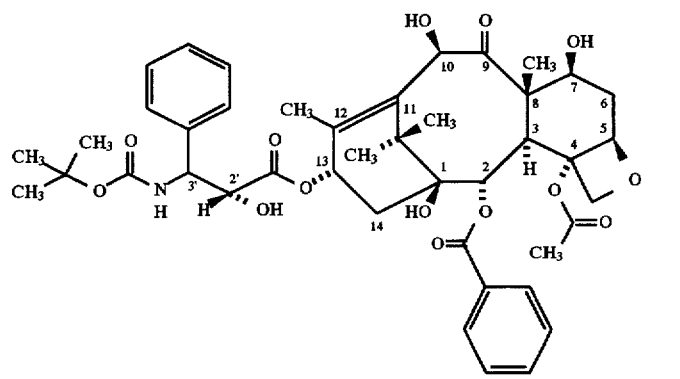

However, although taxol or derivatives represented by the above formula (iii), are potent as antitumor agents, it has been revealed that their effectiveness on cancers of digestive tracts, in particular, the cancer of large intestine, is weak, and hence derivatives having a strong antitumor activity have been desired.

DISCLOSURE OF INVENTION

Hitherto, taxol derivatives substituted at the 10-position with an acetoxy group or a hydroxy group, and those in which the hydroxy group is further substituted with an acyl group have been reported. Also an alkylaminocarbonyloxy group have been reported (EP-A-524093). Further, derivatives having only hydrogen atoms at the 10-position are also known (*Tetrahedron Lett.*, 34, 4921 (1993)). As a result of extensive studies, the present inventors found that taxol derivatives in which an alkyl group has been introduced into the 10-position thereof exhibit a strong antitumor activity and completed the present invention.

The present invention relates to a compound represented by the general formula (I)

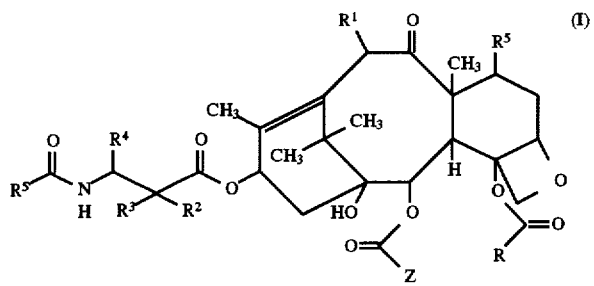

wherein $R^1$ represents an alkyl group, an alkenyl group or an alkynyl group (wherein these alkyl, alkenyl and alkynyl groups may have one or more substituents selected from the group consisting of a carboxyl group, an alkoxyl group, an aryloxy group, an alkoxycarbonyl group, an aryloxycarbonyl group, a cyano group, a hydroxy group, an amino group, an alkylamino group, an acyl group, an acylamino group, an acyloxy group, an alkoxycarbonylamino group, an alkylthio group, an alkylsulfinyl group, an alkylsulfonyl group and a 3- to 8-membered nitrogen containing saturated or unsaturated heterocyclic substituent (in which the heterocyclic substituent may have one or more alkyl groups on the carbon atom which is a constituent atom of the ring) represented by the formula:

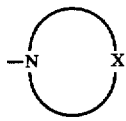

(wherein X represents an oxygen atom, a sulfur atom, $CH_2CH$—Y, NH or N—Y wherein Y represents an alkyl group);

$R^2$ represents a hydrogen atom, a hydroxy group, a halogen atom or an alkyl group;

$R^3$ represents a hydrogen atom, a hydroxy group, a halogen atom or an alkyl group;

$R^4$ represents an alkyl group, an alkenyl group, an alkynyl group, a cycloalkyl group, an aryl group or a heterocyclic group (wherein these alkyl, alkenyl, alkynyl, cycloalkyl, aryl and heterocyclic groups may have one or more substituent selected from the group consisting of a halogen atom, a hydroxy group, a carboxyl group, an alkyl group, an alkoxyl group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group);

$R^5$ represents an alkyl group, an aryl group or an alkoxyl group (wherein these alkyl, aryl and alkoxyl groups may have, one or more substituents selected from the group consisting of a halogen atom, a hydroxy group, a carboxyl group, an alkyl group, an alkoxyl group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group);

$R^6$ represents a hydrogen atom or a hydroxy group;

R represents an alkyl group, an alkyl group having a substituent, an alkenyl group, an alkenyl group having a substituent, an alkynyl group, an alkynyl group having a substituent, an alkoxyl group, an alkoxyl group having a substituent, a cycloalkyl group or a cycloalkyl group having a substituent (wherein the substituent of these alkyl, alkenyl, alkynyl, alkoxyl and cycloalkyl groups is selected from the group consisting of a halogen atom, a hydroxy group, a carboxyl group, an alkoxyl group, an aryloxy group, a phenyl group, an amino group, an alkylamino group, an alkoxycarbonyl group, an aryloxycarbonyl group, an acyl group, an acylamino group and an acyloxy group, and more than one substituents may be substituted); and Z represents a phenyl group (which may have more than one substituent selected from a group of a halogen atom, an alkyl group or an alkoxyl group), or a salt thereof.

The terms used in the present application are described hereinafter in detail.

The term "$C_1$–$C_6$" used herein means 1 to 6 carbon atoms, and, for example, "a $C_2$–$C_6$ alkenyl group" means an alkenyl group having from 2 to 6 carbon atoms.

The term "a halogen atom" represents a fluorine atom, a chlorine atom, a bromine atom or an iodine atom.

The term "an alkyl group" represents a straight chain or branched chain alkyl, for example, methyl, ethyl, propyl, isopropyl, butyl, isobutyl, tertiary butyl, pentyl, hexyl, octyl, decyl, dodecyl, tetradecyl, etc.

The term "an alkenyl group" represents a straight chain or branched chain alkenyl, for example, vinyl, allyl, isopropenyl, 2-methyl1-propenyl, etc.

The term "an alkynyl group" represents a straight chain or branched chain alkynyl, for example, ethynyl, 1-propynyl, 2-propynyl, 2-butynyl, 3-butynyl, 1-methyl-2-propynyl, 1,1-dimethyl-2-propynyl, 2-pentynyl, 2-hexynyl, etc.

The term "a cycloalkyl group" represents cyclopropyl, cyclobutyl, cyclopentyl, cyclohexyl, cycloheptyl, etc.

The term "an alkoxyl group" represents a group in which an alkyl group is bonded to an —O— group and includes, for example, methoxy, ethoxy, propoxy, isopropoxy, butoxy, isobutoxy, tertiary butoxy, pentyloxy, hexyloxy, etc. Also, it further includes a group in which a phenyl group (which may have a substituent) is bonded to an —O— group via an alkyl group such as benzyloxy, phenethyloxy and p-methoxybenzyloxy.

The term "an alkoxycarbonyl group" represents a group in which an alkyl group is bonded to the oxygen atom of the —COO— group, for example, methoxycarbonyl, ethoxycarbonyl, propoxycarbonyl, isopropoxycarbonyl, tertiary butoxycarbonyl, etc. Also, it further includes a group in which a phenyl group (which may have a substituent) is bonded to the oxygen atom of the —COO— group via an alkyl group such as benzyloxycarbonyl, phenethyloxycarbonyl and p-methoxybenzyloxycarbonyl.

The term "an aryl group" represents a monovalent group derived by removing a hydrogen atom from the nucleus of an aromatic hydrocarbon and includes phenyl, tolyl, biphenylyl, naphthyl, etc.

The term "an aryloxy group" represents a group in which an aryl group is bonded to an —O— group and includes phenoxy, naphthyloxy, etc.

The term "an aryloxycarbonyl group" represents a group in which an aryl group is bonded to the oxygen atom of the —COO— group and includes phenoxycarbonyl, naphthyloxycarbonyl, etc.

The term "an aminoalkyl group" represents a group in which an amino group is bonded to an alkyl group and includes aminomethyl, 2-aminoethyl, 1-aminoethyl, 3-aminopropyl, 4-aminobutyl, 5-aminopentyl, 6-aminohexyl, etc.

The term "an alkylamino group" represents a group in which one alkyl group is bonded to an amino group or two alkyl groups (which may be the same or different) are bonded to an amino group. Examples of the group in which one alkyl group is bonded to an amino group includes methylamino, ethylamino, propylamino, isopropylamino, hexylamino, etc., and examples of the group in which two alkyl groups are substituted on an amino group includes dimethylamino, diethylamino, ethylmethylamino, dihexylamino, etc.

The term "an alkylaminoalkyl group" represents a group in which an alkylamino group is bonded to an alkyl group and includes methylaminomethyl, 2-methylaminoethyl, dimethylaminomethyl, etc.

The term "an acyl group" represents a group in which a hydrogen, an alkyl group or an aryl group is bonded to a carbonyl group (—CO—) and includes formyl, acetyl, propanoyl, benzoyl, etc.

The term "an acylamino group" represents a group in which an acyl group is bonded to an amino group and includes acetamino, propanoylamino, benzoylamino, etc.

The term "an acyloxy group" represents a group in which a hydrogen atom, an alkyl group or an aryl group is bonded to the carbon atom of the —COO— group and includes acetoxy, propanoyloxy, benzoyloxy, etc.

The term "an alkoxycarbonylamino group" represents a group in which an alkyl group is bonded to the oxygen atom of the —OCONH— group and includes methoxycarbonylamino, ethoxycarbonylamino, tertiary butoxycarbonylamino, etc. Also, it further includes a group in which a phenyl group (which may have a substituent) is bonded to an alkyl group, for example, benzyloxycarbonylamino.

The term "an alkylthio group" represents a group in which an alkyl group is bonded to the —S— group and includes methylthio, ethylthio, propylthio, butylthio, hexylthio, etc.

The term "an alkylsulfinyl group" represents a group in which an alkyl group is bonded to the sulfur atom of the group:

and includes methylsulfinyl, ethylsulfinyl, propylsulfinyl, butylsulfinyl, hexylsulfinyl, etc.

The term "an alkylsulfonyl group" represents a group in which an alkyl group is bonded to the sulfur atom of the group:

and includes methylsulfonyl, ethylsulfonyl, propylsulfonyl, butylsulfonyl, hexylsulfonyl, etc.

The term "a heterocyclic group" represents a group derived from a monocyclic or bicyclic saturated or unsaturated heterocyclic compound containing one or more hetero atoms selected from the group consisting of an oxygen atom, a nitrogen atom and a sulfur atom as a constituent atom of the ring structure. Examples of the monocyclic heterocyclic group include a group derived from monocyclic heterocyclic compounds such as pyrrole, furan, thiophene, pyrrolidine, tetrahydrofuran, tetrahydrothiophene, imidazole, pyrazole, imidazolidine, pyrazolidine, oxazole, thiazole, oxadiazole, thiadiazole, pyridine, dihydropyridine, tetrahydropyran, piperidine, pyridazine, pyrimidine, pyrazine, piperazine, dioxane, pyran, morpholine, etc., and examples of the bicyclic heterocyclic group include a group derived from bicyclic heterocyclic compounds such as benzofuran, indolidine, benzothiophene, indole, naphthylidine, quinoxaline, quinazoline, chroman, etc. These heterocyclic groups may be bonded to any positions.

The term "a saturated or unsaturated 3- to 8-membered heterocyclic group containing a nitrogen atom represented by the formula:

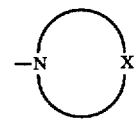

wherein X represents an oxygen atom, a sulfur atom, $CH_2$, CH—Y, NH or N—Y (wherein Y represents an alkyl group)" represents those derived from saturated or unsaturated 3- to 8-membered heterocyclic compounds containing at least one nitrogen atom as constituent atom of the ring, for example, pyrrolidine, imidazolidine, pyrazolidine, oxazolidine, thiazolidine, isoxazolidine, isothiazolidine, piperidine, piperazine, morpholine, thiomorpholine and pyridine.

Next, each of the substituents in the formula (I) is described.

$R^1$ is an alkyl group, an alkenyl group or an alkynyl group, and these alkyl, alkenyl and alkynyl groups may have one or more substituents selected from the group consisting of a carboxyl group, an alkoxyl group, an aryloxy group, an alkoxycarbonyl group, an aryloxycarbonyl group, a cyano group, a hydroxy group, an amino group, an alkylamino group, an acyl group, an acylamino group, an acyloxy group, an alkoxycarbonylamino group, an alkylthio group, an alkylsulfinyl group, an alkylsulfonyl group and a saturated or unsaturated 3- to 8-membered heterocyclic substituent containing a nitrogen atom represented by the formula:

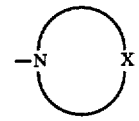

wherein X represents an oxygen atom, a sulfur atom, $CH_2$, CH—Y, NH or N—Y (wherein Y represents an alkyl group), and the heterocyclic group may have one or more alkyl groups on the carbon atom which is a constituent atom of the ring.

The alkyl group as $R^1$ is preferably a $C_1$–$C_{14}$ alkyl group.

Similarly, the alkenyl group as $R^1$ is preferably a $C_2$–$C_6$ alkenyl group.

Similarly, the alkynyl group as $R^1$ is preferably a $C_2$–$C_6$ alkynyl group.

The substituents on the alkyl group, the alkenyl group or the alkynyl group as $R^1$ are described below.

The substituents may be bonded to any positions of the alkyl, alkenyl and alkynyl groups.

The alkoxyl group as a substituent for the alkyl group, the alkenyl group or the alkynyl group in $R^1$ is preferably a $C_1$–$C_6$ alkoxyl group.

Similarly, the aryloxy group is preferably a phenyloxy group.

Similarly, the alkoxycarbonyl group is a $C_2$–$C_7$ alkoxycarbonyl group in which a $C_1$–$C_6$ alkyl group is bonded to the oxygen atom of a —COO— group, and includes methoxycarbonyl, ethoxycarbonyl, propoxycarbonyl, isopropoxycarbonyl, tertiary butoxycarbonyl, etc.

Similarly, the aryloxycarbonyl group is preferably a phenyloxycarbonyl group.

Similarly, the alkylamino group is a group in which one $C_1$-$C_6$ alkyl group is bonded to an amino group or two $C_1$-$C_6$ alkyl groups (which may be the same or different) are bonded to an amino group. Preferred examples of the group in which one $C_1$-$C_6$ alkyl group is bonded to an amino group include methylamino, ethylamino, propylamino, isopropylamino, hexylamino, etc., and preferred examples of the group in which two $C_1$-$C_6$ alkyl groups are bonded to an amino group include dimethylamino, diethylamino, ethylmethylamino, dihexylamino, etc.

Similarly, the acyl group is a group in which a hydrogen, a $C_1$-$C_6$ alkyl group or an aryl group is bonded to a carbonyl group (—CO—), and includes formyl, acetyl, propanoyl, benzoyl, etc.

Similarly, the acylamino group is a group in which the above-described acyl group is bonded to an amino group, and preferred examples thereof includes acetamino, propanoylamino, benzoylamino, etc.

Similarly, the acyloxy group is a group in which a hydrogen atom, a $C_1$-$C_6$ alkyl group or an aryl group is bonded to the carbon atom of a —COO— group, and includes acetoxy, propanoyloxy, benzoyloxy, etc.

Similarly, the alkoxycarbonylamino group is a group in which a $C_1$-$C_6$ alkyl group is bonded to the oxygen atom of a —OCONH— group, and includes methoxycarbonylamino, ethoxycarbonylamino, tertiary butoxycarbonylamino, etc. Also, it further includes a group in which a phenyl group (which may have a substituent) is bonded to the oxygen atom of the —OCONH— group via an alkyl group such as benzyloxycarbonylamino.

Similarly, the alkylthio group is preferably a $C_1$-$C_6$ alkylthio group such as methylthio, ethylthio, propylthio, butylthio, and hexylthio.

Similarly, the alkylsulfinyl group is preferably a $C_1$-$C_6$ alkylsulfinyl group such as methylsulfinyl, ethylsulfinyl, propylsulfinyl, butylsulfinyl and hexylsulfinyl.

Similarly, the alkylsulfonyl group is preferably a $C_1$-$C_6$ alkylsulfonyl group such as methylsulfonyl, ethylsulfonyl, propylsulfonyl, butylsulfonyl and hexylsulfonyl.

Similarly, preferred examples of the saturated or unsaturated 3- to 8-membered heterocyclic group containing a nitrogen atom (which may have one or more alkyl groups on the carbon atom which is a constituent atom of the ring) represented by the formula:

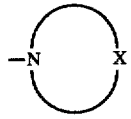

wherein X represents an oxygen atom, a sulfur atom, $CH_2$, NH or N—Y (wherein Y represents an alkyl group) include those derived from heterocyclic compounds such as pyrrolidine, imidazolidine, pyrazolidine, piperidine, piperazine, morpholine, thiomorpholine and 4-$C_1$-$C_3$ alkylpiperazine.

Preferred examples of alkyl groups bonded to the carbon atom which is a constituent atom of the heterocyclic ring include a methyl group, an ethyl group and a propyl group.

Y is preferably a $C_1$-$C_3$ alkyl group.

$R^2$ and $R^3$ each represents a hydrogen atom, a hydroxy group, a halogen atom or an alkyl group.

Preferred examples of the halogen atom for $R^2$ and $R^3$ include a fluorine atom, a chlorine atom and a bromine atom.

Similarly, preferred examples of the alkyl group for $R^2$ and $R^3$ include a methyl group, an ethyl group and a propyl group.

$R^4$ represents an alkyl group, an alkenyl group, an alkynyl group, a cycloalkyl group, an aryl group or a heterocyclic group (wherein these alkyl, alkenyl, alkynyl, cycloalkyl, aryl and heterocyclic groups may have one or more substituents selected from the group consisting of a halogen atom, a hydroxy group, a carboxyl group, an alkyl group, an alkoxyl group, a phenyl group, an amino group, an alkylamino group, an aminoalkyl group, an alkylaminoalkyl group, alkoxycarbonyl group, an aryloxycarbonyl group, an acyl group, an acylamino group and an acyloxy group).

The alkyl group as $R^4$ is preferably a $C_1$-$C_8$ alkyl group.

Similarly, the alkenyl group as $R^4$ is preferably a $C_2$-$C_6$ alkenyl group.

Similarly, the alkynyl group as $R^4$ is preferably a $C_2$-$C_6$ alkynyl group.

Similarly, the cycloalkyl group as $R^4$ is preferably a $C_3$-$C_7$ cycloalkyl group.

Similarly, the aryl group as $R^4$ is preferably a phenyl group.

Similarly, the heterocyclic group as $R^4$ is preferably a group derived from the monocyclic 4- to 9-membered heterocyclic compounds such as pyrrole, furan, thiophene, pyrrolidine, tetrahydrofuran, tetrahydrothiophene, imidazole, pyrazole, imidazolidine, pyrazolidine, oxazole, thiazole, oxadiazole, thiadiazole, pyridine, dihydropyridine, tetrahydropyran, piperidine, pyridazine, pyrimidine, pyrazine, dioxane, pyran, morpholine, etc., and preferably a group derived from the bicyclic heterocyclic compounds such as benzofuran, indolidine, benzothiophene, indole, naphthylidine, quinoxaline, quinazoline, chroman, etc.

The substituents on the alkyl group, the alkenyl group, the alkynyl group, the cycloalkyl group, the aryl group and the heterocyclic group as $R^4$ are described below.

The substituents may be bonded to any positions of the alkyl group, the alkenyl group, the alkynyl group, the cycloalkyl group, the aryl group or the heterocyclic group.

The alkyl group as a substituent on the cycloalkyl group, the aryl group or the heterocyclic group as $R^4$ is preferably a $C_1$-$C_6$ alkyl group.

The alkoxyl group as a substituent on the alkyl group, the alkenyl group, the alkynyl group, the cyclcoalkyl group, the aryl group or the heterocyclic group as $R^4$ is preferably a $C_1$-$C_6$ alkoxyl group.

Similarly, the alkylamino group is a group in which one $C_1$-$C_6$ alkyl group is bonded to an amino group or two $C_1$-$C_6$ alkyl groups (which may be the same or different) are bonded to an amino group. Preferred examples of the group in which one $C_1$-$C_6$ alkyl group is bonded to an amino group include methylamino, ethylamino, propylamino, isopropylamino, hexylamino, etc., and preferred examples of the group in which two $C_1$-$C_6$ alkyl groups are bonded to an amino group include dimethylamino, diethylamino, ethylmethylamino, dihexylamino, etc.

Similarly, the aminoalkyl group is preferably an amino $C_1$-$C_6$ alkyl group such as aminomethyl, 2-aminoethyl, 1-aminoethyl, 3-aminopropyl, 4-aminobutyl, 5-aminopentyl and 6-aminohexyl.

Similarly, the alkylaminoalkyl group is preferably a group, in which a $C_1$-$C_6$ alkylamino group is bonded to a $C_1$-$C_6$ alkyl group, such as methylaminomethyl, 2-methylaminoethyl, dimethylaminomethyl, etc.

Similarly, the alkoxycarbonyl group is a $C_2$-$C_7$ alkoxycarbonyl group in which a $C_1$-$C_6$ alkyl group is bonded to the oxygen atom of a —COO— group, and includes methoxycarbonyl, ethoxycarbonyl, propoxycarbonyl, isopropoxycarbonyl, tertiary butoxycarbonyl, etc.

Similarly, the aryloxycarbonyl group is preferably a phenyloxycarbonyl group.

Similarly, the acyl group is a group in which a hydrogen, a $C_1-C_6$ alkyl group or an aryl group is bonded to a carbonyl group (—CO—), and includes formyl, acetyl, propanoyl, benzoyl, etc.

Similarly, the acylamino group is a group in which the above-described acyl group is bonded to an amino group, and includes acetamino, propanoylamino, benzoylamino, etc.

Similarly, the acyloxy group is a group in which a hydrogen atom, a $C_1-C_6$ alkyl group or an aryl group is bonded to the carbon atom of a —COO— group, and includes acetoxy, propanoyloxy, benzoyloxy, etc.

$R^5$ represents an alkyl group, an aryl group or an alkoxyl group (wherein these alkyl, aryl and alkoxyl groups may have one or more substituents selected from the group consisting of a halogen atom, a hydroxy group, a carboxyl group, an alkyl group, an alkoxyl group, a phenyl group, an amino group, an alkylamino group, an aminoalkyl group, an alkylaminoalkyl group, alkoxycarbonyl group, an aryloxycarbonyl group, an acyl group, an acylamino group and an acyloxy group).

The alkyl group $R^5$ is a $C_1-C_8$ alkyl group.

Similarly, the aryl group as $R^5$ is preferably a phenyl group.

The alkoxyl group as $R^5$ is preferably a $C_1-C_8$ alkoxyl group.

The substituents on the alkyl group, the aryl group or the alkoxyl group as $R^5$ are described below.

The substituents may be bonded to any positions of the alkyl group, the aryl group or the alkoxyl group.

The alkyl group as a substituent on the aryl group as $R^5$ is preferably a $C_1-C_6$ alkyl group.

The alkoxyl group as a substituent on the alkyl group, the aryl group or the alkoxyl group as $R^5$ is preferably a $C_1-C_6$ alkoxyl group.

Similarly, the alkylamino group is a group in which one $C_1-C_6$ alkyl group is bonded to an amino group or two $C_1-C_6$ alkyl groups (which may be the same or different) are bonded to an amino group. Preferred examples of the group in which one $C_1-C_6$ alkyl group is bonded to an amino group include methylamino, ethylamino, propylamino, isopropylamino, hexylamino, etc., and preferred examples of the group in which two $C_1-C_6$ alkyl groups are bonded to an amino group include dimethylamino, diethylamino, ethylmethylamino, dihexylamino, etc.

Similarly, the aminoalkyl group is preferably a group, in which an amino is bonded to a $C_1-C_6$ alkyl group, such as aminomethyl, 2-aminoethyl, 1-aminoethyl, 3-aminopropyl, 4-aminobutyl, 5-aminopentyl, 6-aminohexyl, etc.

Similarly, the alkylaminoalkyl group is preferably a group, in which a $C_1-C_6$ alkylamino group is bonded to a $C_1-C_6$ alkyl group, such as methylaminomethyl, 2-methylaminoethyl, dimethylaminomethyl, etc.

Similarly, the alkoxycarbonyl group is a $C_2-C_7$ alkoxycarbonyl group in which a $C_1-C_6$ alkyl group is bonded to the oxygen atom of a —COO— group, and includes methoxycarbonyl, ethoxycarbonyl, propoxycarbonyl, isopropoxycarbonyl, tertiary butoxycarbonyl, etc.

Similarly, the aryloxycarbonyl group is preferably a phenyloxycarbonyl group.

Similarly, the acyl group is a group in which a hydrogen, a $C_1-C_6$ alkyl group or an aryl group is bonded to a carbonyl group (—CO—), and includes formyl, acetyl, propanoyl, benzoyl, etc.

Similarly, the acylamino group is a group in which the above-described acyl group is bonded to an amino group, and includes acetamino, propanoylamino, benzoylamino, etc.

Similarly, the acyloxy group is a group in which a hydrogen atom, a $C_1-C_6$ alkyl group or an aryl group is bonded to the carbon atom of a —COO— group, and includes acetoxy, propanoyloxy, benzoyloxy, etc.

R is an alkyl group, an alkyl group having a substituent, an alkenyl group, an alkenyl group having a substituent, an alkynyl group, an alkynyl group having a substituent, an alkoxyl group, an alkoxyl group having a substituent, a cycloalkyl group or a cycloalkyl group having a substituent.

The alkyl group as R is preferably a $C_1-C_8$ alkyl group.

Similarly, the alkenyl group as R is preferably a $C_2-C_6$ alkenyl group.

Similarly, the alkynyl group as R is preferably a $C_2-C_6$ alkynyl group.

Similarly, the alkoxyl group as R is preferably a $C_1-C_6$ alkoxyl group, and a methoxy group and ethoxy group are particularly preferred.

Similarly, the cycloalkyl group as R is preferably a $C_3-C_6$ cycloalkyl group, and a cyclopropyl group and a cyclobutyl group are particularly preferred.

Also, the substituent on the alkyl group, the alkenyl group, an alkynyl group, the alkoxyl group or the cycloalkyl group is a group selected from the group consisting of a halogen atom, a hydroxy group, a carboxyl group, an alkoxyl group, an aryloxy group, a phenyl group, an amino group, an alkylamino group, an alkoxycarbonyl group, an aryloxycarbonyl group, an acyl group, an acylamino group and an acyloxy group, and the above-described group may have more than one substituent.

The substituents may be bonded at any positions of the alkyl group, the alkenyl group, the alkynyl group, or alkoxyl group or the cycloalkyl group.

Now, the substituents of the alkyl group, the alkenyl group, the alkynyl group, the alkoxyl group or the cycloalkyl group as R is described.

The alkoxyl group as a substituent of the alkyl group, the alkenyl group, the alkynyl group, the alkoxyl group or the cycloalkyl group as R is preferably a $C_1-C_6$ alkoxyl group.

Similarly, the aryloxy group is preferably a phenyloxy group.

Similarly, the alkylamino group is a group in which one $C_1-C_6$ alkyl group is bonded to the amino group or two $C_1-C_6$ alkyl groups are bonded to the amino group (wherein the two alkyl groups may be the same or different), and preferred examples of the amino group having one $C_1-C_6$ alkyl group are methylamino, ethylamino, propylamino, isopropylamino and hexylamino, and preferred examples of the amino group having two $C_1-C_6$ alkyl groups are dimethylamino, diethylamino, ethylmethylamino and dihexylamino.

Similarly, the alkoxycarbonyl group is a $C_2-C_7$ alkoxycarbonyl group in which a $C_1-C_6$ alkyl group is bonded to the oxygen atom of a —COO— group and includes methoxycarbonyl, ethoxycarbonyl, propoxycarbonyl, isopropoxycarbonyl, tertiary butoxycarbonyl, etc.

Similarly, the aryloxycarbonyl group is preferably a phenyloxycarbonyl group.

Similarly, the acyl group is a group in which a hydrogen atom, a $C_1-C_6$ alkyl group or an aryl group is bonded to a carbonyl group (a —CO— group), and includes formyl, acetyl, propanoyl, benzoyl, etc.

Similarly, "an acylamino group" is a group in which the above-described acyl group is bonded to an amino group and includes acetamino, propanoylamino, benzoylamino, etc.

Similarly, the acyloxy group is a group in which a hydrogen atom, a $C_1-C_6$ alkyl group or aryl group is bonded on the carbon atom of a —COO— group, and includes acetoxy, propanoyloxy, benzoyloxy, etc.

Z is a phenyl group, and the phenyl group may have more than one halogen atom, alkyl group or alkoxyl group as substituents.

The halogen atom as a substituent on the phenyl group as Z is preferably a fluorine atom and a chlorine atom.

Similarly, the alkyl group as a substituent is preferably a $C_1$–$C_3$ alkyl group.

Similarly, the alkoxyl group as a substituent is preferably a $C_1$–$C_3$ alkoxyl group.

The number of substituents on the phenyl group of Z is preferably 1 or 2, and the position of the substituent on the phenyl group is preferably a meta position of the connecting position of the phenyl group to the carbonyl group.

In the present invention, within the possible stereoisomers, those having a steric configuration represented by the following formula (iv) are preferred.

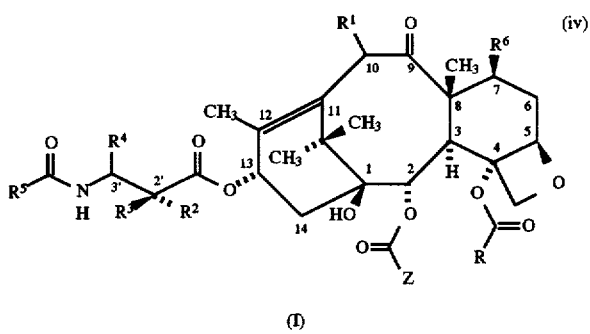

(I)

The steric configurations at the 10-position to which the substituent $R^1$ is bonded and at the 3'-position to which the substituent $R^4$ is bonded include both R and S configuration, however, regarding to the 3'-position, the same steric configuration as that of natural taxol is preferred.

The followings are preferred examples for each of the substituents in the compounds of the present invention.

Preferred groups for $R^1$ include an alkyl group or an alkenyl group (in which the alkyl group may have one or more substituents selected from the group consisting of a carboxyl group, an alkoxy group, an aryloxy group, an alkoxycarbonyl group, an aryloxycarbonyl group, a cyano group, a hydroxy group, an amino group, an alkylamino group, an acyl group, an acylamino group, an acyloxy group, an alkoxycarbonylamino group, an alkylthio group, an alkylsulfinyl group, an alkylsulfonyl group and a saturated or unsaturated 3- to 8-membered heterocyclic group containing a nitrogen atom represented by the formula:

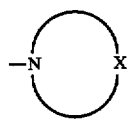

wherein X represents an oxygen atom, a sulfur atom, $CH_2$, CH—Y, NH or N—Y (wherein Y represents an alkyl group), and the heterocyclic group may have one or more alkyl groups on the carbon atom which is a constituent atom of the ring.

The alkyl group is preferably those having from 1 to 6 carbon atoms, and a methyl group, an ethyl group, a propyl group and a butyl group are particularly preferred.

The alkenyl group is preferably those having from 2 to 6 carbon atoms and an allyl group is particularly preferred.

Preferred substituents on this alkyl group include an alkoxycarbonyl group, a hydroxy group, a cyano group, an acyl group, an alkylamino group, an alkylthio group and a saturated 5- or 6-membered heterocyclic group containing a nitrogen atom represented by the formula:

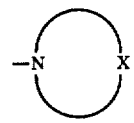

wherein X represents an oxygen atom, a sulfur atom, $CH_2$, CH—Y, NH or N—Y (wherein Y represents a $C_1$–$C_3$ alkyl group), and the heterocyclic group may have one or more alkyl groups on the carbon atom which is a constituent atom of the ring.

The most preferred substituents are a saturated 5- or 6-membered heterocyclic groups containing a nitrogen atom represented by the formula:

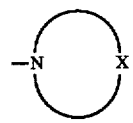

wherein X is as defined above; such as pyrrolidine, piperidine, piperazine, morpholine, thiomorpholine and a 4-$C_1$–$C_3$ alkylpiperazin-1-yl.

Further, the alkyl group substituted on the carbon atom which is a constituent atom of the ring of the heterocyclic group is preferably a methyl group.

The most preferred $R^1$ is an alkyl group having 2 or 3 carbon atoms and having, as a substituent, morpholine or thiomorpholine (in which morpholine or thiomorpholine may have one or more methyl groups on the carbon atom which is a constituent atom of the ring thereof), or an allyl group.

$R^2$ is preferably a halogen atom or a hydroxy group, and, of the halogen atoms, a fluorine atom is particularly preferred.

$R^3$ is preferably a halogen atom, a hydrogen atom or an alkyl group. Of the halogen atoms, a fluorine atom is particularly preferred. Of the alkyl groups, a methyl group is particularly preferred.

The most preferred $R^2$ and $R^3$ include a combination of a fluorine atom for $R^2$ and a fluorine atom for $R^3$, a combination of a hydroxy group for $R^2$ and a hydrogen atom for $R^3$, or a combination of a hydroxy group for $R^2$ and a methyl group for $R^3$.

$R^4$ is preferably an alkenyl group, an aryl group or a heterocyclic group, and, of the alkenyl group, a 2-methyl-1-propenyl group is particularly preferred, and, of the aryl groups, a phenyl group is particularly preferred.

Of the heterocyclic groups, a monocyclic heterocyclic group is preferred, and further, a monocyclic 5- or 6-membered heterocyclic group, for example, a group derived from heterocyclic compounds such as pyrrole, furan, thiophene, pyrrolidine, tetrahydrofuran, tetrahydrothiophene, imidazole, pyrazole, imidazolidine, pyrazolidine, oxazole, thiazole, oxadiazole, thiadiazole, pyridine, dihydropyridine, tetrahydropyran, piperidine, pyridazine, pyrimidine, pyrazine, piperazine, dioxane, pyran, morpholine, etc. is preferred.

Particularly preferred among the heterocyclic groups are monocyclic 5- or 6-membered heterocyclic groups containing one of an oxygen atom, a nitrogen atom and a sulfur atom as a constituent atom of the ring structure, for example, a group derived from heterocyclic compounds such as pyrrole, furan, thiophene, pyrrolidine, tetrahydrofuran, tetrahydrothiophene, pyridine, dihydropyridine, tetrahydropyran, piperidine, pyran, etc.

The most preferred among the heterocyclic groups are monocyclic 5- or 6-membered heterocyclic groups and unsaturated heterocyclic groups containing one of an oxygen atom, a nitrogen atom and a sulfur atom as a constituent atom of the ring structure.

Specifically, a group derived from furan, pyridine, or pyrrole (e.g., furyl, pyridyl or pyrrolyl) is most preferred.

$R^5$ is preferably an aryl group or an alkoxyl group, and, of the aryl groups, a phenyl group is particularly preferred, and, of the alkoxyl groups, a tertiary butoxy group is particularly preferred.

R is preferably a $C_1$-$C_8$ alkyl group, a $C_1$-$C_6$ alkoxyl group, and a $C_3$-$C_6$ cyclopropyl group; and a methyl group, an ethyl group, a propyl group, a methoxyl group, an ethoxyl group and a cyclopropyl group are particularly preferred.

Z is preferably a phenyl group substituted with one or two substituents of a fluorine atom, a chlorine atom, a methyl group or a methoxy group, or an unsubstituted phenyl group. A preferred substituting position of the substituent is a meta position of the connecting position of the phenyl group to the carbonyl group.

The preferred combination of these substituents is that $R^1$ is an alkyl group having 2 or 3 carbon atoms and having a morpholino group or a thiomorpholino group, in which the morpholino group or the thiomorpholino group may have one or more methyl groups on the carbon atom which is a constituent atom of the ring thereof, $R^2$ is a hydroxy group, $R^3$ is a hydrogen atom, $R^4$ is a furyl group or a phenyl group, $R^5$ is a tertiary butoxy group, and R is a methyl group, ethyl group or a propyl group.

Of the taxol derivatives of the present invention, derivatives which are capable of forming salts may be free forms or acid addition salts thereof. Examples of salts in the case of forming the acid addition salts include inorganic acid salts such as hydrochloride, sulfate, nitrate, hydrobromide, hydroiodide, phosphate, etc. or organic acid salts such as acetate, methanesulfonate, benzenesulfonate, toluenesulfonate, citrate, maleate, fumarate, lactate, etc.

The process for preparing the compounds of the present invention are illustrated below with reference to examples thereof.

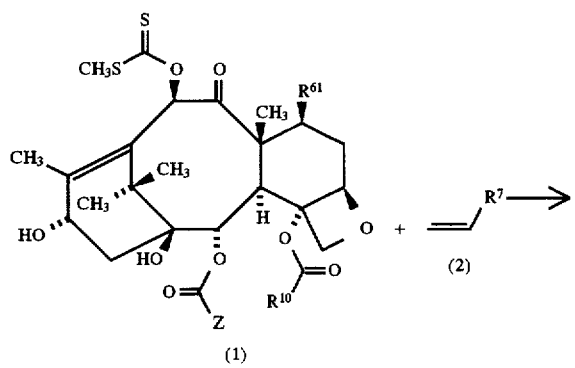

(1)

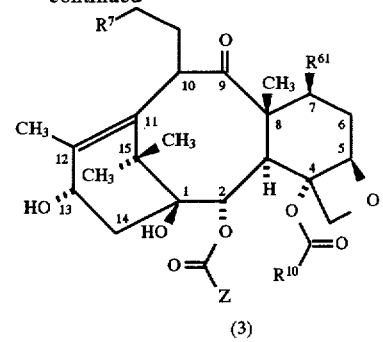

(3)

In the formulae, $R^{61}$ represents a hydrogen atom or a hydroxy group protected with a protective group, and the protective group for the hydroxy group includes, a triethylsilyl group, a 2,2,2-trichloroethoxycarbonyl group and a benzyl group, etc.

$R^7$ represents a carboxyl group, a carboxyl group protected with a protective group, an acyl group or a cyano group. The protective group for the carboxyl group is preferably a methyl group, an ethyl group, a benzyl group, a tertiary butyl group or a 2,2,2-trichloroethyl group.

$R^{10}$ represents R or R protected with a protective group (in the case where R is substituted with a hydroxy group or an amino group).

Z is as defined above.

The protective group for the hydroxy group or the amino group includes a silyl type protective group such as a triethylsilyl group or a tertiary butyldimethylsilyl group, a 1-ethoxyethyl group, a 2,2,2-trichloroethoxycarbonyl group, a benzyl group, etc.

First, the compound represented by the formula (1) (hereinafter referred to as compound (1), and compounds represented by other numerals are also represented in the same manner) and the compound (2) are reacted in a solvent in the presence of a radical initiator, and, thereafter, a trialkyltin hydride dissolved in a solvent is added dropwise in small portions thereto to give the compound (3).

Any solvent inert to the reaction is preferably used in the reaction for obtaining the compound (3), and examples thereof include toluene and benzene.

Examples of the radical initiator include 2′, 2′-azobis (isobutylonitrile) and 2,2,6,6-tetramethyl-1-piperazinyloxy free radical, and the amount of radical initiator used may be a catalytic amount.

Generally, the reaction is preferably conducted at from 50° to 90° C. with stirring.

The trialkyltin hydride includes tributyltin hydride, etc., and is used by dissolving in a solvent which is inert to the reaction such as toluene or benzene.

The compound (2) is used in an amount of from 5 to 50 molar equivalent to the compound (1), and the trialkyltin hydride is used in an amount of approximately from 0.5 to 5 molar equivalent to the compound (1).

The thus-obtained compounds (3) in which the 10-position is modified to have a carbon-carbon bond can be used for synthesis of other compounds by introducing a side chain into the 13-position.

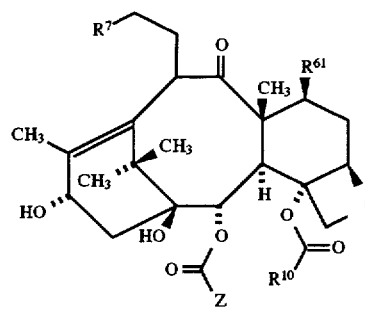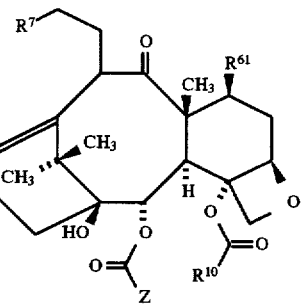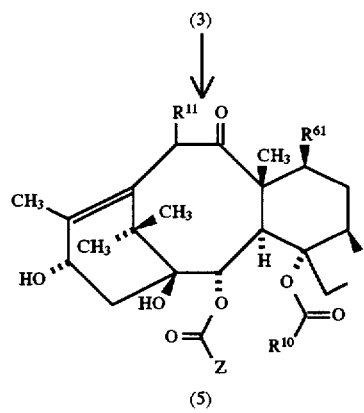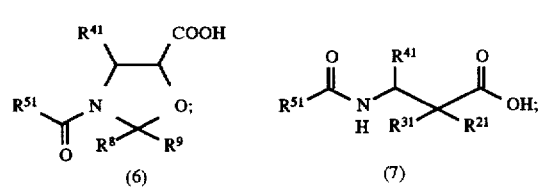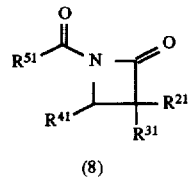

In the formulae above, $R^1$, $R^2$, $R^3$, $R^4$, $R^5$, $R^6$, $R^{61}$, $R^7$, R, $R^{10}$ and Z are as defined above.

$R^{11}$ represents $R^1$ or $R^1$ protected with a protective group (in the case of having a hydroxy group, an amino group or a carboxyl group as a substituent).

$R^{21}$ represents a hydrogen atom, a halogen atom, a hydroxy group protected with a protective group, or an alkyl group.

$R^{31}$ represents a hydrogen atom, a halogen atom, a hydroxy group protected with a protective group, or an alkyl group.

$R^{41}$ represents $R^4$ or $R^4$ protected with a protective group (in the case of having a hydroxy group, an amino group or a carboxyl group as a substituent).

$R^{51}$ represents $R^5$ or $R^5$ protected with a protective group (in the case of having a hydroxy group, an amino group or a carboxyl group as a substituent).

$R^8$ and $R^9$ each independently represents a hydrogen atom, an alkyl group, or an aryl group, and examples of preferred combinations of $R^8$ and $R^9$ include a combination in which the both groups are methyl groups and a combination in which one of the groups is a p-methoxyphenyl group and the other is a hydrogen atom.

In order to obtain compounds of the formula (I) from the above-obtained compound (3), a compound (6), a compound (7) or a compound (8) is condensed with the compound (3) to synthesize the compound (4), followed by converting the substituent at the 10-position of the compound (4) into $R^1$, and further followed by removing the protective group, etc.

Alternatively, the substituent at the 10-position of the compounds (3) is first modified to $R^{11}$ to yield a compound (5), and then the compound (5) is condensed with a compound (6), a compound (7) or a compound (8), followed by removing the protective group, etc. to give the compound of the formula (I).

Also, when the modification of the substituents at the 10-position includes a multiple steps, a part of modification steps is conducted first, and the resulting compound is condensed with a compound (6), a compound (7) or a compound (8), followed by conducting the remaining modification steps of the substituent at the 10-position to yield the compound of the formula (I).

For the condensation of the compound (6) or the compound (7) with the compound (3), a method of using an activating agent such as di(2-pyridyl)carbonate or dicyclohexylcarbodiimide, in the presence of a basic catalyst such as 4-dimethylaminopyridine can be used for the present synthesis.

For the condensation reaction using the compounds (8) with the compound (3), a method of using a base such as sodium hexamethyldisilazide can be used for the present synthesis.

The conversion of the substituents at the 10-position into a substituent corresponding to $R^1$ or $R^{11}$ can be achieved by an ordinary organic chemical conversion reaction.

For example, when $R^7$ is a carboxyl group, it can be converted into an ester, an amide, etc.

When $R^7$ is a carboxyl group protected with a protective group, it can be de-protected to a carboxyl group, and then alkylated with a Grignard reaction, etc. thereby increasing the number of carbon atoms to convert into an alcohol form.

When $R^7$ is an acyl group, it can be converted into an alcohol type substituent by reduction reaction, and alkylated with a Grignard reaction, etc. thereby increasing the number of carbon atoms to convert into an alcohol form. Also, it can be converted into an olefin type substituent by the Wittig reaction, etc.

When $R^7$ is a cyano group, it can be converted into an aminomethyl group by a reduction reaction.

The hydroxy group obtained by the above-described conversion reaction can be converted into an acyloxy group, an alkoxyl group, an amino group, an alkylamino group or an alkylthio group.

Similarly, the amino group can be converted into an acylamino group, an alkoxycarbonylamino group or an alkylamino group.

The olefin type substituent can be converted into an alkyl type substituent by a hydrogenation reaction, or into a diol type substituent by an oxidation reaction. Also, it can be converted into a substituent having a reduced number of carbon atoms, for example, a formylmethyl group or a carboxymethyl group by an oxidative decomposition reaction.

In the case of a formylmethyl group, it can be further subjected into various conversion reactions. For example, the formylmethyl group can be converted into an ethyl group to which a tertiary amine is bonded by the reaction with a secondary amine under a reductive condition.

The compound (4) can also be synthesized by the following method.

pound (5) in which $R^{61}$ is a hydroxy group, then removing the hydroxy group by the method which is known in literature references (for example, *J. Org. Chem.*, vol. 58, page 5028 (1993)) to obtain the compound (5) wherein $R^6$ is a hydrogen atom, finally condensing the resulting compound with a compound (6), a compound (7) or a compound (8) in the same manner as described above, and, if necessary, converting the moiety at the 10-position and subjecting to a de-protective reaction can be used.

Also, the target compound can be synthesized by using a know compound, 7-deoxybaccatin III, as a starting material.

Alternatively, the above target compound can be obtained by a process comprising synthesizing a compound (3) wherein $R^{61}$ is a hydrogen atom, converting this compound into a compound (4) or a compound (5), and then subjecting the resulting compound to a condensation reaction or a conversion of the substituents at the 10-position.

The compound wherein Z is a phenyl group having a substituent can be obtained by selectively hydrolyzing the ester group at the 2-position, followed by acylation according to the method described in literature reference (*Tetrahedron Lett.*, vol. 35, page 8931 (1994)).

The starting compound (1) can be synthesized from 10-O-deacetylbaccatin III, and the compound wherein $R^{61}$ is a hydroxy group protected with a triethylsilyl group is known (*Tetrahedron Lett.*, vol. 34, page 4921 (1993)).

The compound (5) wherein R is an alkyl group other than the methyl group can be synthesized as follows:

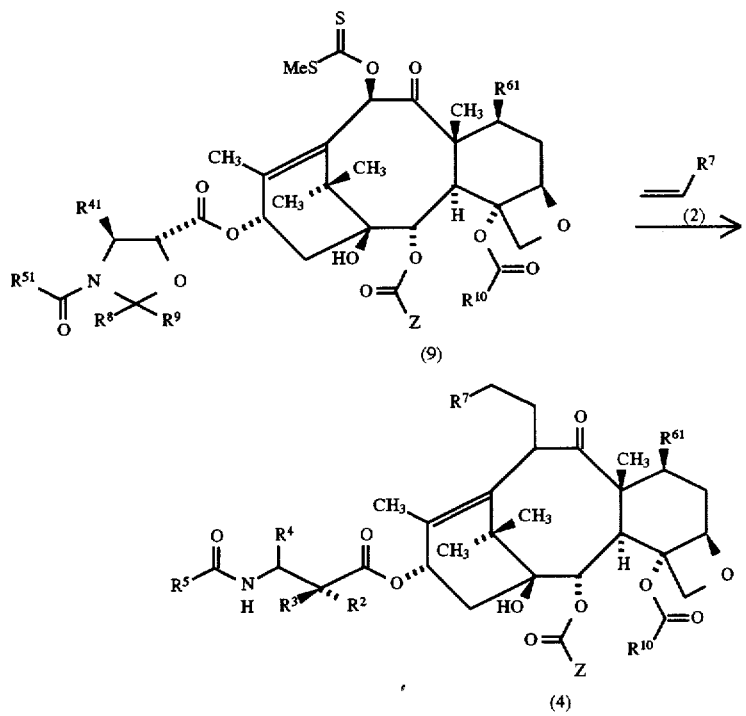

The compound (4) can be obtained by a reaction of a compound (2) and a compound (9) which was obtained by reacting a compound (1) with a compound (6).

In order to obtain the target compounds wherein $R^6$ at 7-position is a hydrogen atom, the following process may be employed, at first producing a compound (5) in which $R^{61}$ is a hydroxy group protected with a protective group, followed by removing the protective group to give a com-

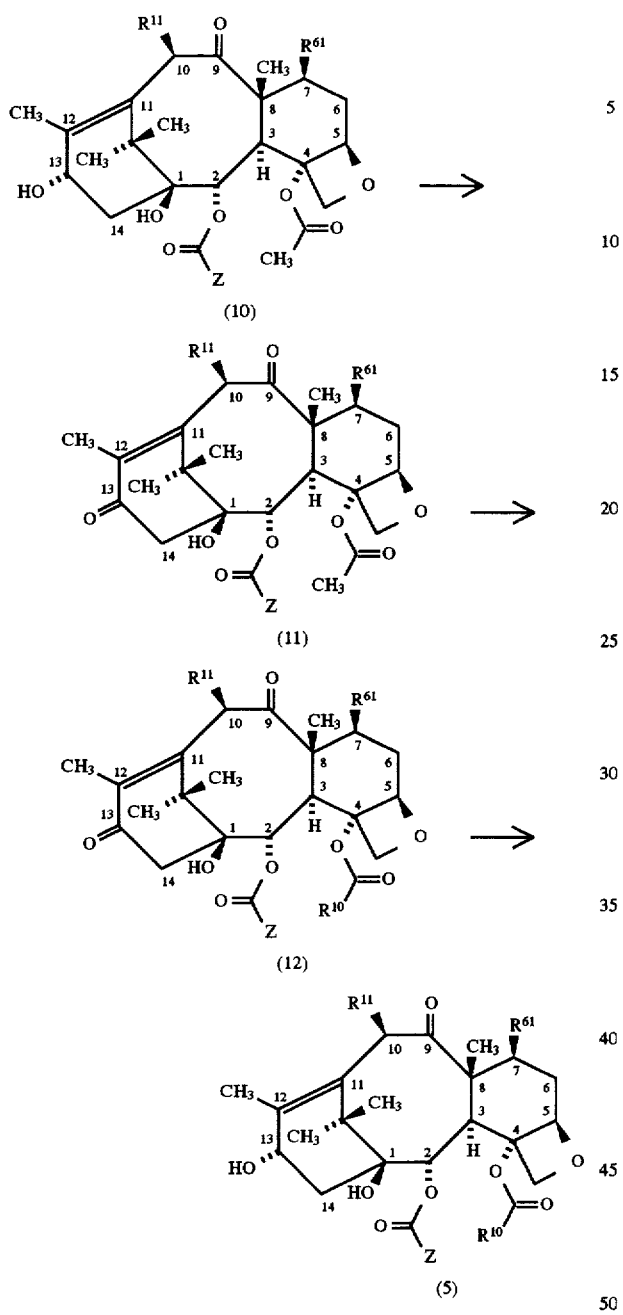

wherein $R^{11}$, $R^{61}$, Z and $R^{10}$ are as defined above, provided that $R^{10}$ is not a methyl group or a methyl group having a substituent.

In the above process, the compound (10) is first oxidized (for example, by treating it with manganese dioxide in an inert solvent such as dioxane at room temperature or under heating) to obtain the compound (11).

Then, the compound (11) is reacted with a base in a solvent inert to the reaction (for example, tetrahydrofuran, etc.) at a reaction temperature of from −100° C. to 0° C. and, thereafter, the resulting compound is reacted with a compound represented by the formula $R^{101}$-Q (wherein $R^{101}$ represents an alkyl group, Q represents a halogen atom such as an iodine atom or a bromine atom, or a leaving group such as a methanesulfonyl group, a p-toluenesulfonyl group, etc.) at −100° C. or at room temperature to obtain the compound (12).

The base which can be used includes lithium hexamethyldisilazide, sodium hexamethyldisilazide, potassium hexamethyldisilazide, lithium diisopropylamide, a tertiary butoxy potassium, sodium hydride, etc., and the amount of the base is from 1 to 10 molar equivalents to the compound (11).

The resulting compound (12) is reduced by treating with a reducing agent such as sodium borohydride in a solvent, for example, methanol or tetrahydrofuran, etc. to obtain the compound (5).

Also, the compound (5) wherein R is an alkyl group other than the methyl group can be synthesized by converting the acetoxy group at the 4-position into a hydroxy group, followed by acylation according to the method described, for example, in J. Org. Chem., vol. 59, page 6156 (1994). Similarly, the compound wherein R is an alkoxy group can be synthesized by the above method.

The starting compound (6), (7) or (8) can be synthesized by conventional procedures. For example, the compound (6) can be prepared by the method described in Tetrahedron Letter, vol. 33, page 5185 (1992), the compound (7) can be prepared by the method described in Journal of American Chemical Society, vol. 110, page 5917 (1988), and the compound (8) can be prepared by the method described in Tetrahedron Letter, vol. 34, page 4149 (1993).

The compounds according to the present invention are useful as a remedy for various types of cancers such as lung cancer, digestive cancer, ovarian cancer, carcinoma uteri, breast cancer, hepatoma, carcinoma of the head and neck, blood cancer, renal cancer or testicle tumor.

The compounds of the present invention can be administered in various dosage forms of parenteral (e.g., intravenous, intramuscular or subcutaneous injection), oral, or percutaneous administration. Among these dosage forms, intravenous administration with liquid preparation, and oral administration are preferred. The liquid preparation can be manufactured by forming an acid addition with a pharmaceutical acceptable acid or an alkali metal salt such as sodium. In the oral administration, the compounds of the present invention can be used as a free compound or a salt thereof.

The pharmaceutical preparations containing one or more compounds of the present invention as an active ingredient can be appropriately selected according to the administration route and can be prepared by conventional preparation methods. Examples of the pharmaceutical preparations for oral administration include tablets, powders, granules, capsules, solutions, syrups, elixirs, and oily or aqueous suspensions. The injectable preparations may contain adjuvants, such as stabilizers, antiseptics and solubilizers. The injectable solution which may contain these adjuvants may be put into a container, and solidified by, for example, lyophilization to prepare a solid preparation which is dissolved on use.

The liquid preparations include solutions, suspensions and emulsions. They may contain adjuvants, such as suspending agents and emulsifiers.

The compounds according to the present invention can be used as an antitumor agent for mammal, particularly human. The dose of the compound of the present invention as the active ingredient of medicine for human use is generally in the range of about 0.5 to 50 mg per 1 m² of body surface per day, and preferably about 1 to 20 mg per 1 m² of body surface per day. The oral or non-oral administration is preferably effected once a day at appropriate intervals.

BEST MODE FOR CARRYING OUT INVENTION

The present invention is further illustrated by the following examples.

EXAMPLE 1
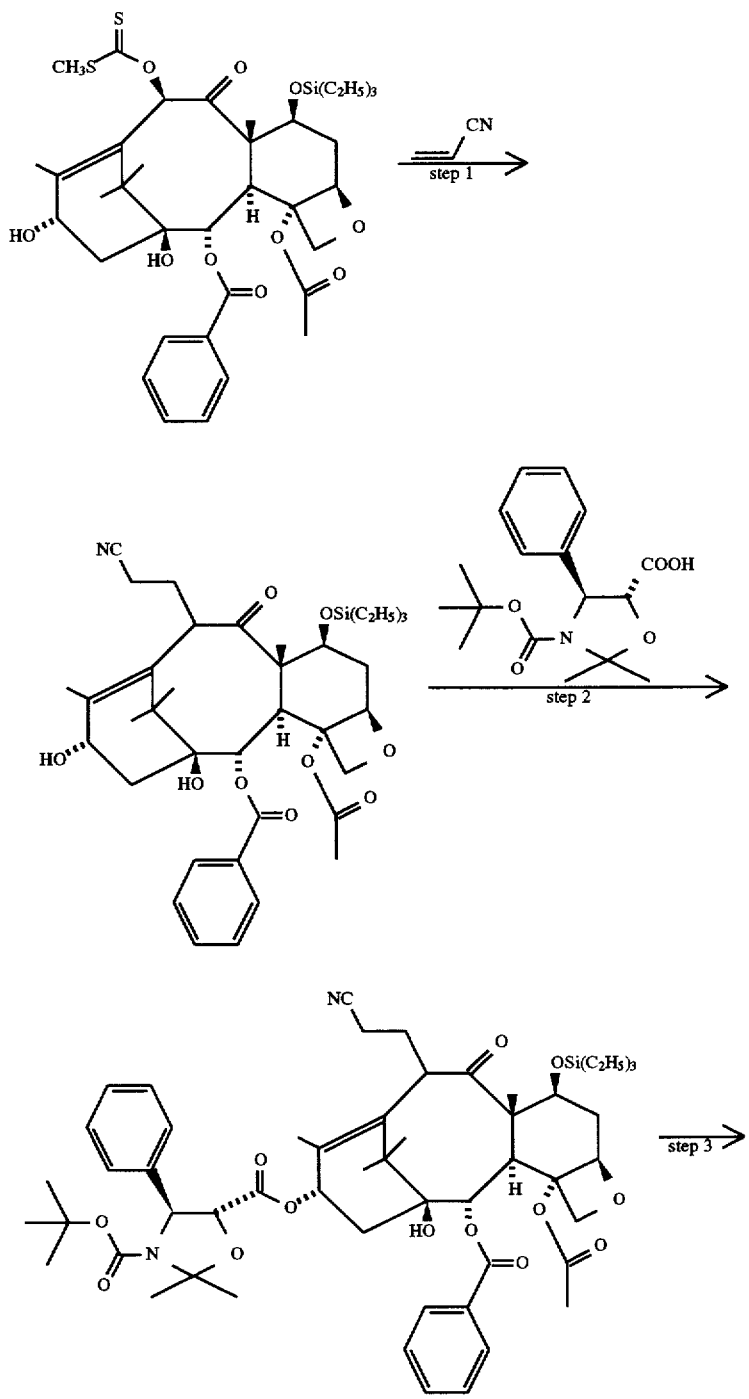

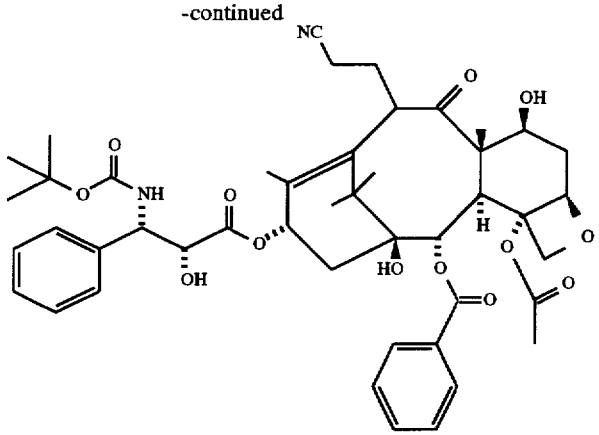
-continued

Step 1: 10-(2-cyanoethyl)-10-deacetoxy-7-O-triethylsilylbaccatin III

In a nitrogen gas atmosphere, 200 mg of 10-deacetyl-10-O-(methylthio)thiocarbonyl-7-O-triethylsilylbaccatin III was suspended in 3 ml of dried toluene, and a catalytic amount of 2,2'-azobis(isobutyronitrile) and 20 μl of acrylonitrile were added thereto, followed by replacing with a nitrogen gas. After heated at 80° C., a solution of 123 μl of tributyltin hydride dissolved in 0.3 ml of toluene and 200 μl of acrylonitrile were simultaneously added dropwise thereto over 30 minutes under stirring. After completion of the dropwise addition, the mixture was cooled to room temperature, and the solvent of the reaction solution was distilled off under reduced pressure. The resulting residue was purified by silica gel thin layer chromatography (a developing solvent; chloroform: acetone=95:5 (v/v)) to yield 109 mg of the titled compound as a colorless amorphous solid.

$^1$H-NMR (CDCl$_3$/TMS) δ(ppm): 0.58(6H, m), 0.97(9H, t), 1.06(3H, s), 1.09(3H,s), 1.63(3H, s), 1.94(2H, m), 2.05 (3H, d, J=1 Hz), 2.06(1H, m), 2.29(3H, s), 3.91(1H, t, J=7 Hz), 4.00(1H, d, J=7 Hz), 4.15(1H, d, J=8 Hz), 4.30(1H, d, J=8 Hz), 4.58(1H, dd, J=11 Hz, 6.5 Hz), 4.86(1H, m), 4.97(1H, d, J=9 Hz), 5.59(1H, d, J=7 Hz), 7.48(2H, t), 7.60(1H, t), 8.11(2H, m).

Step 2: 13-O-[(2R,3S)-N-(tert-butoxycarbonyl)-N,O-isopropylidene-3-phenylisoserinyl]-10-(2-cyanoethyl)-10-deacetoxy-7-O-triethylsilylbaccatin III 107 mg of the compound obtained in the above Step 1 and 93 mg of (4S,5R)-3-(tert-butoxycarbonyl)-2,2-dimethyl-4-phenyloxazoline-5-carboxylic acid were dissolved in 5 ml of dried methylene chloride, and 16 mg of 4-dimethylaminopyridine and 70 mg of dicyclohexylcarbodiimide were added thereto, followed by stirring for 15 hours at room temperature. The precipitated insoluble material was removed by filtration, and the solvent was evaporated under reduced pressure. The resulting residue was purified by silica gel thin layer chromatography (a developing solvent; chloroform:acetone=95:5 (v/v)) to yield 118 mg of the titled compound as a colorless amorphous solid.

$^1$H-NMR (CDCl$_3$/TMS) δ(ppm): 0.57(6H, m), 0.97(9H, t), 1.10(9H, br), 1.11(3H, s), 1.20(3H, s), 1.60(3H, s), 1.76(3H, s), 1.81(3H, s), 1.86(3H, s), 1.92(3H, s), 2.14(2H, m), 2.37(2H, t, J=7 Hz), 2.51(2H, m), 3.89(2H, m), 4.11(1H, d, J=8 Hz), 4.24(1H, d, J=8 Hz), 4.46(1H, d, J=7 Hz), 4.53(1H, dd, J=11 Hz, 6.5 Hz), 4.89(1H, d, J=8.5 Hz), 5.05(1H, br), 5.61(1H, d, J=7 Hz), 6.23(1H, t, J=9 Hz), 7.35(5H, m), 7.50(2H, t), 7.64(1H, t), 8.04(2H, m).

Step 3: 13-O-[(2R,3S)-3-(tert-butoxycarbonylamino)-2-hydroxy-3-phenylpropionyl]-10-(2-cyanoethyl)-10-deacetoxybaccatin III 118 mg of the compound obtained in the above Step 2 was dissolved in 2 ml of formic acid, followed by stirring for 2 hours at room temperature. After distilling off the solvent under reduced pressure, an aqueous sodium bicarbonate solution was added thereto, and the mixture was extracted with chloroform-methanol (90:10 (v/v)). The extract layer was dried over anhydrous magnesium sulfate, the solvent was evaporated under reduced pressure, and the residue was dissolved in 5 ml of tetrahydrofuran. 41 μl of di-tert-butyl dicarbonate was added thereto, followed by stirring at room temperature for 3.5 hours. The solvent was evaporated under reduced pressure, the resulting residue was purified by silica gel thin layer chromatography (a developing solvent; chloroform:acetone=95:5 (v/v)) to obtain 52 mg of the titled compound as a colorless solid.

Melting Point: 157°–162° C.

$^1$H-NMR (CDCl$_3$/TMS) δ(ppm): 1.12(3H, s), 1.20(3H, s), 1.33(9H, s), 1.65(3H, s), 1.84(3H, s), 2.22(1H, m), 2.31(1H, m), 2.39(3H, s), 2.50(3H, m), 2.63(1H, m), 3.36(1H, d, J=4 Hz), 3.94(1H, d, J=7 Hz), 3.99(1H, dd, J=10 Hz, 3.5 Hz), 4.18(1H, d, J=8.5 Hz), 4.31(1H, d, J=8.5 Hz), 4.43(1H, m), 4.63(1H, br), 4.96(1H, d, J=9 Hz), 5.26(1H, m), 5.39(1H, d, J=9.5 Hz), 5.66(1H, d, J=7 Hz), 6.19(1H, t, J=9 Hz), 7.3–7.45(5H, m), 7.50(2H, t), 7.61(1H, t), 8.11(2H, d).

EXAMPLE 2
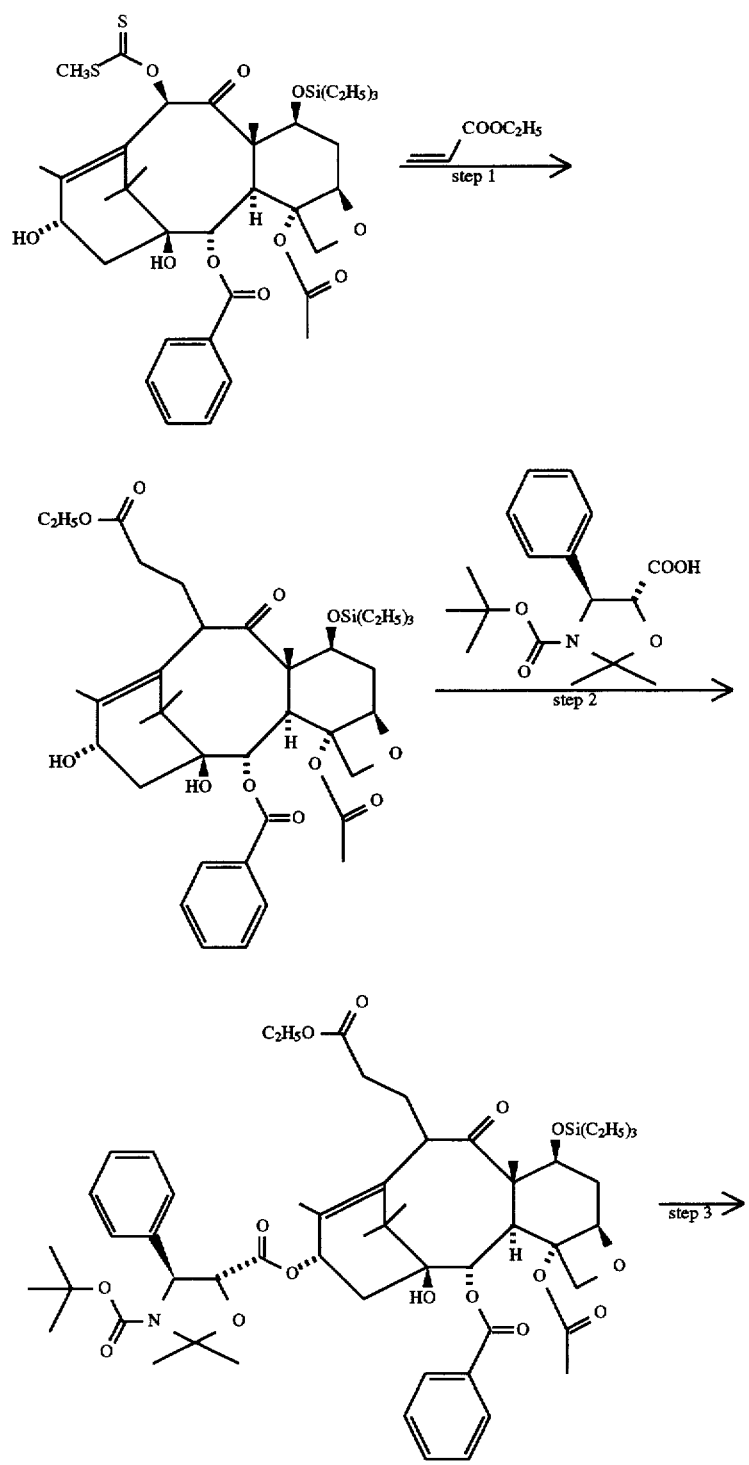

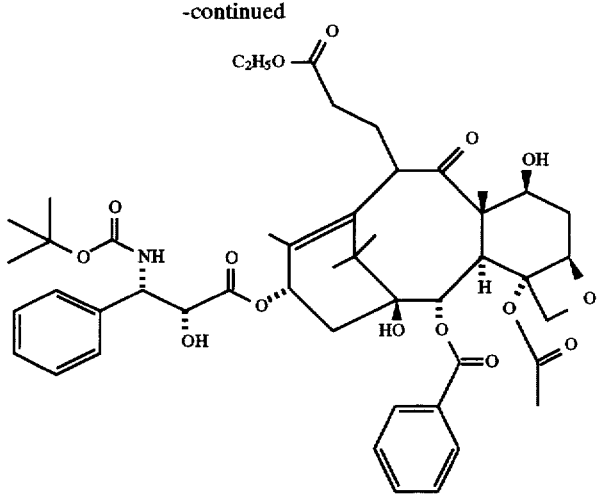

Step 1: 10-Deacetoxy-10-(2-ethoxycarbonylethyl)-7-O-triethylsilylbaccatin III

The reaction was conducted in the same manner as in Step 1 of Example 1 except for using ethyl acrylate in place of acrylonitrile to yield the titled compound.

$^1$H-NMR (CDCl$_3$/TMS) δ(ppm): 0.58(6H, m), 0.92(9H, t), 1.06(3H, s), 1.12(3H, s), 1.26(3H, t), 1.62(3H, s), 1.96 (3H, s), 2.29(3H, s), 3.83(1H, m), 4.03(1H, d, J=7 Hz), 4.15(4H, m), 4.30(1H, d, J=8 Hz), 4.54(1H, dd, J=11 Hz, 6.5 Hz), 4.86(1H, m), 4.96(1H, d, J=9 Hz), 5.60(1H, d, J=7 Hz), 7.47(2H, t), 7.60(1H, t), 8.11(2H, m).

Step 2: 13-O-[(2R,3S)-N-(tert-butoxycarbonyl)-N,O-isopropylidene-3-phenylisoserinyl]-10-deacetoxy-10-(2-ethoxycarbonylethyl)-7-O-triethylsilylbaccatin III The compound obtained in the above Step 1 was reacted in the same manner as in Step 2 of Example 1 to yield the titled compound as a colorless amorphous solid.

$^1$H-NMR (CDCl$_3$/TMS) δ(ppm): 0.56(6H, m), 0.95(9H, t), 1.10(9H, br), 1.15(3H, s), 1.21(3H, s), 1.26(3H, t, J=7 Hz), 1.60(3H, s), 1.78(3H, s), 1.81(3H, s), 1.82(6H, s), 2.14(2H, m), 2.29(2H, m), 2.43(2H, m), 3.80(1H, dd, J=9 Hz, 5 Hz), 3.90(1H, d, J=7 Hz), 4.13(4H, m), 4.22(1H, d, J=8 Hz), 4.48(2H, m), 4.88(1H, d, J=8.5 Hz), 5.05(1H, br), 5.62(1H, d, J=7 Hz), 6.24(1H, t, J=9 Hz), 7.35(5H, m), 7.50(2H, t), 7.64(1H, t), 8.04(2H, m).

Step 3: 13-O-[(2R,3S)-3-(tert-butoxycarbonylamino)-2-hydroxy-3-phenylpropionyl]-10-deacetoxy-10-(2-ethoxycarbonylethyl)baccatin III The compound obtained in the above Step 2 was reacted in the same manner as in Step 3 of Example 1 to yield the titled compound as a colorless solid.

Melting Point: 126°–128° C.

$^1$H-NMR (CDCl$_3$/TMS) δ(ppm): 1.14(3H, s), 1.20(3H, s), 1.27(3H, t, J=7 Hz), 1.33(9H, s), 1.64(3H, s), 1.73(3H, s), 1.87(1H, m), 2.20(1H, m), 2.30(1H, m), 2.37(3H, s), 3.32 (1H, d, J=4 Hz), 3.94(3H, m), 4.13(2H, m), 4.20(1H, d, J=8.5 Hz), 4.30(1H, d, J=8.5 Hz), 4.37(1H, m), 4.60(1H, m), 4.96(1H, dd, J=9.5 Hz), 5.26(1H, br), 5.37(1H, d, J=9.5 Hz), 5.66(1H, d, J=7 Hz), 6.18(1H, t, J=9 Hz), 7.3–7.45(5H, m), 7.50(2H, t), 7.61(1H, t), 8.11(2H, d).

EXAMPLE 3

10-(3-Aminopropyl)-13-O-[(2R,3S)-3-(tert-butoxycarbonylamino)-2-hydroxy-3-phenylpropionyl]-10-deacetoxybaccatin III

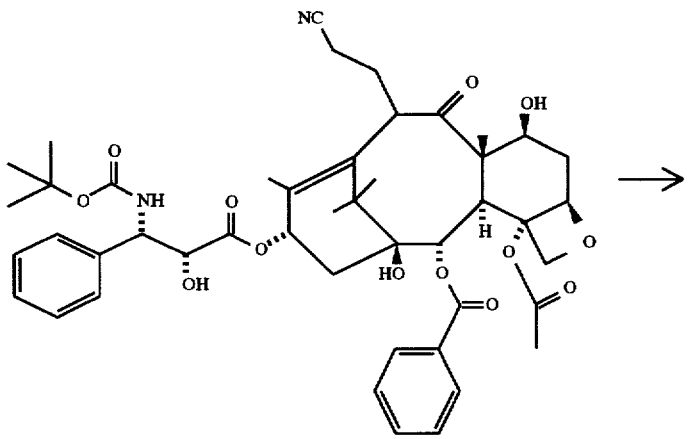

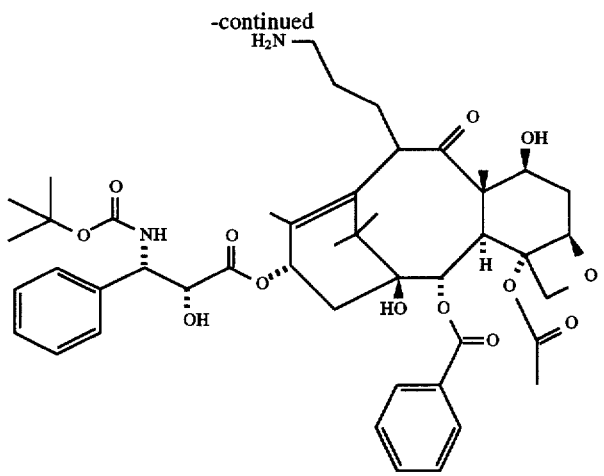

32 mg of the compound obtained in Step 3 of Example 1 was dissolved in 3 ml of tetrahydrofuran, and about 1 ml of a suspension of activated Raney nickel in tetrahydrofuran was added thereto. Further, 0.5 ml of a concentrated aqueous ammonia was added thereto, followed by stirring in a hydrogen gas for 2 hours at room temperature. The reaction solution was diluted with a mixed solvent of chloroform-methanol-distilled water (6:4:1 (v/v)), and the insoluble material was removed by filtration. After evaporation of the solvent of the filtrate under reduced pressure, the residue was purified by silica gel thin layer chromatography (a developing solvent; chloroform-methanol-distilled water= 6:4:1 (v/v)) to yield 22 mg of the titled compound as a colorless solid.

Melting Point: 177°–184° C. (decomposition)

$^1$H-NMR (CDCl$_3$—CD$_3$OD(1:1(v/v))/TMS) δ(ppm): 1.12(3H, s), 1.20(3H, s), 1.39(9H, s), 1.64(3H, s), 1.83(3H, s), 2.38(3H, s), 2.94(2H, m), 3.85(1H, m), 3.97(1H, d, J=7 Hz), 4.27(2H, AB type q), 4.37(1H, m), 4.53(1H,m), 5.02 (1H, d, J=9 Hz), 5.15(1H, br), 5.66(1H, d, J=7 Hz), 6.12(1H, t, J=8.5 Hz), 7.25–7.45(5H, m), 7.52(2H, t), 7.64(1H, t), 8.11(2H, d).

EXAMPLE 4

10-(3-Acetaminopropyl)-13-O-[(2R,3S)-3-(tert-butoxycarbonylamino)-2-hydroxy-3-phenylpropionyl]-10-deacetoxybaccatin III

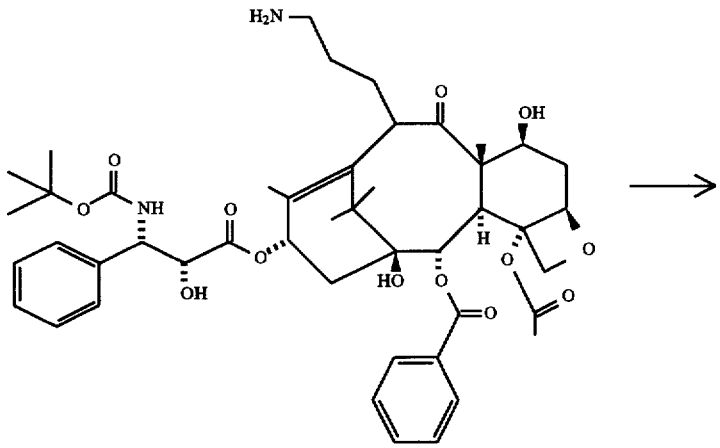

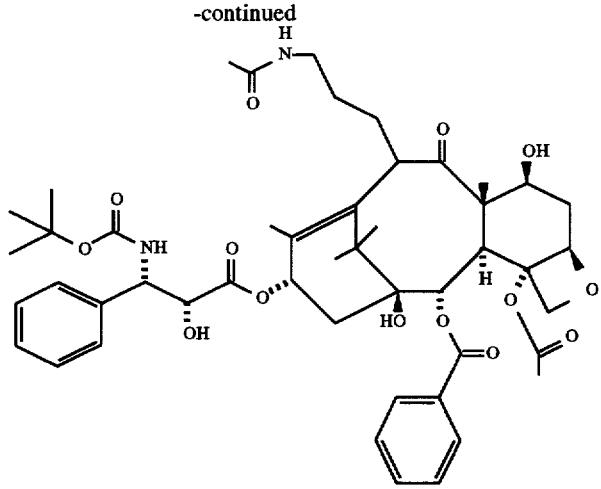

10 mg of the compound obtained in Example 3 was dissolved in 0.5 ml of tetrahydrofuran, and 0.2 μl of N-methoxydiacetamide and 1.6 μl of triethylamine dissolved in 0.1 ml of tetrahydrofuran were added thereto, followed by stirring at room temperature for 16 hours. After evaporation of the solvent under reduced pressure, the residue was purified by silica gel thin layer chromatography (a developing solvent; chloroform:methanol=20:1 (v/v)) to yield 8 mg of the titled compound as a colorless solid.

Melting Point: 157°–161° C.

¹H-NMR (CDCl₃/TMS) δ(ppm): 1.13(3H, s), 1.19(3H, s), 1.33(9H, s), 1.64(3H, s), 1.79(3H, s), 1.98(3H, s), 2.22 (1H, m), 2.39(3H, s), 3.09(1H, m), 3.47(1H, m), 3.95(1H, d, J=7 Hz), 3.99(1H, d, J=7 Hz), 4.19(1H, d, J=8.5 Hz), 4.29(1H, d, J=8.5 Hz), 4.40(1H, dd, J=11 Hz, c6.5 Hz), 4.61(1H, br), 4.94(1H, d, J=8.5 Hz), 5.27(1H, m), 5.55(1H, d, J=9.5 Hz), 5.66(1H, d, J=7 Hz), 6.16(1H, t, J=8.5 Hz), 7.3–7.45(5H, m), 7.52(2H, t), 7.62(1H, t), 8.11(2H, d).

EXAMPLE 5

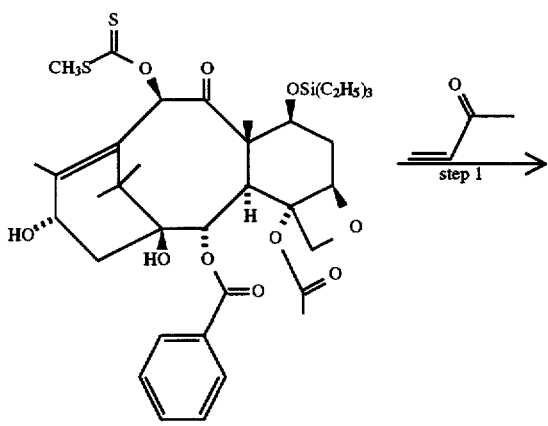

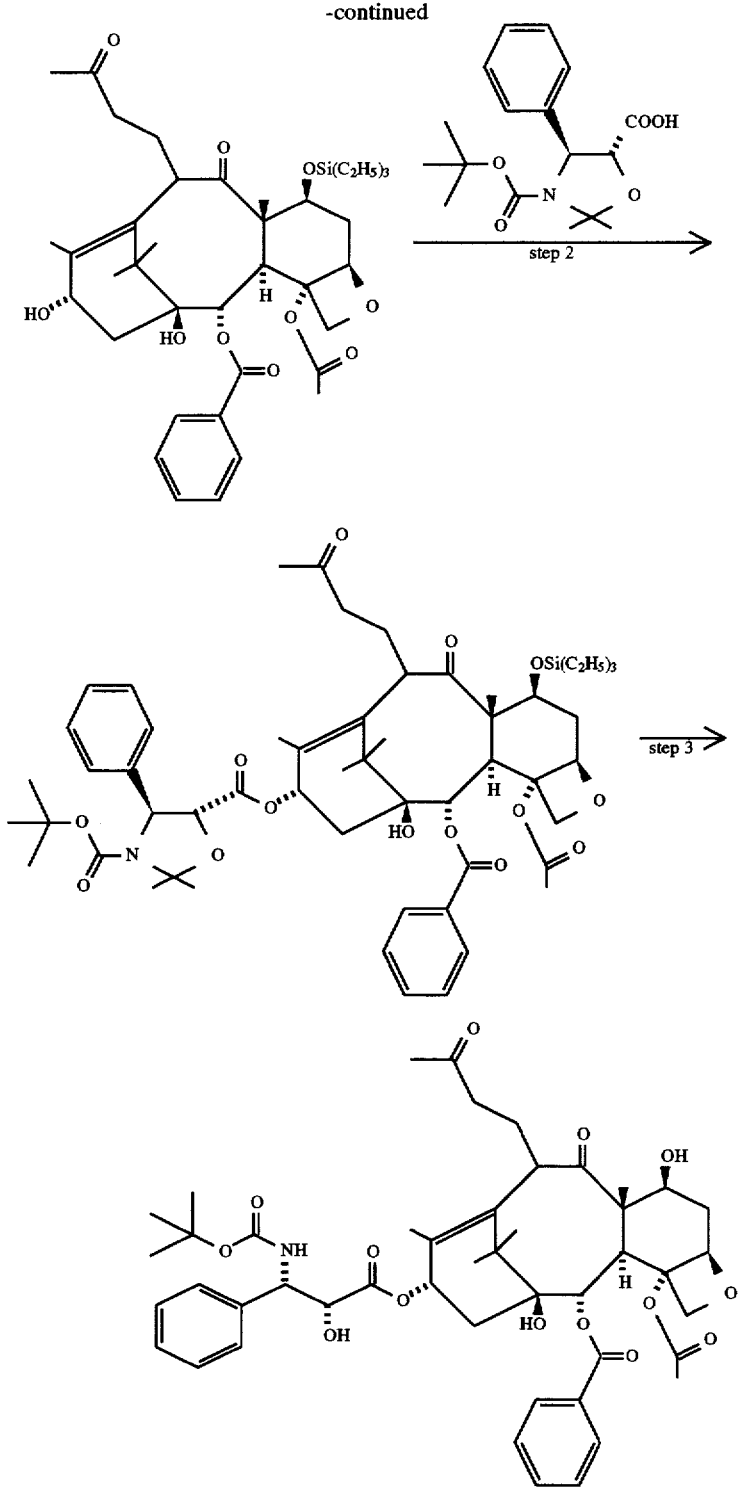

Step 1: 10-Deacetoxy-10-(3-oxobutyl)-7-O-triethylsilylbaccatin III

The reaction was conducted in the same manner as in Step 1 of Example 1 except for using methylvinyl ketone in place of acrylonitrile to yield the titled compound.

$^1$H-NMR (CDCl$_3$)/TMS) δ(ppm): 0.59(6H, m), 0.97(9H, t), 1.05(3H, s), 1.12(3H, s), 1.63(3H, s), 1.95(3H, s), 2.16 (3H, s), 2.29(3H, s), 3.79(1H, m), 4.03(1H, d, J=7 Hz), 4.17(1H, d, J=8.5 Hz), 4.30(1H, d, J=8.5 Hz), 4.54(1H, dd, J=10.5 Hz, 6.5 Hz), 4.85(1H, m), 4.96(1H, d, J=9 Hz), 5.60(1H, d, J=7 Hz), 7.47(2H, t), 7.60(1H, t), 8.11(2H, m).

Step 2: 13-O-[(2R,3S)-N-(tert-Butoxycarbonyl)-N,O-isopropylidene-3-phenylisoserinyl]-10-deacetoxy-10-(3-oxobutyl)-7-O-triethylsilylbaccatin III The compound obtained in the above Step 1 was reacted in the same manner as in Step 2 of Example 1 to yield the titled compound as a colorless amorphous solid.

¹H-NMR(CDCl₃/TMS) δ(ppm): 0.57(6H, m), 0.96(9H, t), 1.13(12H, br), 1.20(3H, s), 1.60(3H, s), 1.77(3H, s), 1.79 (6H, s), 1.80(3H, s), 2.15(3H, s), 3.78(1H, m), 3.88(1H, d, J=7.5 Hz), 4.11(1H, d, J=8.5 Hz), 4.23(1H, d, J=8.5 Hz), 4.47(2H, m), 4.87(1H, d, J=8 Hz), 5.05(1H, br), 5.61(1H, d, J=7.5 Hz), 6.23(1H, t, J=9.5 Hz), 7.35(5H, m), 7.50(2H, t), 7.63(1H, t), 8.04(2H, m).

Step 3: 13-O-[(2R,3S)-3-(tert-Butoxycarbonylamino)-2-hydroxy-3-phenylpropionyl]-10-deacetoxy-10-(3-oxobutyl) baccatin III The compound obtained in the above Step 2 was reacted in the same manner as in Step 3 of Example 1 to yield the titled compound as a colorless solid.

Melting Point: 137°–142° C.

¹H-NMR (CDCl₃/TMS) δ(ppm): 1.13(3H, s), 1.20(3H, s), 1.33(9H, s), 1.63(3H, s), 1.76(3H, s), 2.14(3H, s), 2.38(3H, s), 3.85(1H, m), 3.94(1H, d, J=7 Hz), 4.18(1H, d, J=8.5 Hz), 4.29(1H, d, J=8.5 Hz), 4.33(1H, m), 4.61(1H, br), 4.94(1H, d, J=9 Hz), 5.27(1H, br), 5.38(1H, m), 5.65(1H, d, J=7 Hz), 6.19(1H, t, J=8.5 Hz), 7.3–7.45(5H, m), 7.49(2H, t), 7.60 (1H, t), 8.10(2H, d).

EXAMPLE 6

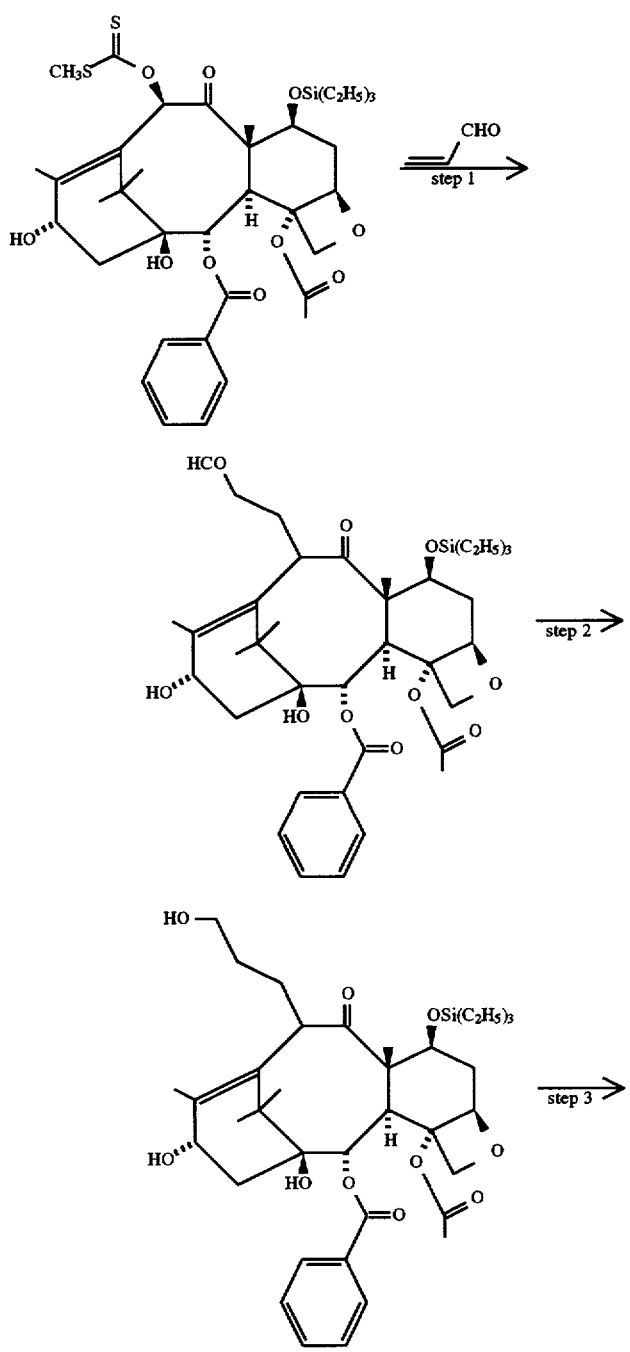

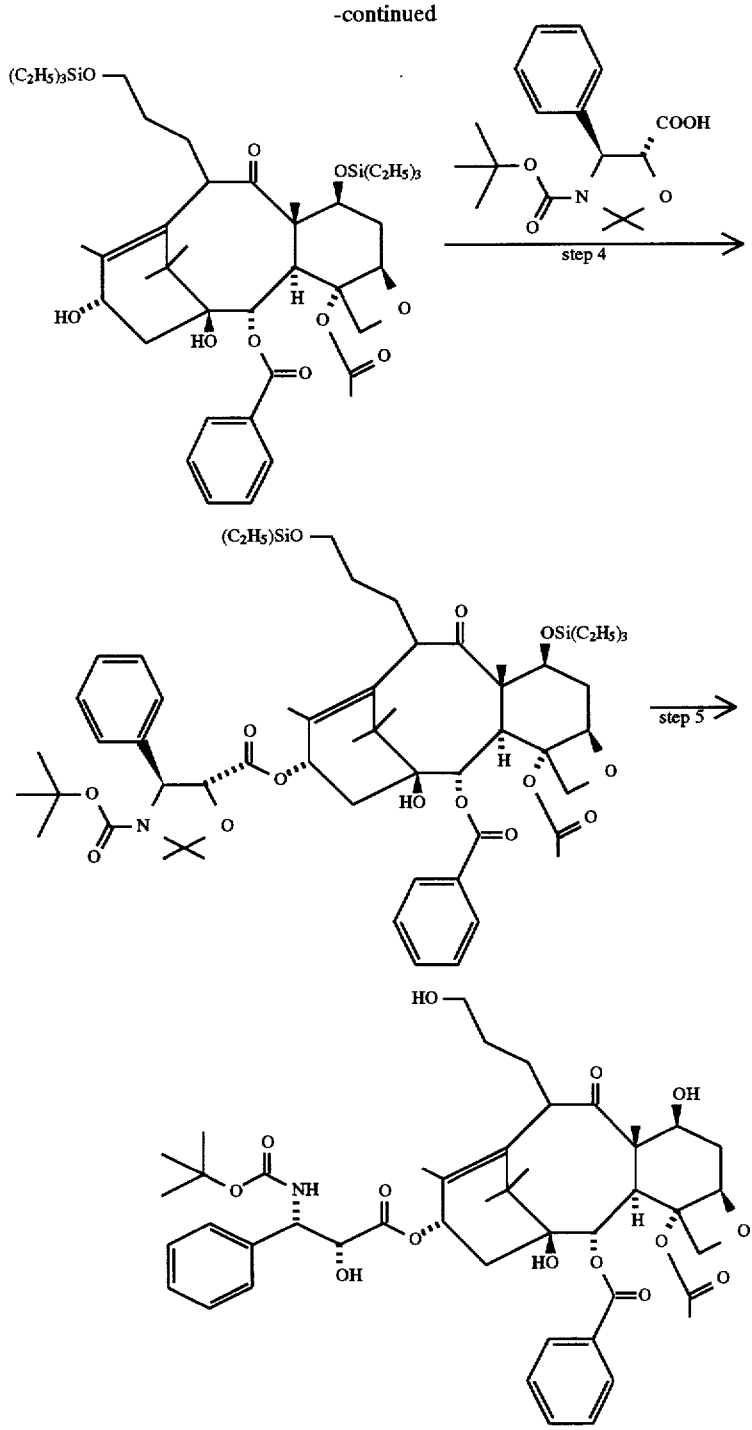

Step 1: 10-Deacetoxy-10-(3-oxopropyl)-7-O-triethylsilylbaccatin III

The reaction was conducted in the same manner as in Step 1 of Example 1 except for using acrolein in place of acrylonitrile to yield the titled compound.

¹H-NMR (CDCl₃/TMS) δ(ppm): 0.57(6H, m), 0.96(9H, t), 1.05(3H, s), 1.12(3H, s), 1.63(3H, s), 1.94(3H, s), 2.29 (3H, s), 3.82(1H, m), 4.02(1H, d, J=7 Hz), 4.16(1H, d, J=8.5 Hz), 4.30(1H, d, J=8.5 Hz), 4.54(1H, dd, J=11 Hz, 6.5 Hz), 4.85(1H, m), 4.96(1H, d, J=9 Hz), 5.60(1H, d, J=7 Hz), 7.47(2H, t), 7.60(1H, t), 8.10(2H, m), 9.80(1H, s).

Step 2: 10-Deacetoxy-10-(3-hydroxypropyl)-7-O-triethylsilylbaccatin III 73 mg of the compound obtained in the above Step 1 was dissolved in 3 ml of methanol, and 16 mg of sodium borohydride which was divided into 4 portions was added thereto in 4 times at an interval of 1 hour while stirring under ice-cooling. After further stirring for 30 minutes, 1N hydrochloric acid was added to the reaction solution, the mixture was extracted with chloroform. After drying over anhydrous magnesium sulfate, the solvent was evaporated under reduced pressure, and the residue was purified by silica gel thin layer chromatography (a developing solvent; chloroform:methanol=20:1 (v/v)) to obtain 39 mg of the titled compound as a colorless solid.

$^1$H-NMR (CDCl$_3$/TMS) δ(ppm): 0.55(6H, m), 0.95(9H, t), 1.05(3H, s), 1.11(3H, s), 1.62(3H, s), 1.88(1H, m), 1.97(3H, s), 2.29(3H, s), 2.49(1H, m), 3.68(3H, m), 3.83 (1H, m), 4.07(1H, d, J=7 Hz), 4.17(1H, d, J=8.5 Hz), 4.30(1H, d, J=8.5 Hz), 4.55(1H, dd, J=10.5 Hz, 6.5 Hz), 4.84(1H, t, J=8 Hz), 4.97(1H, d, J=8 Hz), 5.60(1H, d, J=7 Hz), 7.47(2H, t), 7.59(1H, t), 8.10(2H, d).

Step 3: 10-Deacetoxy-10-(3-triethylsilyloxypropyl)-7-O-triethylsilylbaccatin III 39 mg of the compound obtained in the above Step 2 was dissolved in 2 ml of dried methylene chloride, and 4.5 mg of imidazole and 10.5 μl of triethylsilyl chloride were added thereto, followed by stirring at room temperature for one hour. Further, 5 mg of imidazole and 10.5 μl of triethylsilyl chloride were added thereto, followed by stirring for 15 minutes. 1N hydrochloric acid was added to the reaction solution, the mixture was extracted with ethyl acetate, and the extracted organic layer was washed with a saturated aqueous sodium chloride solution. After drying over anhydrous magnesium sulfate, the solvent was evaporated under reduced pressure, the residue was purified by silica gel thin layer chromatography (a developing solvent; chloroform:acetone=20:1 (v/v)) to yield 34 mg of the titled compound as a colorless amorphous solid.

$^1$H-NMR (CDCl$_3$/TMS) δ(ppm): 0.5–0.65(12H, m), 0.95 (18H, m), 1.05(3H, s), 1.11(3H, s), 1.62(3H, s), 1.76(1H, m), 1.88(1H, m), 1.97(3H, s), 2.07(1H, m), 2.29(3H, s), 2.48 (1H, m), 3.64(2H, m), 3.81(1H, dd, J=10 Hz, 4 Hz), 4.07 (1H, d, J=7 Hz), 4.17(1H, d, J=8.5 Hz), 4.29(1H, d, J=8.5 Hz), 4.55(1H, dd, J=10.5 Hz, 6.5 Hz), 4.85(1H, t, J=8 Hz), 4.97(1H, d, J=8 Hz), 5.60(1H, d, J=7 Hz), 7.47(2H, t), 7.59(1H, t), 8.10(2H, d).

Step 4: 13-O-[(2R,3S)-N-(tert-Butoxycarbonyl)-N,O-isopropylidene-3-phenylisoserinyl]-10-deacetoxy-10-(3-triethylsilyloxypropyl)-7-O-triethylsilylbaccatin III The compound obtained in the above Step 3 was reacted in the same manner as in Step 2 of Example 1 to yield the titled compound as a colorless amorphous solid.

$^1$H-NMR (CDCl$_3$/TMS) δ(ppm): 0.5–0.65(12H, m), 0.9–1.0(18H, t), 1.13(12H, br), 1.20(3H, s), 1.60(3H, s), 1.77(3H, s), 1.81(6H, s), 1.83(3H, s), 2.09(4H, m), 2.44(1H, m), 3.64(3H, m), 3.76(1H, dd, J=9.5 Hz, 4 Hz), 3.94(1H, d, J=7 Hz), 4.12(1H, d, J=8.5 Hz), 4.23(1H, d, J=8.5 Hz), 4.45(1H, d, J=7 Hz), 4.49(1H, dd, J=10 Hz, 6.5 Hz), 4.88(1H, t, J=8 Hz), 5.05(1H, br), 5.62(1H, d, J=7 Hz), 6.24(1H, t, J=8.5 Hz), 7.35(5H, m), 7.49(2H, t), 7.63(1H, t), 8.05(2H, m).

Step 5: 13-O-[(2R,3S)-3-(tert-Butoxycarbonylamino)-2-hydroxy-3-phenylpropionyl]-10-deacetoxy-10-(3-hydroxypropyl)baccatin III The compound obtained in the above Step 4 was reacted in a similar manner as in Step 3 of Example 1 to yield the titled compound as a colorless solid.

Melting Point: 130°–138° C.

$^1$H-NMR (CDCl$_3$/TMS) δ(ppm): 1.14(3H, s), 1.21(3H, s), 1.33(9H, s), 1.64(3H, s), 1.77(3H, s), 2.22(1H, m), 2.38(3H, s), 2.57(1H, m), 3.30(1H, br), 3.81(1H, d, J=6.5 Hz), 4.00 (1H, d, J=7 Hz), 4.20(4H, m), 4.32(2H, m), 4.61(1H, br), 4.95(1H, d, J=9.5 Hz), 5.27(1H, br), 5.37(1H, m), 5.67(1H, d, J=7 Hz), 6.20(1H, t, J=8.5 Hz), 7.3–7.45(5H, m), 7.50(2H, t), 7.61(1H, t), 8.11(2H, d).

EXAMPLE 7

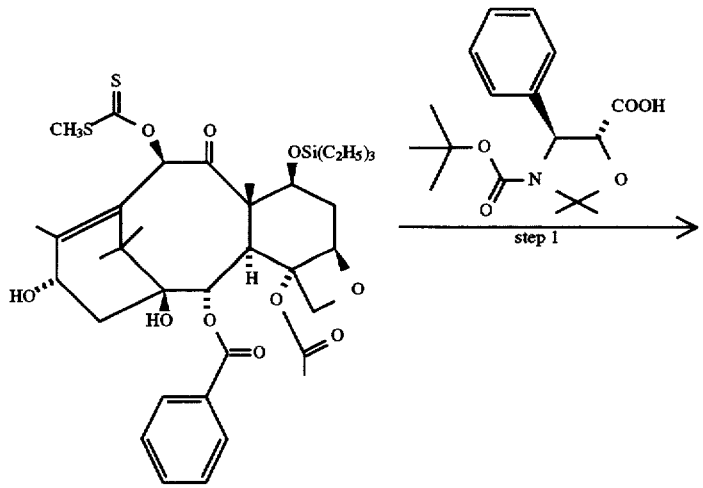

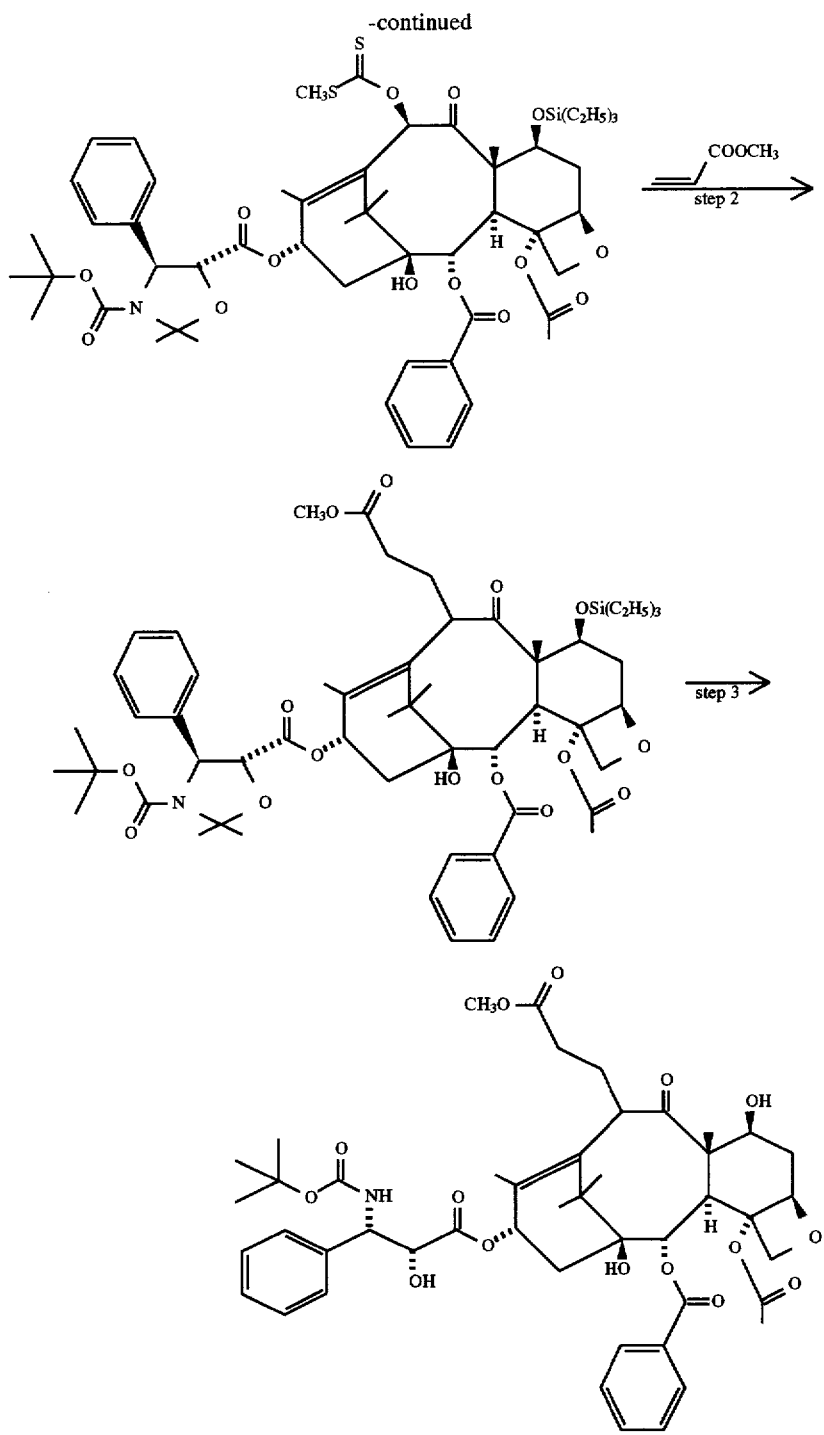

Step 1: 13-O-[(2R,3S)-N-(tert-Butoxycarbonyl)-N,O-isopropylidene-3-phenylisoserinyl]-10-deacetyl-10-O-(methylthio)thiocarbonyl-7-O-triethylsilylbaccatin III 10-Deacetyl-10-O-(methylthio)thiocarbonyl-7-O-triethylsilylbaccatin III was reacted with (4S,5R)-3-(tert-butoxycarbonyl)-2,2-dimethyl-4-phenyloxazoline-5-carboxylic acid in the same manner as in step 2 of Example 1 to yield the titled compound as a colorless oily substance.

$^1$H-NMR (CDCl$_3$/TMS) δ(ppm): 0.57(6H, m), 0.91(9H, t), 1.11(9H, br), 1.22(3H, s), 1.29(3H, s), 1.68(3H, s), 1.77(3H, s), 1.81(3H, s), 1.87(3H, s), 1.88(1H, m), 2.16(3H, s), 2.52(1H, m), 2.65(3H, s), 3.77(1H, d, J=7 Hz), 4.11(1H, d, J=8.5 Hz), 4.25(1H, d, J=8.5 Hz), 4.45(2H, m), 4.88(1H, d, J=8 Hz), 5.06(1H, br), 5.68(1H, d, J=7 Hz), 6.24(1H, t, J=8 Hz), 7.26(10H, s), 7.3–7.4(5H, m), 7.49(2H, t), 7.63(1H, t), 8.05(2H, d).

Step 2: 13-O-[(2R,3S)-N-(tert-Butoxycarbonyl)-N,O-isopropylidene-3-phenylisoserinyl]-10-deacetoxy-10-(2-methoxycarbonylethyl)-7-O-triethylsilylbaccatin III The compound obtained in the above Step 1 was reacted in the same manner as in Step 1 of Example 1 except for using methyl acrylate in place of acrylonitrile to yield the titled compound as a colorless amorphous solid.

¹H-NMR (CDCl₃/TMS) δ(ppm): 0.57(6H, m), 0.95(9H, t), 1.14(12H, br+s), 1.21(3H, s), 1.31(1H, m), 1.60(3H, s), 1.77(3H, s), 1.81(9H, s), 3.68(3H, s), 3.80(1H, m), 3.89(1H, d, J=7 Hz), 4.11(1H, d, J=8.5 Hz), 4.23(1H, d, J=8.5), 4.46(2H, m), 4.88(1H, m), 5.03(1H, br), 5.61(1H, d, J=7 Hz), 6.23(1H, t), 7.36(5H, m), 7.50(2H, t), 7.63(1H, t), 8.04(2H, m).

Step 3: 13-O-[(2R,3S)-3-(tert-Butoxycarbonylamino)-2-hydroxy-3-phenylpropionyl]-10-deacetoxy-10-(2-methoxycarbonylethyl)baccatin III The compound obtained in the above Step 2 was reacted in the same manner as in Step 3 of Example 1 to yield the titled compound as a colorless solid.

Melting Point: 130°–134° C.

¹H-NMR (CDCl₃/TMS) δ(ppm): 1.13(3H, s), 1.20(3H, s), 1.33(9H, s), 1.64(3H, s), 1.73(3H, s), 1.87(1H, m), 2.37(3H, s), 3.33(1H, br), 3.68(3H, s), 3.95(2H, m), 4.13(2H, m), 4.19(1H, d, J=8.5 Hz), 4.30(1H, d, J=8.5 Hz), 4.33(1H, m), 4.60(1H, m), 4.95(1H, d, J=9 Hz), 5.26(1H, br), 5.37(1H, m), 5.66(1H, d, J=7.5 Hz), 6.18(1H, t, J=9 Hz), 7.3–7.45(5H, m), 7.49(2H, t), 7.60(1H, t), 8.11(2H, d).

EXAMPLE 8

13-O-[(2R,3S)-3-(tert-Butoxycarbonylamino)-2-hydroxy-3-phenylpropionyl]-10-(2-carboxyethyl)-10-deacetoxybaccatin III

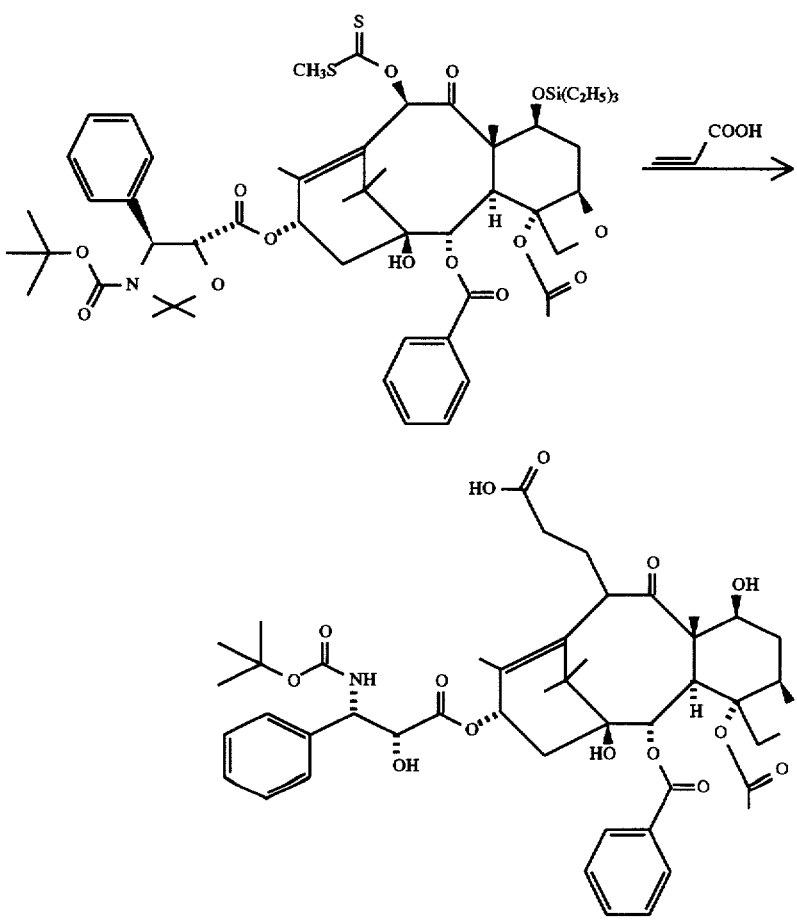

The compound obtained in Step 1 of Example 7 was reacted in the same manner as in Step 1 of Example 1 except for using acrylic acid in place of acrylonitrile to obtain a colorless amorphous solid. The resulting solid was reacted in the same manner as in Step 3 of Example 1 to yield the titled compound as colorless solid.

Melting Point: 148°–152° C.

¹H-NMR (CDCl₃/TMS) δ(ppm): 1.13(3H, s), 1.20(3H, s), 1.32(9H, s), 1.64(3H, s), 1.78(3H, s), 2.38(3H, br), 3.95(1H, d, J=7.5 Hz), 3.99(1H, m), 4.19(1H, d, J=8.5 Hz), 4.30(1H, d, J=8.5 Hz), 4.37(1H, dd, J=9 Hz, 6.5 Hz), 4.63(1H, br), 4.96(1H, d, J=9.5 Hz), 5.27(1H, br), 5.45(1H, m), 5.65(1H, d, J=7.5 Hz), 6.18(1H, br), 7.3–7.45(5H, m), 7.50(2H, t), 7.61(1H, t), 8.10(2H, d).

EXAMPLE 9

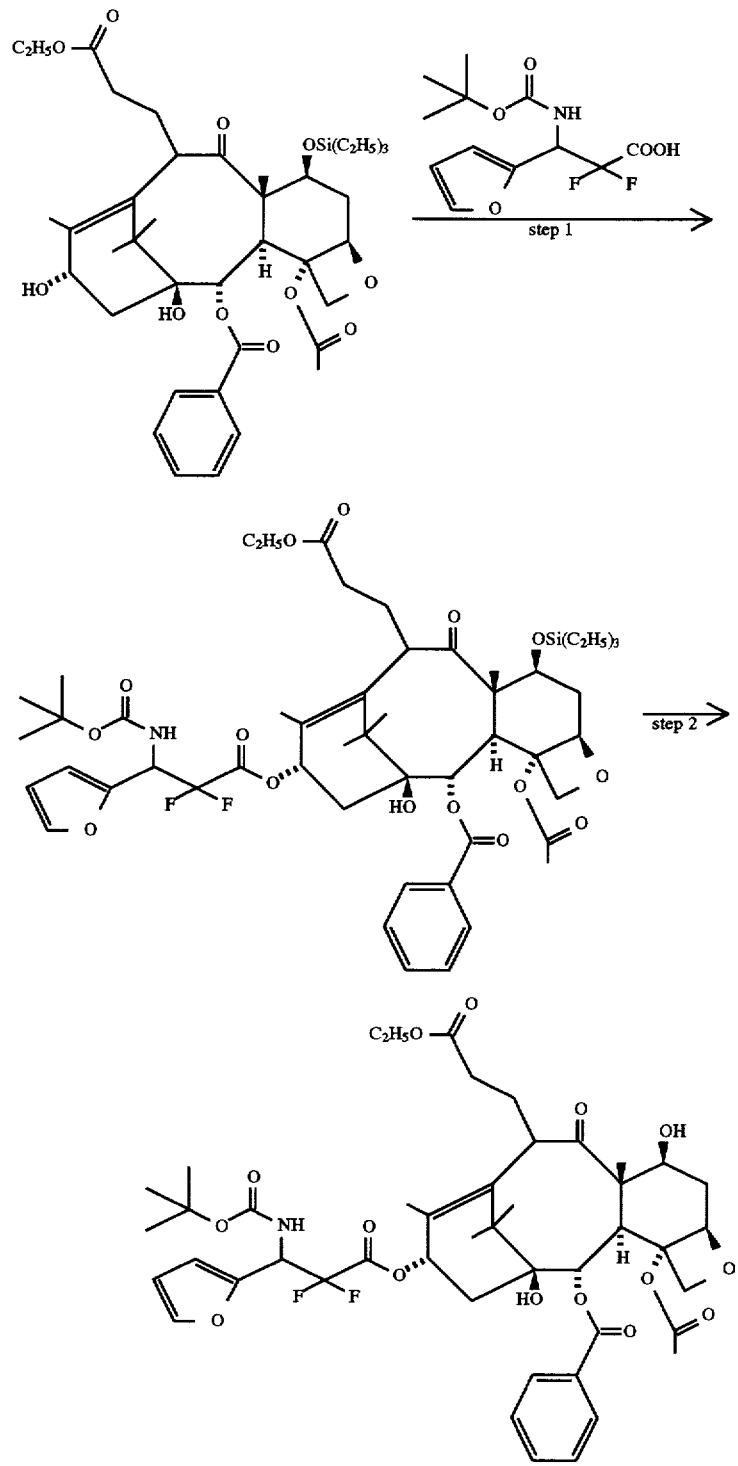

Step 1: 13-O-[3-(tert-Butoxycarbonylamino)-2,2-difluoro-3-(2-furyl)propionyl]-10-deacetoxy-10-(2-ethoxycarbonylethyl)-7-O-triethylsilylbaccatin III 67 mg of the compound obtained in Step 1 of Example 2 and 218 mg of 3-(tert-butoxycarbonylamino)-2,2-difluoro-3-(2-furyl)propionic acid were suspended in 2 ml of dried toluene, and 123 mg of di-2-pyridylcarbonate and 20 mg of 4-methylaminopyridine were added thereto, followed by stirring for 14 hours while heating at 70° C. The solvent was evaporated under reduced pressure, the resulting residue was purified by silica gel thin layer chromatography (a developing solvent; chloroform:acetone=95:5 (v/v)) to yield 77 mg of the titled compound as a colorless solid.

Step 2: 13-O-[3-(tert-Butoxycarbonylamino)-2,2-difluoro-3-(2-furyl)propionyl]-10-deacetoxy-10-(2-ethoxycarbonylethyl)baccatin III 75 mg of the compound obtained in the above Step 1 was dissolved in 10 ml of a 80% aqueous acetic acid solution, followed by stirring for 4 hours while heating at 70° C. After evaporation of the solvent under reduced pressure, an aqueous solution of sodium bicarbonate was added thereto, and the mixture was extracted with ethyl acetate. The organic layer was washed with a saturated aqueous solution of sodium chloride, dried over anhydrous magnesium sulfate, and the solvent was evaporated under reduced pressure. The resulting residue was purified by silica gel thin-layer chromatography (a developing solvent; chloroform:methanol= 97:3 (v/v)) to yield the titled compound as a mixture of isomers at the 3'-position. The isomers was separated by high performance liquid chromatography (the column used: a silica gel type normal phase column, a developing solvent; hexane:ethyl acetate=3:1 (v/v)) to yield 12 mg of the isomer A of the titled compound which was eluted earlier and 13 mg of the isomer B of the titled compound which was eluted later, each as a white powder.

Isomer A

Melting Point: 118°–120° C.

$^1$H-NMR (CDCl$_3$/TMS) δ(ppm): 1.13(3H, s), 1.18(3H, s), 1.27(3H, t, J=7.5 Hz), 1.42(9H, s), 1.64(3H, s), 1.72(3H, s), 1.86(1H, m), 2.31(3H, s), 3.95(2H, m), 4.15(3H, m), 4.30 (1H, d, J=9 Hz), 4.45(1H, m), 4.96(1H, d, J=9 Hz), 5.35(1H, m), 5.63(1H, m), 5.66(1H, d, J=7 Hz), 6.18(1H, m), 6.41 (2H, m), 7.44(1H, s), 7.49(2H, t), 7.62(1H, t), 8.10(2H, d).

Isomer B

Melting Point: 103°–105° C.

$^1$H-NMR (CDCl$_3$/TMS) δ(ppm): 1.13(3H, s), 1.18(3H, s), 1.27(3H, m), 1.45(9H, s), 1.64(3H, s), 1.72(3H, s), 1.86(1H, m), 2.24(3H, s), 3.95(2H, m), 4.14(3H, m), 4.30(1H, d, J=8.5 Hz), 4.40(1H, m), 4.96(1H, d, J=8.5 Hz), 5.37(1H, m), 5.62(1H, m), 5.66(1H, d, J=7 Hz), 6.13(1H, m), 6.41(2H, m), 7.42(1H, s), 7.50(2H, t), 7.62(1H, t), 8.08(2H, d).

EXAMPLE 10

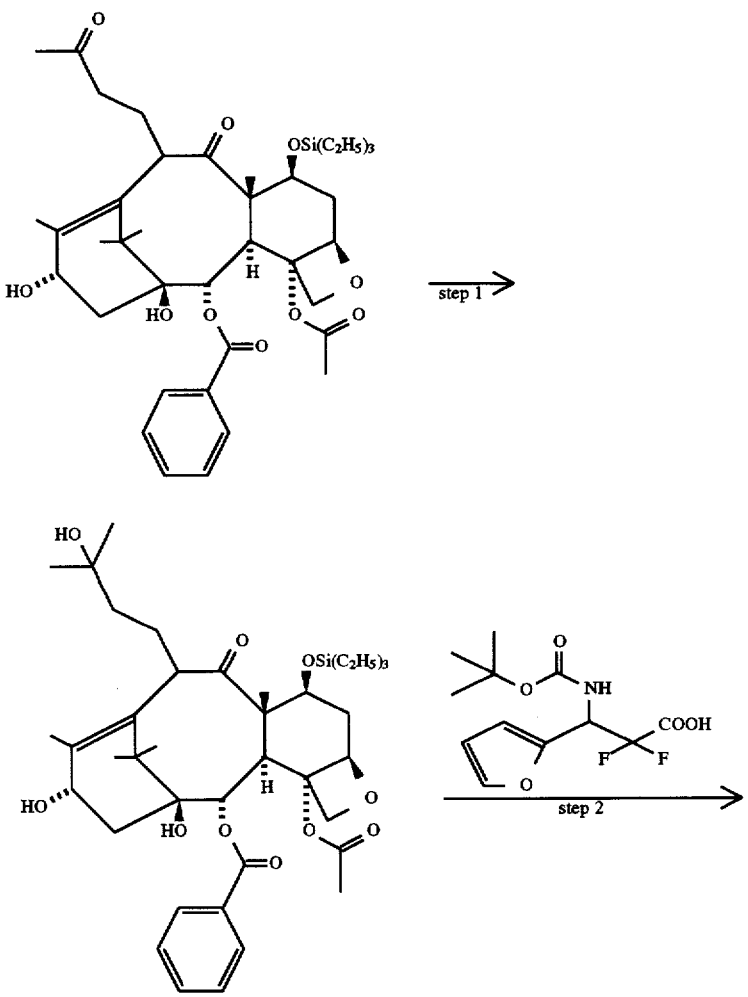

-continued

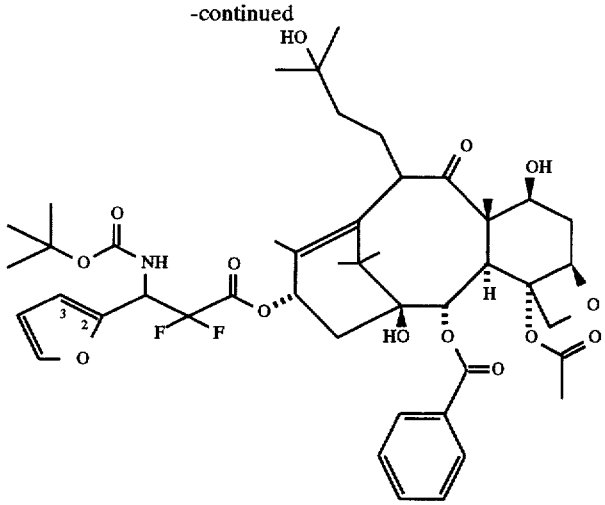

Step 1: 10-Deacetoxy-10-(3-hydroxy-3-methylbutyl)-7-O-triethylsilylbaccatin III

In a nitrogen gas atmosphere, 164 mg of the compound obtained in Step 1 of Example 5 was dissolved in 5 ml of dried tetrahydrofuran, and the solution was cooled to −78° C. in a dry ice-acetone bath, followed by adding dropwise 100 μl of a hexane solution of methyl lithium (at a concentration of 1.15M). After stirring at that temperature for 30 minutes, a 10% (w/v) aqueous solution of ammonium chloride was added thereto, followed by allowing to warm to room temperature. The mixture was extracted with chloroform, and the organic layer was dried over anhydrous sodium sulfate. The solvent was evaporated under reduced pressure, and the resulting residue was purified by silica gel thin layer chromatography (a developing solvent; chloroform:methanol=97:3 (v/v)) to yield 171 mg of the titled compound as a colorless oily substance.

$^1$H-NMR (CDCl$_3$/TMS) δ(ppm): 0.57(6H, m), 0.96(9H, t, J=8 Hz), 1.06(3H, s), 1.13(3H, s), 1.25(6H, s), 1.49(2H, m), 1.63(3H, s), 1.89(1H, m), 1.97(3H, s), 2.29(3H, s), 2.49(1H, m), 3.78(1H, dd, J=4.5 Hz, 9.5 Hz), 4.06(1H, d, J=7 Hz), 4.17(1H, d, J=8 Hz), 4.30(1H, d, J=8 Hz), 4.55(1H, dd, J=10.5 Hz, 6.5 Hz), 4.85(1H, m), 4.97(1H, d, J=9.5 Hz), 5.60(1H, d, J=7 Hz), 7.47(2H, t), 7.60(1H, t), 8.11(2H, d).

Step 2: 13-O-[3-tert-Butoxycarbonylamino)-2,2-difluoro-3-(2-furyl)propionyl]-10-deacetoxy-10-(3-hydroxy-3-methylbutyl)baccatin III The compound obtained in the above Step 1 was reacted with 3-(tert-butoxycarbonylamino)-2,2-difluoro-3-(2-furyl)propionic acid in the same manner as in Step 1 of Example 9, and then a de-protection reaction was carried out in the same manner as in Step 2 of Example 9. The reaction mixture was purified by silica gel thin layer chromatography (a developing solvent; chloroform:methanol=96:4 (v/v)) to yield the titled compound as a mixture of isomers at the 3'-position. The isomers was separated by high performance liquid chromatography (a column used; ODS type reverse phase column, a developing solvent; methanol:water=62:38 (v/v)) to yield the isomer A of the titled compound which was eluted earlier and the isomer B of the titled compound which was eluted later.

Isomer A $^1$H-NMR (CDCl$_3$/TMS) δ(ppm): 1.14(3H, s), 1.19(3H, s), 1.24(3H, s), 1.26(3H, s), 1.45(9H, s), 1.64(3H, s), 1.79(3H, s), 1.82(1H, m), 2.25(3H, s), 2.53(1H, m), 3.98(1H, d, J=7.5 Hz), 4.07(1H, m), 4.17(1H, d, J=9 Hz), 4.30(1H, d, J=9 Hz), 4.37(1H, dd, J=11.5 Hz, 7 Hz), 4.96(1H, br-d, J=8 Hz), 5.36(1H, br-d, J=8.5 Hz), 5.6(1H, m), 5.67(1H, d, J=7.5 Hz), 6.17(1H, br-t, J=8.5 Hz), 6.39(1H, dd, J=3.5 Hz, 2 Hz), 6.43(1H, d, J=3.5 Hz), 7.42(1H, J=2 Hz), 7.50(2H, t), 7.62(1H, t), 8.08(2H, d).

Isomer B $^1$H-NMR (CDCl$_3$/TMS) δ(ppm): 1.14(3H, s), 1.19(3H, s), 1.25(3H, s), 1.26(3H, s), 1.42(9H, s), 1.64(3H, s), 1.79(3H, s), 1.83(1H, m), 2.30(3H, s), 2.53(1H, m), 3.98(1H, d, J=7 Hz), 4.08(1H, dd, J=8 Hz, 4 Hz), 4.17(1H, d, J=8.5 Hz), 4.30(1H, d, J=8.5 Hz), 4.37(1H, dd, J=11 Hz, 6.5 Hz), 4.97(1H, d, J=8.5 Hz), 5.37(1H, d, J=10 Hz), 5.6(1H, m), 5.66(1H, d, J=7 Hz), 6.21(1H, br-t, J=8.5 Hz), 6.40(1H, dd, J=3 Hz, 1.5 Hz), 6.43(1H, d, J=3 Hz), 7.45(1H, J=1.5 Hz), 7.50(2H, t), 7.62(1H, t), 8.10(2H, d).

EXAMPLE 11
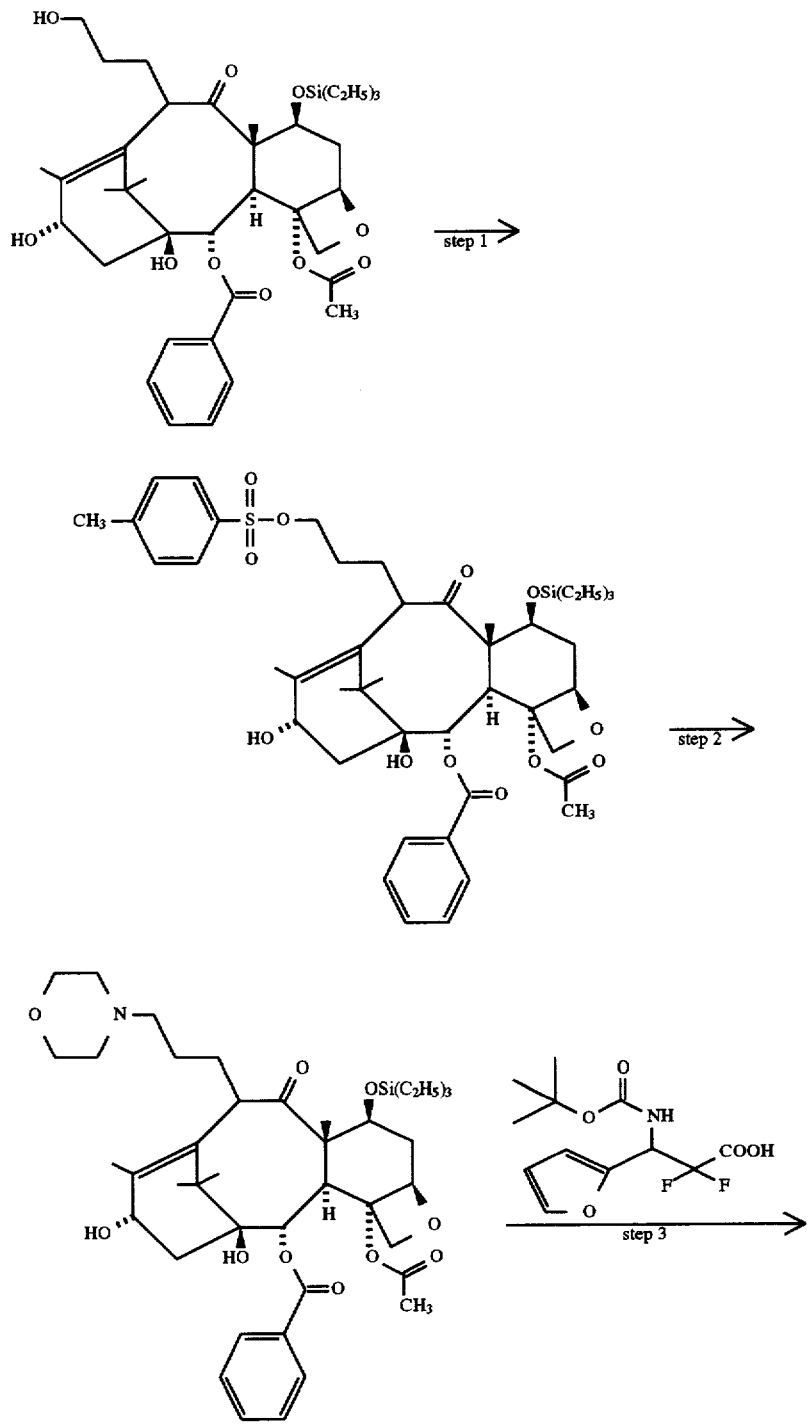

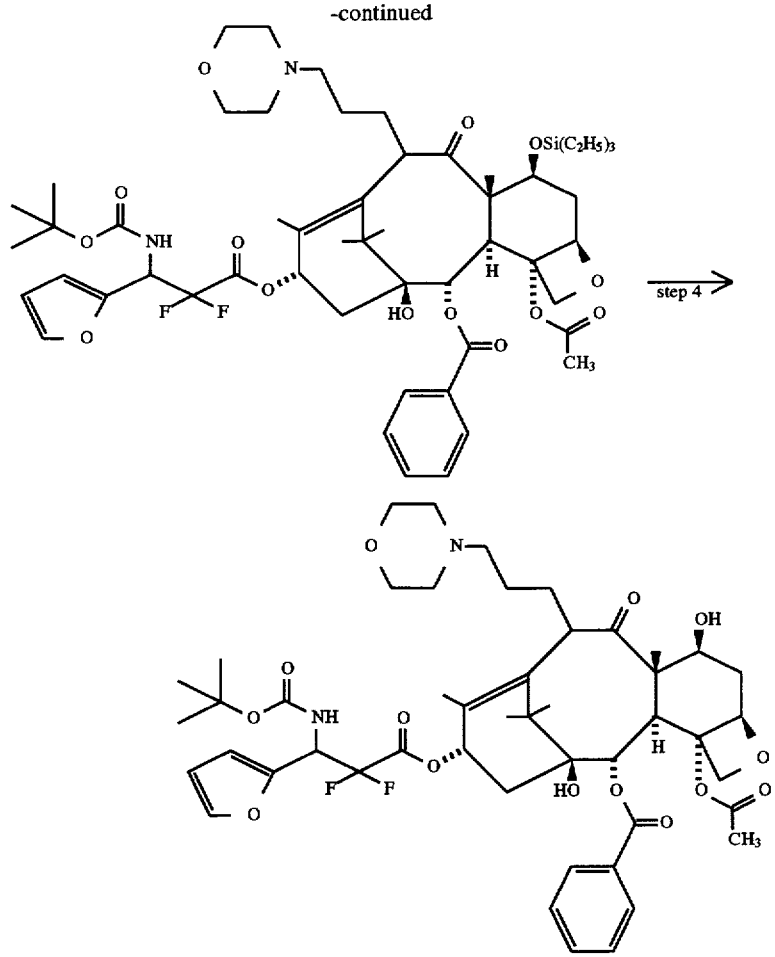

Step 1: 10-Deacetoxy-10-(3-p-toluenesulfonylpropyl)-7-O-triethylsilylbaccatin III 400 mg of 10-deacetoxy-10-(3-hydroxypropyl)-7-O-triethylsilylbaccatin III was dissolved in 10 ml of dichloromethane, and 245 mg of p-toluenesulfonyl chloride, 130 mg of triethylamine and a catalytic amount of 4-methylaminopyridine were added thereto at 0° C., followed by stirring overnight. Ice water was added to the reaction solution, and the mixture was extracted with chloroform. The extract was washed with a saturated aqueous sodium chloride solution, dried over anhydrous magnesium sulfate, and the solvent was evaporated under reduced pressure. The resulting residue was purified by silica gel column chromatography (a developing solvent; chloroform:methanol=97:3 (v/v)) to yield 360 mg of the titled compound.

$^1$H-NMR (CDCl$_3$/TMS) δ(ppm): 0.52(6H, m), 0.92(9H, t, J=8 Hz), 1.00(3H, s), 1.04(3H, s), 1.60(3H, s), 1.92(3H, s), 2.28(3H, s), 2.46(3H, s), 3.73–3.77(1H, m), 4.00–4.10(3H, m), 4.15(1H, d, J=8 Hz), 4.29(1H, d, J=8 Hz), 4.49–4.55(1H, m), 4.80–4.88(1H, br), 4.95(1H, d, J=10 Hz), 5.57(1H, d, J=7 Hz), 7.36(2H, d, J=8 Hz), 7.47(2H, t, J=7 Hz), 7.60(1H, t, J=8 Hz), 7.80(2H, d, J=7.5 Hz), 8.10(2H, d, J=7.5 Hz).

Step 2: 10-Deacetoxy-10-(3-morpholinopropyl)-7-O-triethylsilylbaccatin III 100 mg of the compound obtained in the above Step 1 was dissolved in 2 ml of methanol, and 51 mg of morpholine was added thereto, followed by heating under refluxing for 5 hours. The reaction solution was evaporated under reduced pressure, and the resulting reside was purified by silica gel column chromatography (a developing solvent; chloroform:methanol=9:1 (v/v)) to yield 74 mg of the titled compound.

$^1$H-NMR (CDCl$_3$/TMS) δ(ppm): 0.50–0.61(6H, m), 0.95 (9H, t, J=8 Hz), 1.04(3H, s), 1.11(3H, s), 1.45–2.51(23H, m, Incl s at 1.62, 1.96, 2.28 each 3H), 3.72(4H, t, J=4.5 Hz), 3.81(1H, dd, J=4.5 Hz, 9 Hz), 4.05(1H, d, J=7 Hz), 4.16(1H, d, J=8 Hz), 4.29(1H, d, J=8 Hz), 4.54(1H, dd, J=7 Hz, 11 Hz), 4.80–4.85(1H, m), 4.96(1H, d, J=8 Hz), 5.59(1H, d, J=7 Hz), 7.47(2H, t, J=8 Hz), 7.59(1H, t, J=8 Hz), 8.10(2H, d, J=7 Hz).

Step 3: 13-O-[3-(tert-Butoxycarbonylamino)-2,2-difluoro-3-(2-furyl)propionyl]-10-deacetoxy-10-(3-morpholinopropyl)-7-O-triethylsilylbaccatin III 74 mg of the compound obtained in the above Step 2, 83 mg of di-2-pyridylcarbonate and 112 mg of 3-(tert-butoxycarbonylamino)-2,2-difluoro-3-(2-furyl)propionic acid were dissolved in 2 ml of toluene. 12 mg of 4-dimethylaminopyridine was added thereto, and the mixture was stirred for 15 minutes at room temperature and then stirred for 70 hours at 70° C. After adding a saturated aqueous sodium bicarbonate solution, the mixture was extracted with ethyl acetate. The extract was washed with a saturated aqueous sodium chloride solution, dried over anhydrous magnesium sulfate, and the solvent was evaporated under reduced pressure. The resulting residue was purified by silica gel column chromatography (a developing solvent; chloroform:methanol=95:5 (v/v)) to yield 20 mg of the titled compound.

¹H-NMR (CDCl₃/TMS) δ(ppm): 0.49–0.61(6H, m), 0.95 (9H, t, J=8 Hz), 1.14(3H, s), 1.18(3H, s), 1.44(9H, s), 1.62(3H, s), 1.71–1.94(3H, m), 2.04(3H, s), 2.04–2.50(11H, m), 2.25(3H, s), 3.73(4H, br-s), 3.96(1H, d, J=7 Hz), 4.15 (1H, d, J=8 Hz), 4.29(1H, d, J=8 Hz), 4.51(1H, dd, J=6 Hz, 11 Hz), 4.93(1H, d, J=8 Hz), 5.37–5.42(1H, m), 5.58–5.62 (1H, m), 5.64(1H, d, J=7 Hz), 6.15–6.24(1H, m), 6.39–6.45 (2H, m), 7.43 and 7.44(total 1H, each s), 7.49(2H, t, J=7 Hz), 7.59–7.64(1H, m), 8.06–8.10(2H, m).

Step 4: 13-O-[3-(tert-Butoxycarbonylamino)-2,2-difluoro-3-(2-furyl)propionyl]-10-deacetoxy-10-(3-morpholinopropyl)baccatin III 20 mg of the compound obtained in the above Step 3 was dissolved in 5 ml of acetonitrile, and 20 μml of concentrated hydrochloric acid was added dropwise thereto at –10° C. After stirring at that temperature for one hour, a saturated aqueous sodium bicarbonate solution was added thereto, and the mixture was extracted with ethyl acetate. The extract was washed with a saturated aqueous sodium chloride solution, dried over anhydrous magnesium sulfate, and the solvent was evaporated under reduced pressure. The resulting residue was purified by silica gel column chromatography (a developing solvent; chloroform:methanol=93:7 (v/v)) to yield 13 mg of the titled compound.

¹H-NMR (CDCl₃/TMS) δ(ppm): 1.12(3H, s), 1.17(3H, s), 1.42 and 1.45(total 9H, each s), 1.63(3H, s), 1.70–1.88(7H, m), 2.25(3H,.s), 2.19–2.57(7H, m), 3.72(4H, t, J=4 Hz), 3.79–3.82(1H, m), 3.99(1H, d, J=7 Hz), 4.17(1H, d, J=8 Hz), 4.30(1H, d, J=8 Hz), 4.36(1H, dd, J=7 Hz, 11 Hz), 4.96(1H, d, J=10 Hz), 5.34–5.40(1H, m), 5.60–5.64(1H, m), 5.66(1H, d, J=7 Hz), 6.11–6.21(1H, m), 6.39–6.44(2H, m), 7.43–7.45 (1H, m), 7.50(2H, t, J=7 Hz), 7.60–7.65(1H, m), 8.07–8.11 (2H, m).

MS-FAB: 930(MH⁺)

EXAMPLE 12

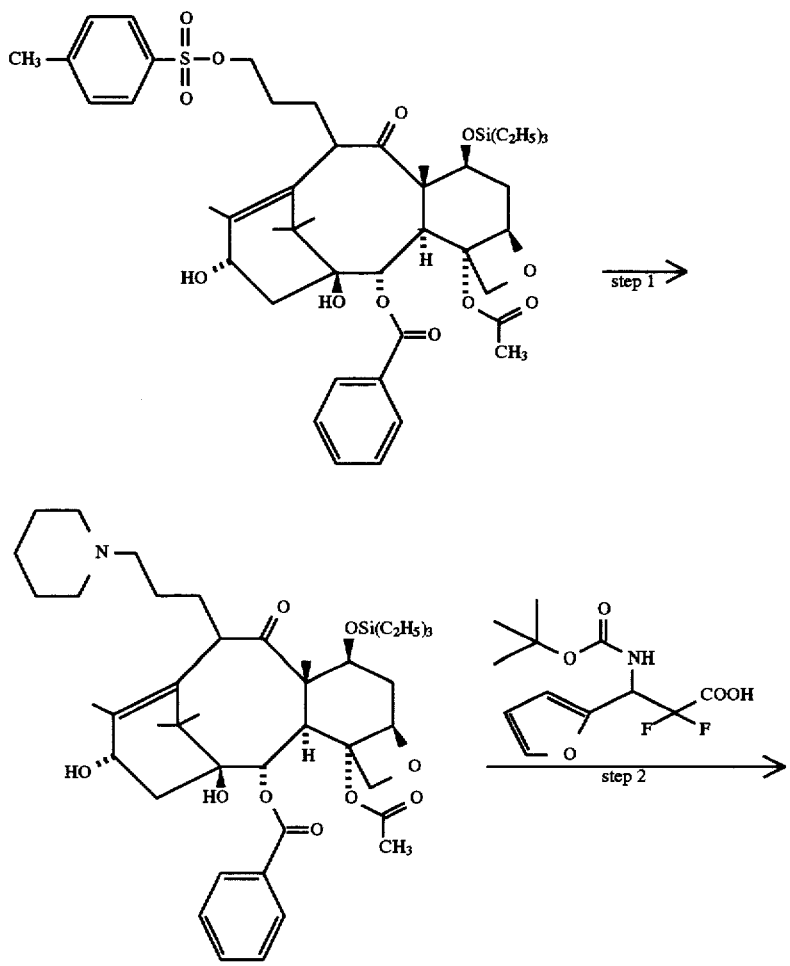

-continued

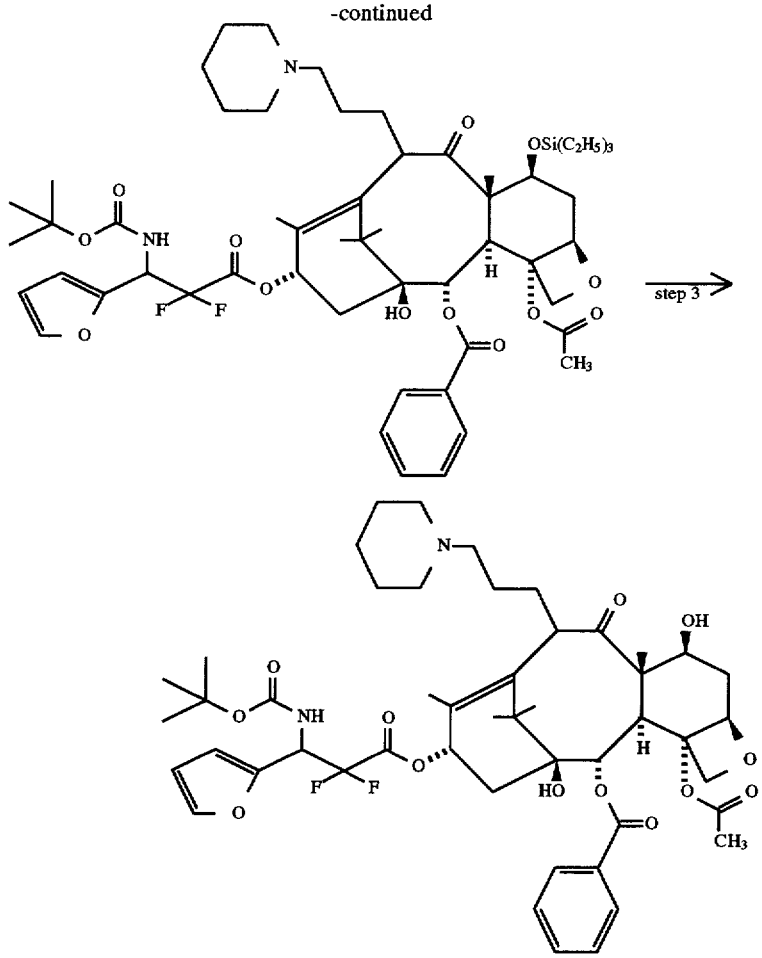

Step 1: 10-Deacetoxy-10-(3-piperidinopropyl)-7-O-triethylsilylbaccatin III

The compound obtained in Step 1 of Example 11 was reacted in the same manner as in Step 2 of Example 11 except for using piperidine in place of morpholine to yield the titled compound as a white amorphous solid.

$^1$H-NMR (CDCl$_3$/TMS) δ(ppm): 0.49–0.61(6H, m), 0.94 (9H, t, J=8 Hz), 1.04(3H, s), 1.08(3H, s), 1.49–1.96(11H, m), 1.61(3H, s), 1.96(3H, s), 2.00–2.32(2H, m), 2.29(3H, s), 2.45–2.53(1H, m), 2.55–2.86(6H, m), 3.79–3.83(1H, m), 4.04(1H, d, J=7 Hz), 4.16(1H, d, J=8 Hz), 4.28(1H, d, J=8 Hz), 4.54(1H, dd, J=6 Hz, 11 Hz), 4.82(1H, br-t, J=8 Hz), 4.97(1H, d, J=8 Hz), 5.58(1H, d, J=7 Hz), 7.49(2H, t, J=8 Hz), 7.59(1H, t, J=7 Hz), 8.10(2H, d, J=7 Hz).

Step 2: 13-O-[3-tert-Butoxycarbonylamino)-2,2-difluoro-3-(2-furyl)propionyl]-10-deacetoxy-10-(3-piperidinopropyl)-7-O-triethylsilylbaccatin III The compound obtained in the above Step 1 was reacted in the same manner as in Step 3 of Example 11 to yield the titled compound as a white amorphous material.

$^1$H-NMR (CDCl$_3$/TMS) δ(ppm): 0.49–0.60(6H, m), 0.94 (9H, t, J=8 Hz), 1.13(3H, s), 1.17(3H, s), 1.39–2.15(11H, m), 1.42 and 1.45(total 9H, each s), 1.62(3H, s), 1.76 and 1.79(total 3H, each s), 2.15–2.30(1H, m), 2.25(3H, s), 2.30–2.60(8H, m), 3.72–3.80(1H, m), 3.95(1H, d, J=7 Hz), 4.15(1H, d, J=8 Hz), 4.29(1H, d, J=8 Hz), 4.49–4.53(1H, m), 4.93(1H, d, J=8 Hz), 5.37–5.42(1H, m), 5.56–5.64(1H, m), 5.64(1H, d, J=7 Hz), 6.13–6.22(1H, m), 6.39–6.46(2H, m), 7.43 and 7.45(total 1H, each s-d), 7.49(2H, t, J=8 Hz), 7.59–7.65(1H, m), 8.06–8.11(2H, m).

Step 3: 13-O-[3-tert-Butoxycarbonylamino)-2,2-difluoro-3-(2-furyl)propionyl]-10-deacetoxy-10-(3-piperidinopropyl)baccatin III The compound obtained in the above Step 2 was reacted in the same manner as in Step 4 of Example 11 to yield the titled compound as a white amorphous material.

$^1$H-NMR (CDCl$_3$/TMS) δ(ppm): 1.07(3H, s), 1.17(3H, s), 1.43 and 1.46(total 9H, each s), 1.66(3H, s), 1.81(3H, s), 2.24(3H, s), 3.90–3.93(1H, m), 3.97–4.01(1H, m), 4.15(1H, d, J=8 Hz), 4.29(1H, d, J=8 Hz), 4.48–4.53(1H, m), 5.35–5.40(1H, m), 5.57–5.70(1H, m), 5.62(1H, d, J=7 Hz), 5.60–5.65(1H, m), 6.09–6.21(1H, m), 6.41(2H, m), 7.44 and 7.46(total 1H, each s-d), 7.49(2H, t, J=8 Hz), 7.59–7.64(1H, m)8.07–8.11(2H, m).

MS-FAB: 928(MH$^+$)

EXAMPLE 13
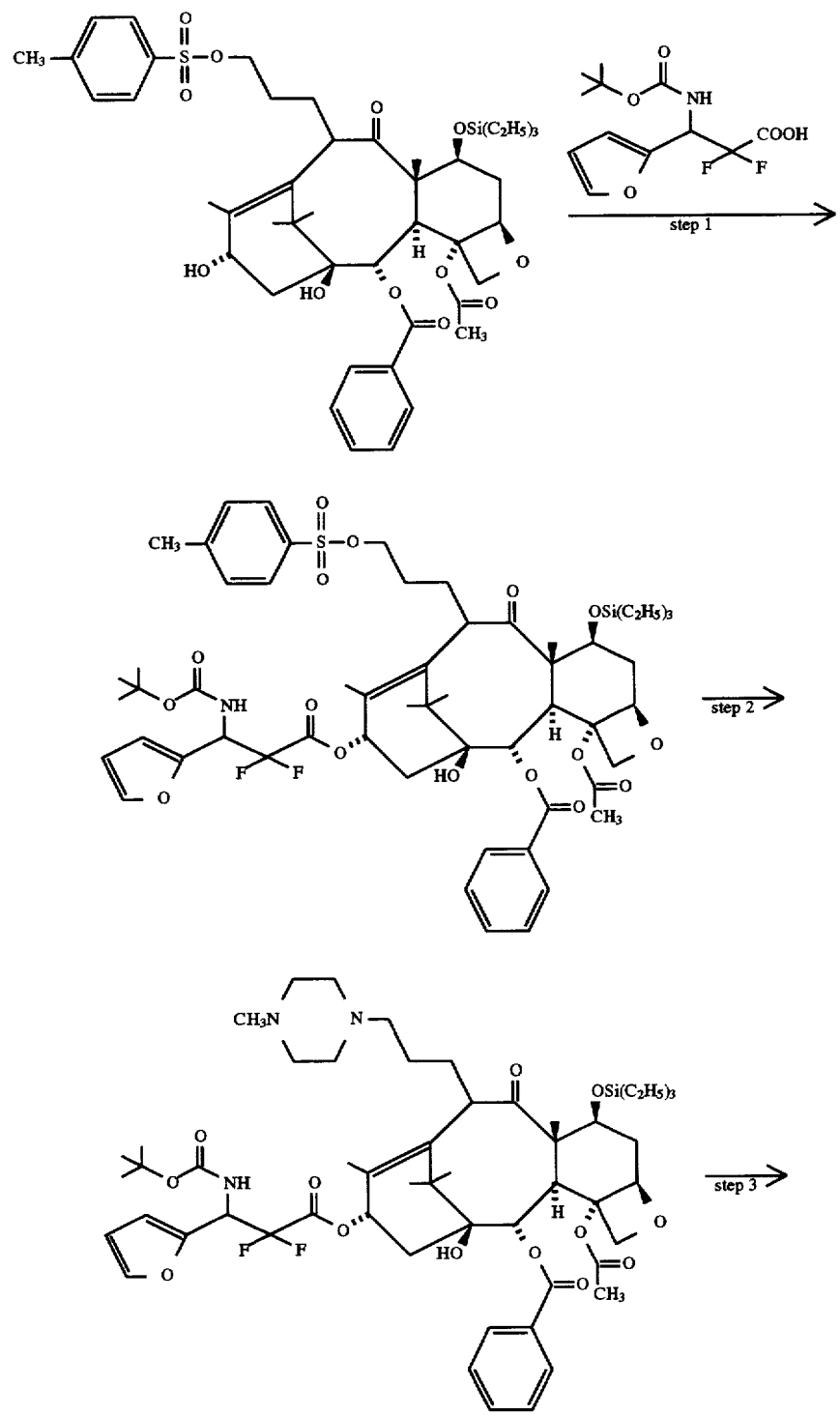

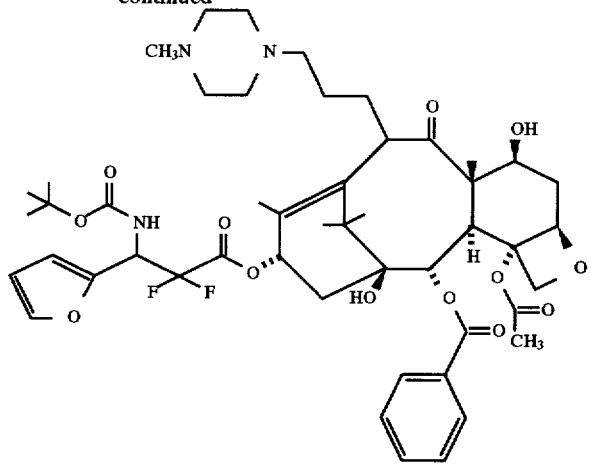

Step 1: 13-O-[3-tert-Butoxycarbonylamino)-2,2-difluoro-3-(2-furyl)propionyl]-10-deacetoxy-10-[3-(p-toluenesulfonyl)propyl]-7-O-triethylsilylbaccatin III The compound obtained in Step 1 of Example 11 was reacted in the same manner as in Step 3 of Example 11 to yield the titled compound as a white amorphous solid.

¹H-NMR (CDCl₃/TMS) δ(ppm): 0.45–0.55(6H, m), 0.92 (9H, t, J=8 Hz), 1.07(3H, s), 1.12(3H, s), 1.35–1.90(5H, m), 1.42 and 1.45(total 9H, each s), 1.61(3H, s), 1.72 and 1.74(total 3H, each s), 2.00–2.10(1H, m), 2.10–2.40(1H, m), 2.25(3H, s), 2.38–2.50(1H, m), 2.46(3H, s), 3.68–3.72(1H, m), 3.91(1H, d, J=7 Hz), 4.02–4.09(2H, m), 4.13(1H, d, J=8 Hz), 4.28(1H, d, J=8 Hz), 4.48(1H, dd, J=6 Hz, 11 Hz), 4.92(1H, d, J=9 Hz), 5.35–5.40(1H, m), 5.60–5.65(1H, m), 5.62(1H, d, J=7 Hz), 6.10–6.20(1H, m), 6.40–6.45(2H, m), 7.36(2H, d, J=8 Hz), 7.44 and 7.46(total 1H, each s), 7.49(2H, t, J=8 Hz), 7.58–7.64(1H, m), 7.79(2H, d, J=8 Hz), 8.05–8.10(2H, m).

Step 2: 13-O-[3-tert-Butoxycarbonylamino)-2,2-difluoro-3-(2-furyl)propionyl]-10-deacetoxy-10-[3-(4-methylpiperazin-1-yl)propyl]-7-O-triethylsilylbaccatin III The compound obtained in the above Step 1 was reacted in the same manner as in Step 2 of Example 11 except for using N-methylpiperazine in place of morpholine to yield the titled compound as a white amorphous material.

¹H-NMR (CDCl₃/TMS) δ(ppm): 0.50–0.60(6H, m), 0.94 (9H, t, J=8 Hz), 1.14(3H, s), 1.18(3H, s), 1.42 and 1.45(total 9H, each s), 1.62(3H, s), 1.76(3H, s), 2.25(3H, s), 2.34(3H, s), 3.73–3.79(1H, m), 3.95(1H, d, J=7 Hz), 4.15(1H, d, J=8 Hz), 4.29(1H, d, J=8 Hz), 4.48–4.52(1H, m), 4.93(1H, d, J=9 Hz), 5.33–5.39(1H, m), 5.57–5.63(1H, m), 5.64(1H, d, J=7 Hz), 6.17 and 6.21(total 1H, each t, J=8 Hz), 6.39–6.45(2H, m), 7.43 and 7.44(total 1H, each s), 7.45(2H, t, J=8 Hz), 7.59–7.64(1H, m), 8.06–8.11(2H, m).

Step 3: 13-O-[3-tert-Butoxycarbonylamino)-2,2-difluoro-3-(2-furyl)propionyl]-10-deacetoxy-10-[3-(4-methylpiperazin-1-yl)propyl]baccatin III The compound obtained in the above Step 2 was reacted in the same manner as in Step 4 of Example 11 to yield the titled compound as a white amorphous material.

¹H-NMR (CDCl₃/TMS) δ(ppm): 1.11 and 1.17(total 3H, each s), 1.25(3H, s), 1.42 and 1.45(total 9H, each s), 1.64(3H, s), 2.04(3H, s), 2.20–2.32(1H, m), 2.25(3H, s), 2.30(3H, s), 3.80(1H, m), 3.98(1H, m), 4.17(1H, d, J=8 Hz), 4.30(1H, d, J=8 Hz), 4.35(1H, m), 4.96(1H, d, J=8 Hz), 5.30–5.40(1H, m), 5.61(1H, m), 5.65(1H, d, J=7 Hz), 6.10–6.20(1H, m), 6.34–6.43(2H, m), 7.38–7.50(3H, m), 7.57–7.65(1H, m), 8.04–8.11(2H, m).

MS-FAB: 943(MH⁺)

EXAMPLE 14

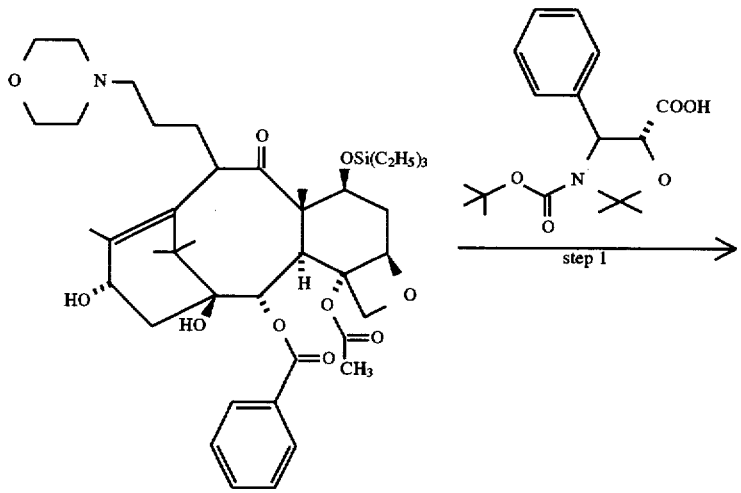

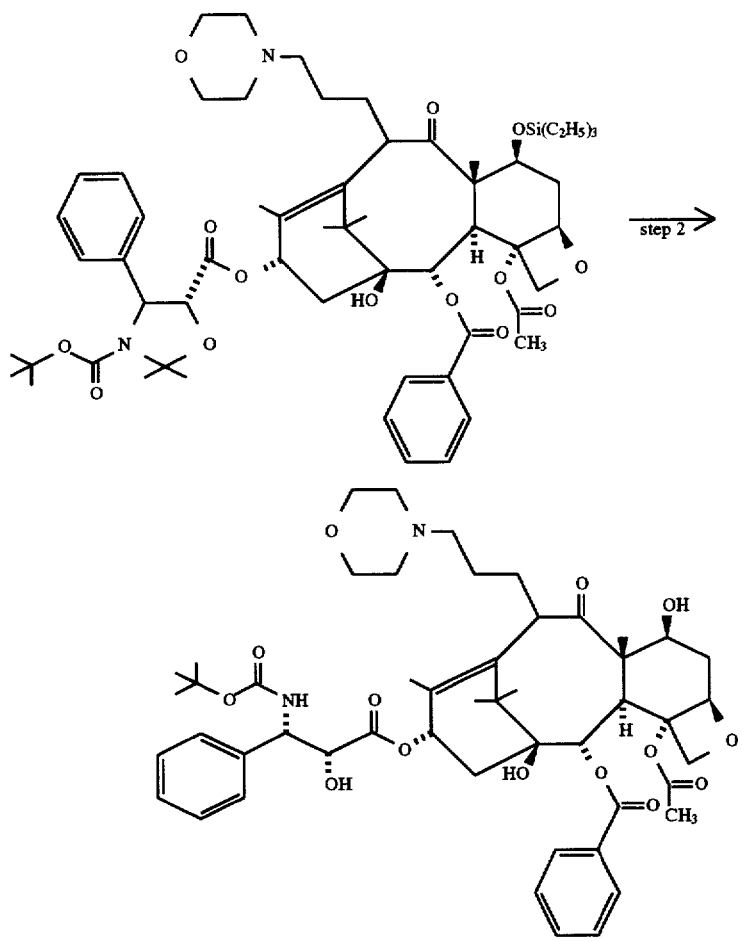

Step 1: 13-O-[(2R,3S)-N-(tert-Butoxycarbonyl)-N,O-isopropylidene-3-phenylisoserinyl]-10-deacetoxy-10-[3-morpholinopropyl)-7-O-triethylsilylbaccatin III 33 mg of the compound obtained in Step 2 of Example 11 and 27 mg of (2R,3S)-N-(tert-butoxycarbonyl)-2,3-N,O-isopropylidene-3-phenylisoserine were dissolved in 2 ml of toluene, followed by cooling to 0° C. Then, 18 mg of di-2-pyridylcarbonate was added thereto. After stirring for 15 minutes, 5 mg of 4-dimethylaminopyridine was added thereto, followed by stirring at 70° C. overnight. After cooling, the mixture was extracted with ethyl acetate. The extract was washed with a saturated aqueous sodium chloride solution, dried over anhydrous magnesium sulfate, and the solvent was evaporated under reduced pressure. The resulting residue was purified by silica gel thin layer chromatography (a developing solvent; chloroform:methanol= 95:5 (v/v)) to yield 10 mg of the titled compound.

$^1$H-NMR (CDCl$_3$/TMS) δ(ppm): 0.48–0.59(6H, m), 0.93 (9H, t, J=8 Hz), 1.05–1.50(5H, m), 1.13(3H, s), 1.20(3H, s), 1.59(3H, s), 1.67(9H, s), 1.77–1.98(2H, m), 1.77(3H, s), 1.79(3H, s), 1.82(3H, s), 2.08–2.16(3H, m), 2.30–2.48(5H, m), 3.70–3.80(5H, m), 3.92(1H, d, J=7 Hz), 4.06(1H, br-d, J=7 Hz), 4.11(1H, d, J=8 Hz), 4.23(1H, d, J=8 Hz), 4.44–4.50(1H, m), 4.47(1H, m), 4.88(1H, d, J=8 Hz), 5.04 (1H, br), 5.62(1H, d, J=7 Hz), 6.24(1H, br-t, J=8 Hz), 7.30–7.41(5H, m), 7.50(2H, t, J=7 Hz), 7.63(1H, t, J=7 Hz), 8.05(2H, d, J=7 Hz).

Step 2: 13-O-[(2R,3S)-3-(tert-Butoxycarbonylamino)-2-hydroxy-3-phenylpropionyl]-10-deacetoxy-10-(3-morpholinopropyl)baccatin III 10 mg of the compound obtained in the above Step 1 was dissolved in 2 ml of formic acid and reacted for 30 minutes at room temperature. The reaction solution was concentrated under reduced pressure, and the residue was diluted with chloroform, washed with a saturated aqueous sodium bicarbonate solution, dried over anhydrous sodium sulfate, and the solvent was evaporated under reduced pressure. The residue was dissolved in 2 ml of tetrahydrofuran, and 15 mg of di-tert-butyl dicarbonate was added thereto, followed by stirring overnight at room temperature. After concentration, the resulting residue was purified by silica gel thin layer chromatography (a developing solvent; chloroform:methanol=95:5 (v/v)) to yield 5 mg of the titled compound.

$^1$H-NMR (CDCl$_3$/TMS) δ(ppm): 1.13(3H, s), 1.20(3H, s), 1.58(9H, s), 1.64(3H, s), 1.68(3H, s), 1.78(3H, s), 3.65–3.75 (4H, m), 3.80–3.83(1H, m), 4.01(1H, d, J=7 Hz), 4.20(1H, d, J=8 Hz), 4.30(1H, d, J=8 Hz), 4.30–4.36(1H, m), 4.96(1H, d, J=8 Hz), 5.22–5.30(1H, m), 5.34–5.37(1H, m), 5.67(1H, d, J=8 Hz), 6.15–6.21(1H, m), 7.30–7.42(5H, m), 7.50(2H, t, J=8 Hz), 7.61(1H, m), 8.12(2H, d, J=7 Hz).

MS-FAB: 920(MH$^+$)

EXAMPLE 15
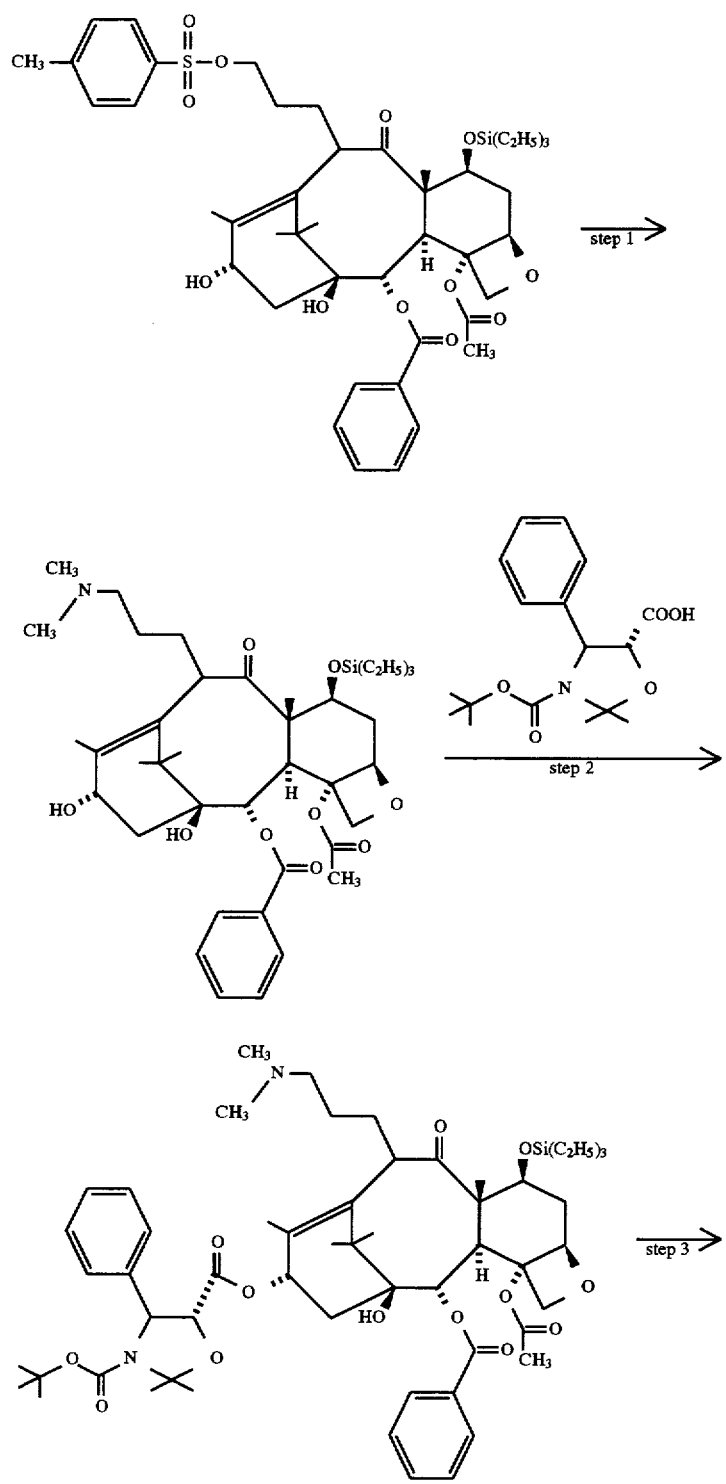

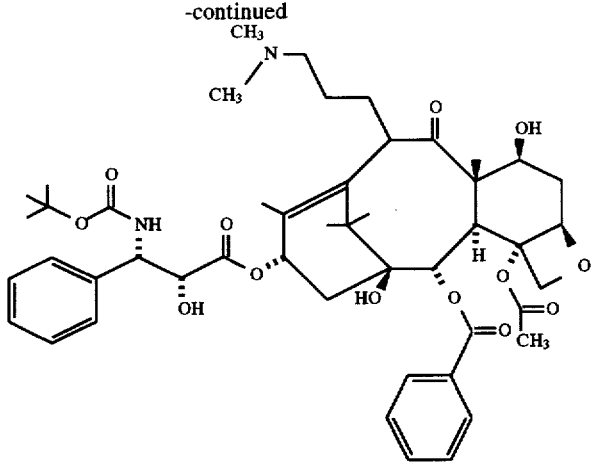

Step 1: 10-Deacetoxy-10-(3-dimethylaminopropyl)-7-O-triethylsilylbaccatin III

The compound obtained in Step 1 of Example 11 was reacted in the same manner as in Step 2 of Example 11 except for using dimethylamine in place of morpholine to yield the titled compound as a white amorphous solid.

$^1$H-NMR (CDCl$_3$/TMS) δ(ppm): 0.50–0.61(6H, m), 0.95 (9H, t, J=8 Hz), 1.05(3H, s), 1.11(3H, s), 1.45–1.54(2H, m), 1.62(3H, s), 1.65–1.92(6H, m), 1.97(3H, d, J=1 Hz), 2.04–2.44(4H, m), 2.25(6H, s), 2.29(3H, s), 2.44–2.52(1H, m), 3.81(1H, dd, J=5 Hz, 10 Hz), 4.06(1H, d, J=7 Hz), 4.16(1H, d, J=8 Hz), 4.29(1H, d, J=8 Hz), 4.54(1H, dd, J=11 Hz, 7 Hz), 4.81–4.85(1H, m), 4.96(1H, d, J=8 Hz), 5.60(1H, d, J=7 Hz), 7.47(2H, t, J=8 Hz), 7.52–7.61(1H, m), 8.11(2H, d, J=7 Hz).

Step 2: 13-O-[(2R,3S)-3-(tert-Butoxycarbonyl)-N,O-isopropylidene-3-phenylisoserinyl]-10-deacetoxy-10-(3-dimethylaminopropyl)-7-O-triethylsilylbaccatin III The compound obtained in the above Step 1 was reacted in the same manner as in Step 1 of Example 14 to yield the titled compound as a white amorphous solid.

$^1$H-NMR (CDCl$_3$/TMS) δ(ppm): 0.49–0.59(6H, m), 0.94 (9H, t, J=8 Hz), 1.10(9H, br-s), 1.12(3H, s), 1.19(3H, s), 1.59(3H, s), 1.77(3H, s), 1.81(3H, s), 1.84(3H, s), 2.09–2.16 (3H, m), 2.33(6H, s), 2.40–2.50(3H, m), 3.72–3.78(1H, m), 3.92(1H, d, J=7 Hz), 4.11(1H, d, J=8 Hz), 4.24(1H, d, J=8 Hz), 4.45(1H, d, J=7 Hz), 4.46–4.51(1H, m), 4.88(1H, d, J=8 Hz), 5.06(1H, br), 5.61(1H, d, J=7 Hz), 6.22(1H, m), 7.30–7.40(5H, m), 7.50(2H, t, J=8 Hz), 7.63(1H, t, J=7 Hz), 8.04(2H, d, J=7 Hz).

Step 3: 13-O-[(2R,3S)-3-(tert-Butoxycarbonylamino)-2-hydroxy-3-phenylpropionyl]-10-deacetoxy-10-(3-dimethylaminopropyl)baccatin III The compound obtained in the above Step 2 was reacted in the same manner as in Step 2 of Example 14 to yield the titled compound as a white amorphous material.

$^1$H-NMR (CDCl$_3$/TMS) δ(ppm): 1.09–2.72(40H, m, incl. s at 1.09, 1.19, 1.67, 1.81, 2.37 each 3H, 1.25 s 9H, 2.61 s 6H), 3.85–3.90(1H, m), 4.00(1H, d, J=7 Hz), 4.18(1H, d, J=8 Hz), 4.29(1H, d, J=8 Hz), 4.39–4.48(1H, m), 4.96(1H, d, J=8 Hz), 5.24–5.30(1H, m), 5.43–5.48(1H, m), 5.63(1H, d, J=7 Hz), 6.14(1H, m), 7.31–7.40(5H, m), 7.49(2H, t, J=8 Hz), 7.60(1H, m), 8.11(2H, d, J=8 Hz).

MS-FAB: 878(MH$^+$)

EXAMPLE 16

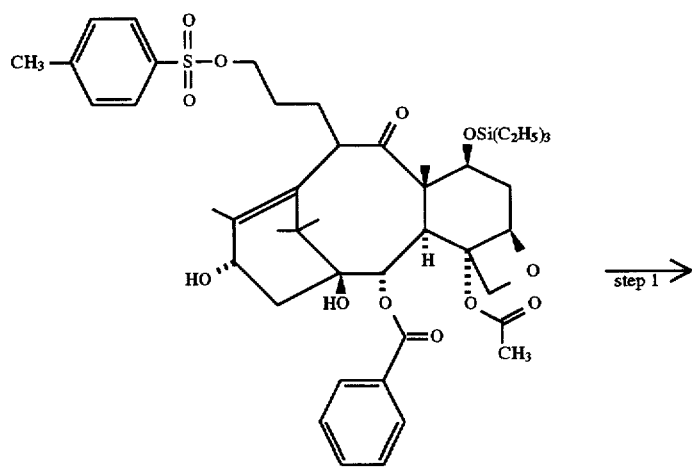

-continued
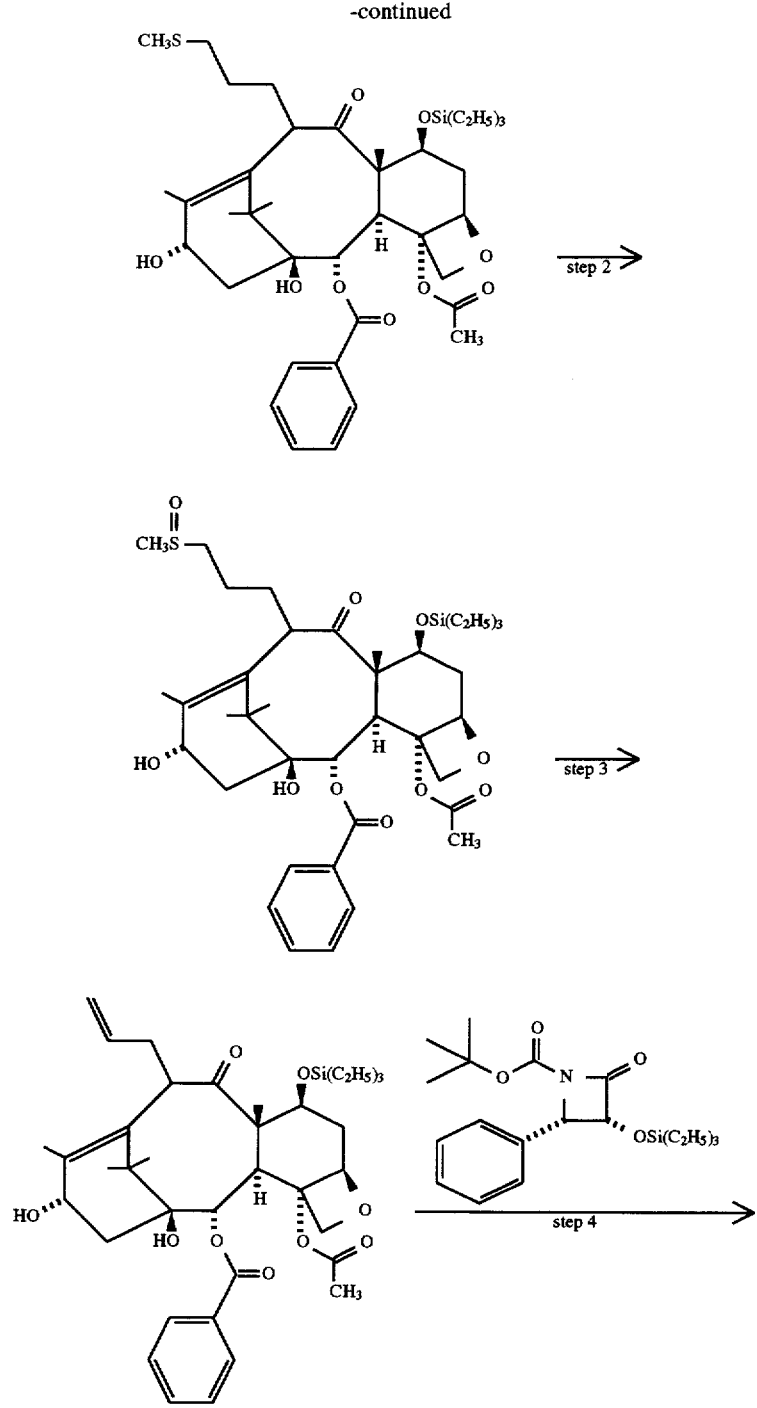

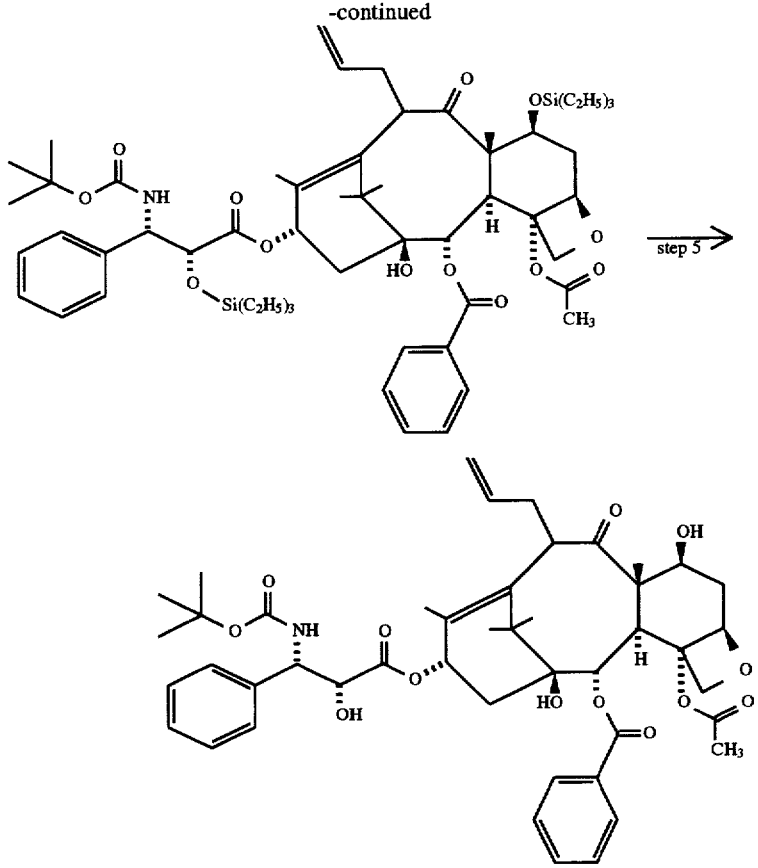

Step 1: 10-Deacetoxy-10-(3-methylthioproyl)-7-O-triethylsilylbaccatin III 425 mg of the compound obtained in Step 1 of Example 11 was dissolved in 5 ml of dried tetrahydrofuran. After cooling to 0° C., 2.3 ml of a 50% (w/v) methylmercapto sodium aqueous solution and 127 mg of tetrabutyl ammonium iodide were added thereto, followed by stirring at room temperature for 6 hours. The reaction solution was diluted with ethyl acetate, then washed successively with water and a saturated aqueous sodium chloride solution, and dried over anhydrous sodium sulfate. After evaporation of the solvent under reduced pressure, the resulting residue was purified by silica gel thin layer chromatography (a developing solvent; chloroform:hexane:acetone=7:2.5:0.5 (v/v)) to yield 332 mg of the titled compound.

$^1$H-NMR (CDCl$_3$/TMS) δ(ppm): 0.56(6H, m), 0.96(9H, t, J=8 Hz), 1.06(3H, s), 1.12(3H, s), 1.62(3H, s), 1.7–2.0(3H, m), 1.97(3H, s), 2.11(3H, s), 2.1–2.35(4H, m), 2.29(3H, s), 2.45–2.65(3H, m), 3.81(1H, dd, J=4 Hz, 9 Hz), 4.06(1H, d, J=7 Hz), 4.17(1H, d, J=8 Hz), 4.30(1H, d, J=8 Hz), 4.54(1H, dd, J=7 Hz, 11 Hz), 4.86(1H, br), 4.96(1H, dd, J=2 Hz, 9 Hz), 5.60(1H, d, J=7 Hz), 7.47(2H, t, J=7 Hz), 7.60(1H, t, J=7 Hz), 8.11(2H, d, J=7 Hz).

Step 2: 10-Deacetoxy-10-(3-methylsulfinylpropyl)-7-O-triethylsilylbaccatin III 332 mg of the compound obtained in the above Step 1 was dissolved in 7 ml of methanol. After cooling to 0° C., an aqueous solution of sodium metaperiodate (150 mg of the iodate dissolved in 3.5 ml of distilled water) was added thereto, followed by stirring at 0° C. for 2 hours. The reaction solution was diluted with ethyl acetate, then washed successively with water and a saturated aqueous sodium chloride solution, and dried over anhydrous sodium sulfate. After evaporation of the solvent under reduced pressure, the resulting residue was purified by silica gel thin layer chromatography (a developing solvent; chloroform containing 6% (v/v) of methanol) to yield 312 mg of the titled compound.

$^1$H-NMR (CDCl$_3$/TMS) δ(ppm): 0.55(6H, m), 0.95(9H, t, J=8 Hz), 1.11, 1.10, 1.08 and 1.06(total 6H, each s), 1.63(3H, s), 1.98(3H, s), 2.29(3H, s), 1.7–2.35(6H, m), 2.50(1H, m), 2.59(3H, s), 2.6–2.9(3H, m), 3.86(1H, dd, J=5 Hz, 10 Hz), 4.04(1H, d, J=7 Hz), 4.16(1H, d, J=8 Hz), 4.30(1H, d, J=8 Hz), 4.55(1H, dd, J=6 Hz, 10 Hz), 4.85(1H, br), 4.97(1H, d, J=8 Hz), 5.60(1H, d, J=7 Hz), 7.47(2H, t, J=7 Hz), 7.60(1H, t, J=7 Hz), 8.11(2H, d, J=7 Hz).

Step 3: 10-Allyl-10-deacetoxy-7-O-triethylsilylbaccatin III 294 mg of the compound obtained in the above Step 2 was dissolved in 20 ml of o-dichlorobenzene, and 42 mg of sodium carbonate was added thereto, followed by stirring at 170° C. for 4 hours. After removing the insoluble material by filtration, the solvent was evaporated under reduced pressure, the resulting residue was purified by silica gel thin layer chromatography (a developing solvent; chloroform:hexane:acetone=7:2:1 (v/v)) to yield 100 mg of the titled compound.

$^1$H-NMR (CDCl$_3$/TMS) δ(ppm): 0.57(6H, m), 0.96(9H, t, J=8 Hz), 1.13(3H, s), 1.08(3H, s), 1.63(3H, s), 1.89(1H, m), 1.93(3H, d, J=1 Hz), 2.15–2.35(2H, m), 2.29(3H, s), 2.4–2.6 (2H, m), 2.80(1H, m), 3.90(1H, dd, J=4 Hz, 10 Hz), 4.05 (1H, d, J=7 Hz), 4.17(1H, d, J=8 Hz), 4.30(1H, d, J=8 Hz), 4.54(1H, dd, J=7 Hz, 11 Hz), 4.85(1H, br), 4.96(1H, dd, J=2 Hz, 10 Hz), 5.01(1H, br-d, J=10 Hz), 5.09(1H, br-d, J=16 Hz), 5.61(1H, d, J=7 Hz), 5.79(1H, tdd, J=7 Hz, 10 Hz, 16 Hz), 7.47(2H, t, J=7 Hz), 7.60(1H, t, J=7 Hz), 8.11(2H, d, J=7 Hz).

Step 4: 10-Allyl-13-O-[(2R,3S)-3-(tert-butoxycarbonylamino)-2-triethylsilyloxy-3-phenylpropionyl]-10-deacetoxy-7-O-triethylsilylbaccatin III 100 mg of sodium hydride (a 60% (w/w) oil suspension) was washed with dried hexane, and then 1.5 ml of dried tetrahydrofuran was added. While stirring the mixture at 0° C., a dried tetrahydrofuran solution (1.5 ml) of 100 mg of the compound obtained in the above Step 3 and a dried tetrahydrofuran solution (1 ml) of 110 mg of (3R,4S)-1-tert-butoxycarbonyl-4-phenyl-3-(triethylsilyloxy)azetidin-2-one were successively added thereto, followed by stirring at that temperature for 2 hours. 15 ml of a 10% (w/v) aqueous ammonium chloride solution was added to the reaction solution, and the mixture was extracted twice with ethyl acetate. The extract was washed with a saturated aqueous sodium chloride solution and then dried over anhydrous sodium sulfate. The solvent was evaporated under reduced pressure, the resulting residue was purified by silica gel thin layer chromatography (a developing solvent; chloroform:hexane:acetone=5:4.5:0.5 (v/v)) to yield 141 mg of the titled compound.

$^1$H-NMR (CDCl$_3$/TMS) δ(ppm): 0.38(6H, m), 0.57(6H, m), 0.78(9H, t, J=8 Hz), 0.96(9H, m), 1.16(3H, s), 1.25(3H, s), 1.30(9H, s), 1.64(3H, s), 1.76(3H, s), 1.91(1H, m), 2.13(1H, m), 2.38(1H, m), 2.45–2.55(1H, m), 2.48(1H, m), 2.52(3H, s), 2.84(1H, m), 3.84(1H, dd, J=4 Hz, 10 Hz), 3.99(1H, d, J=7 Hz), 4.21(1H, d, J=8 Hz), 4.31(1H, d, J=8 Hz), 4.52(1H, dd, J=7 Hz, 11 Hz), 4.54(1H, br-s), 4.96(1H, dd, J=2 Hz, 10 Hz), 5.04(1H, br-d, J=10 Hz), 5.10(1H, br-d, J=17 Hz), 5.39(1H, br), 5.49(1H, br), 5.67(1H, d, J=7 Hz), 5.78(1H, m), 6.26(1H, t, J=9 Hz), 7.2–7.4(5H, m), 7.48(2H, t, J=7 Hz), 7.58(1H, t, J=7 Hz), 8.12(2H, d, J=7 Hz).

Step 5: 10-Allyl-13-O-[(2R,3S)-3-(tert-butoxycarbonylamino)-2-hydroxy-3-phenylpropionyl]-10-deacetoxybaccatin III 0.2 ml of hydrogen fluoride-pyridine was added at 0° C. to a mixture comprising 9 mg of the compound obtained in the above Step 4 and 1 ml of pyridine, followed by stirring at room temperature for 2 hours. The reaction solution was diluted with ethyl acetate and washed successively with water and a saturated aqueous sodium chloride solution, and the resulting organic layer was dried over anhydrous sodium sulfate. The solvent was evaporated under reduced pressure, the resulting residue was purified by silica gel thin layer chromatography (a developing solvent; chloroform containing 3% (v/v) methanol) to yield 6 mg of the titled compound.

Melting Point: 138°–142° C. (a dioxane solution was freeze-dried)

$^1$H-NMR (CDCl$_3$/TMS) δ(ppm): 1.15(3H, s), 1.23(3H, s), 1.33(9H, s), 1.65(3H, s), 1.74(3H, s), 1.82(1H, m), 2.21(1H, m), 2.37(3H, s), 2.25–2.40(2H, m), 2.57(1H, m), 2.94(1H, td, J=7 Hz, 15 Hz), 3.89(1H, t, J=7 Hz), 4.01(1H, d, J=7 Hz), 4.20(1H, d, J=8 Hz), 4.30(1H, d, J=8 Hz), 4.31(1H, m), 4.61(1H, br-s), 4.95(1H, dd, J=2 Hz, 9 Hz), 5.01(1H, br-d, J=10 Hz), 5.10(1H, br-d, J=17 Hz), 5.27(1H, br-d, J=9 Hz), 5.37(1H, br-d, J=9 Hz), 5.68(1H, d, J=7 Hz), 5.78(1H, m), 6.21(1H, br-t, J=9 Hz), 7.30–7.45(5H, m), 7.50(2H, t, J=7 Hz), 7.61(1H, t, J=7 Hz), 8.12(2H, d, J=7 Hz).

EXAMPLE 17

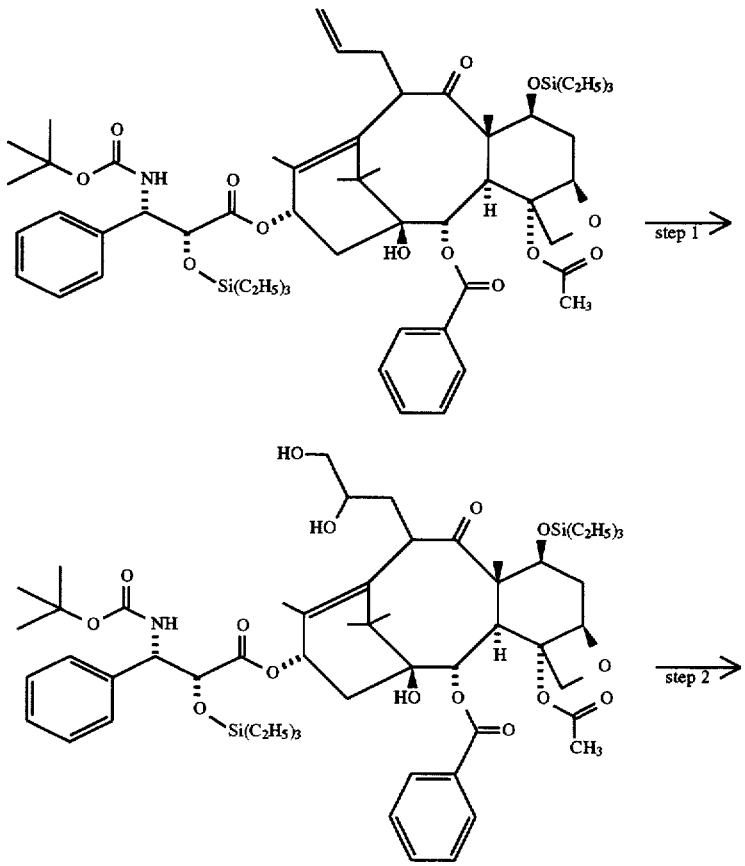

-continued

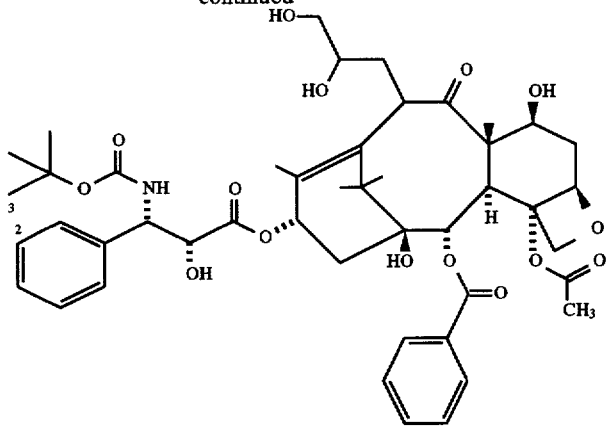

Step 1: 13-O-[(2R,3S)-3-(tert-Butoxycarbonylamino)-2-triethylsilyloxy-3-phenylpropionyl]-10-deacetoxy-10-(2,3-dihydroxypropyl)-7-O-triethylsilylbaccatin III A catalytic amount of osmium tetroxide was added at 0° C. to a mixture of 54 mg of the compound obtained in Step 4 of Example 16, 9 mg of N-methylmorpholine-N-oxide, 1 ml of tetrahydrofuran and 0.2 ml of water, followed by stirring at room temperature for one hour. The reaction solution was diluted with ethyl acetate and washed successively with water and a saturated aqueous sodium chloride solution, and the resulting organic layer was dried over anhydrous sodium sulfate. The solvent was evaporated under reduced pressure, the resulting residue was purified by silica gel thin layer chromatography (a developing solvent; chloroform:hexane:acetone=7:2.5:0.5 (v/v)) to yield 41 mg of the titled compound as a mixture of diastereomers.

$^1$H-NMR (CDCl$_3$/TMS) δ(ppm): 8.12(2H, d, J=7 Hz), 7.58(1H, t, J=7 Hz), 7.48(2H, t, J=7 Hz), 7.2–7.4(5H, m), 6.15–6.30(1H, m), 5.67(1H, m), 5.45–5.55(1H, m), 5.29(1H, m), 4.97(1H, d, J=9 Hz), 4.5–4.7(1H, m), 4.55(1H, br-s), 4.32(1H, d, J=8 Hz), 3.95–4.25(3H, m), 3.4–3.8(3H, m), 2.53(3H, s), 1.93 and 1.88(total 3H, each s), 1.65 and 1.64(total 3H, each s), 1.30(9H, s), 1.24 and 1.20(total 3H, each s), 1.14 and 1.12(total 3H, each s), 0.96(9H, m), 0.77(9H, m), 0.59(6H, m), 0.39(6H, m).

Step 2: 13-O-[(2R,3S)-3-(tert-Butoxycarbonylamino)-2-hydroxy-3-phenylpropionyl]-10-deacetoxy-10-(2,3-dihydroxypropyl)baccatin III 10 mg of the compound obtained in the above Step 1 was reacted in the same manner as in Step 5 of Example 16 and purified by silica gel thin layer chromatography (a developing solvent; chloroform containing 10% (v/v) methanol) to yield 5 mg of Isomer A as a lower polarity fraction and 3 mg of Isomer B as a higher polarity fraction.

Isomer A

Melting Point: 149°–154° C. (A dioxane solution was freeze-dried.)

$^1$H-NMR (CDCl$_3$/TMS) δ(ppm): 8.11(2H, d, J=7 Hz), 7.61(1H, t, J=7 Hz), 7.50(1H, t, J=7 Hz), 7.34–7.43(4H, m), 7.31(1H, m), 6.16(1H, br), 5.65(1H, d, J=7 Hz), 5.43(1H, br), 5.27(1H, br), 4.98(1H, dd, J=2 Hz, 10 Hz), 4.62(1H, br-s), 4.44(1H, dd, J=6 Hz, 10 Hz), 4.30(1H, d, J=8 Hz), 4.26(1H, br-d, J=10 Hz), 4.19(1H, d, J=8 Hz), 3.97(1H, d, J=7 Hz), 3.9–4.0(1H, m), 3.72(1H, dd, J=3 Hz, 11 Hz), 3.44(1H, dd, J=7 Hz, 11 Hz), 2.1–2.6(4H, m), 2.38(3H, s), 1.84(1H, m), 1.80(3H, s), 1.63(3H, s), 1.5–1.8(1H, m), 1.32(9H, s), 1.19(3H, s), 1.11(3H, s).

Isomer B

Melting Point: 151°–157° C. (A dioxane solution was freeze-dried.)

$^1$H-NMR (CDCl$_3$/TMS) δ(ppm): 8.11(2H, d, J=7 Hz), 7.61(1H, t, J=7 Hz), 7.50(2H, t, J=7 Hz), 7.35–7.44(4H, m), 7.32(1H, m), 6.17(1H, br), 5.66(1H, d, J=7 Hz), 5.43(1H, br), 5.27(1H, br), 4.97(1H, br-d, J=9 Hz), 4.61(1H, br-s), 4.38(1H, dd, J=6 Hz, 10 Hz), 4.30(1H, d, J=8 Hz), 4.18(1H, d, J=8 Hz), 4.10(1H, m), 3.99(1H, d, J=7 Hz), 3.5–3.75(3H, m), 2.45–2.65(2H, m), 2.36(3H, s), 2.1–2.45(2H, m), 1.87(3H, s), 1.65(3H, s), 1.5–1.9(2H, m), 1.32(9H, s), 1.19(3H, s), 1.10(3H, s).

EXAMPLE 18

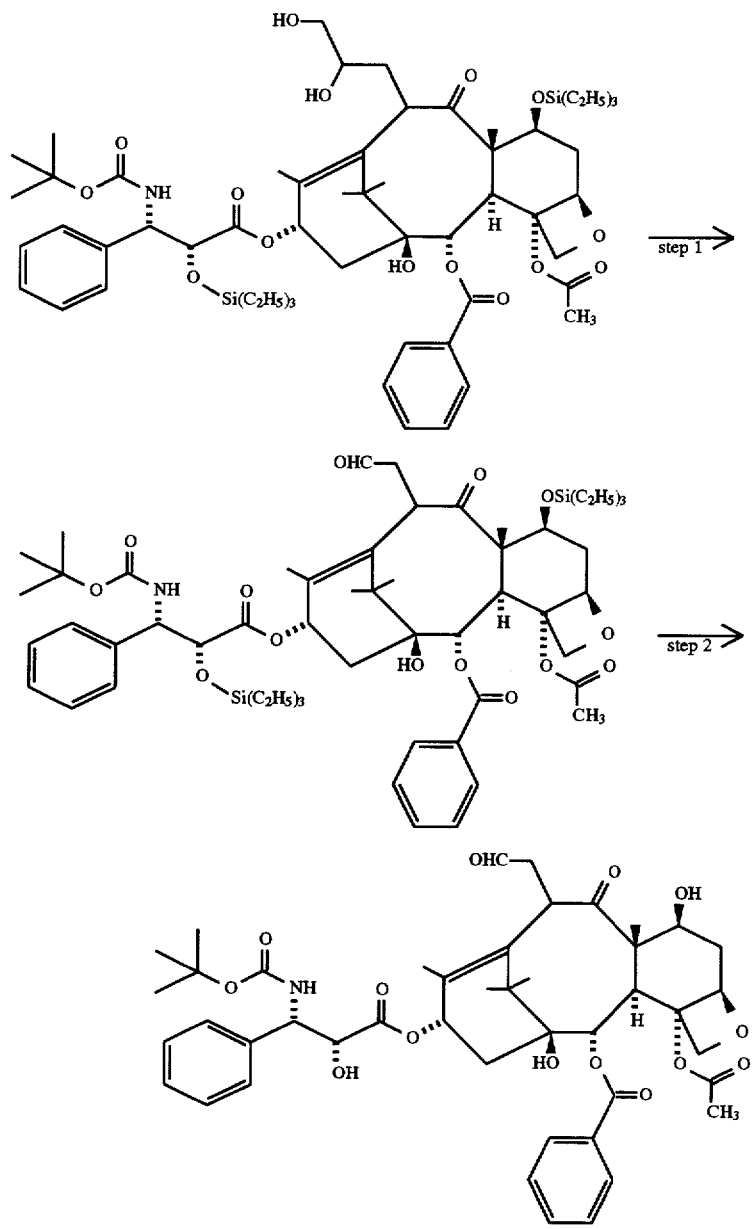

Step 1: 13-O-[(2R,3S)-3-(tert-Butoxycarbonylamino)-2-triethylsilyloxy-3-phenylpropionyl]-10-deacetoxy-10-formylmethyl-7-O-triethylsilylbaccatin III 40 mg of sodium metaperiodate was added at 0° C. to a mixture of 33 mg of the compound obtained in Step 1 of Example 17, 1.5 ml of tetrahydrofuran and 1.5 ml of water, followed by stirring at room temperature for 23 hours. The reaction solution was diluted with ethyl acetate, then washed successively with water and a saturated aqueous sodium chloride solution, and the organic layer thus obtained was dried over anhydrous sodium sulfate. After evaporation of the solvent under reduced pressure, the resulting residue was purified by silica gel thin layer chromatography (a developing solvent; chloroform:hexane:acetone=7:2.5:0.5 (v/v)) to yield 30 mg of the titled compound.

$^1$H-NMR CDCl$_3$/TMS) δ(ppm): 9.79(1H, s), 8.12(2H, d, J=7 Hz), 7.58(1H, t, J=7 Hz), 7.48(2H, t, J=7 Hz), 7.37(2H, t, J=7 Hz), 7.22–7.32(3H, m), 6.21(1H, t, J=10 Hz), 5.68(1H, d, J=7 Hz), 5.48(1H, br), 5.29(1H, br), 4.97(1H, dd, J=2 Hz, 10 Hz), 4.59(1H, dd, J=7 Hz, 11 Hz), 4.54(1H, br-s), 4.49(1H, t, J=6 Hz), 4.32(1H, d, J=8 Hz), 4.20(1H, d, J=8 Hz), 4.00(1H, d, J=7 Hz), 3.59(1H, dd, J=6 Hz, 17 Hz), 2.45–2.62(2H, m), 2.53(3H, s), 2.38(1H, m), 2.15(1H, m), 1.92(1H, m), 1.88(3H, s), 1.66(3H, s), 1.29(9H, s), 1.24(3H, s), 1.13(3H, s), 0.94(9H, t, J=8 Hz), )0.78(9H, t, J=8 Hz), 0.57(6H, m), 0.39(6H, m).

Step 2: 13-O-[(2R,3S)-3-(tert-Butoxycarbonylamino)-2-hydroxy-3-phenylpropionyl]-10-deacetoxy-10-(formylmethyl)baccatin III The compound obtained in the above Step 1 was reacted in the same manner as in Step 5 of Example 16 and then purified to yield the titled compound.

Melting Point: 147°–153° C. (A dioxane solution was freeze-dried.)

$^1$H-NMR (CDCl$_3$/TMS) δ(ppm): 9.82(1H, s), 8.12(2H, d, J=7 Hz), 7.61(1H, t, J=7 Hz), 7.50(2H, t, J=7 Hz), 7.35–7.45 (4H, m), 7.32(1H, m), 6.17(1H, br), 5.66(1H, d, J=7 Hz), 5.36(1H, d, J=9 Hz), 5.26(1H, br-d, J=9 Hz), 4.98(1H, dd, J=2 Hz, 9 Hz), 4.61(1H, br-s), 4.53(1H, m), 4.49(1H, dd, J=2 Hz, 11 Hz), 4.31(1H, d, J=8 Hz), 4.20(1H, d, J=8 Hz), 3.95(1H, d, J=7 Hz), 3.60(1H, dd, J=11 Hz, 19 Hz), 2.58(1H, m), 2.42(1H, dd, J=2 Hz, 19 Hz), 2.39(3H, s), 2.33(1H, m), 2.20(1H, dd, J=8 Hz, 16 Hz), 1.91(1H, m), 1.73(3H, s), 1.64(3H, s), 1.32(9H, s), 1.21(3H, s), 1.08(3H, s).

EXAMPLE 19

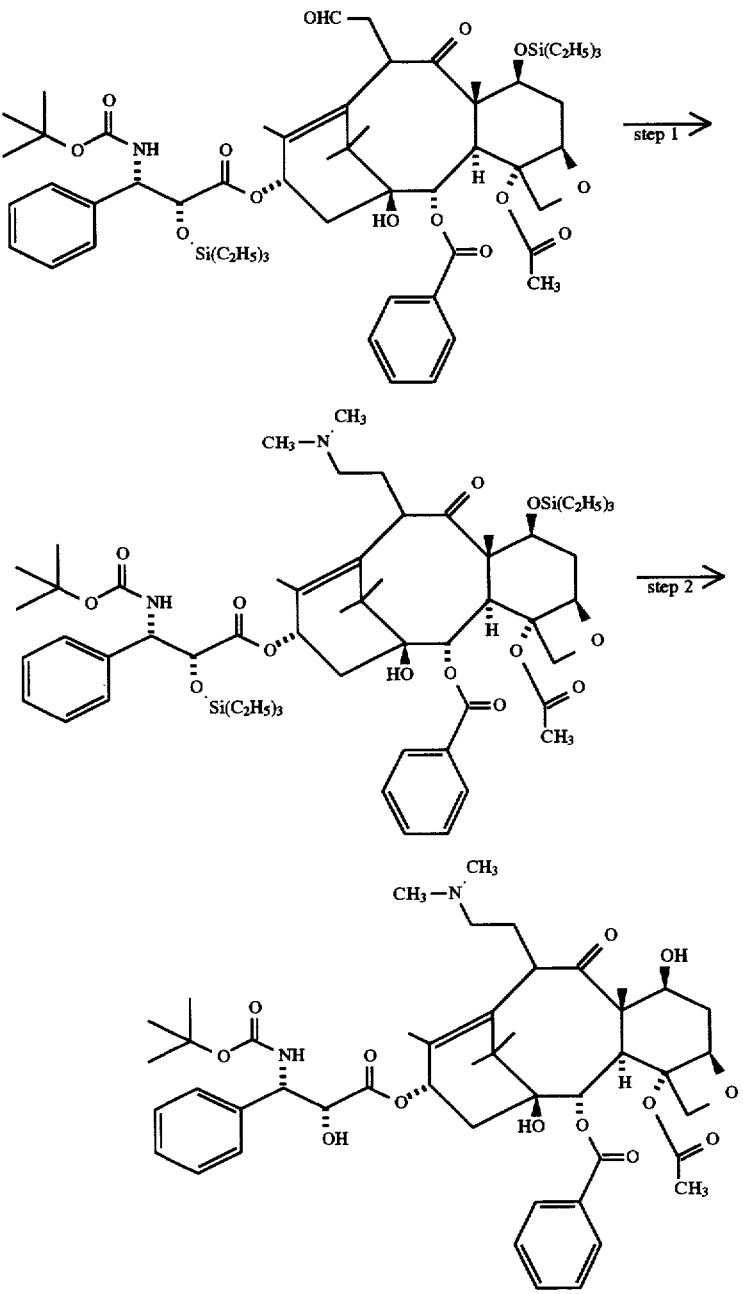

Step 1: 13-O-[(2R,3S)-3-(tert-Butoxycarbonylamino)-2-triethylsilyloxy-3-phenylpropionyl]-10-deacetoxy-10-(2-dimethylaminoethyl)-7-O-triethylsilylbaccatin III A mixture of 21 mg of the compound obtained in Step 1 of Example 18, 2 ml of methanol, 0.3 ml of dimethylamine and 50 mg of palladium-carbon (50% (w/w) wet) was stirred under a hydrogen stream for 1.5 hour. After removing the insoluble material by filtration, the solvent was evaporated under reduced pressure, and the resulting residue was purified by silica gel thin layer chromatography (a developing solvent; chloroform containing 3% (v/v) methanol) to yield 17 mg of the titled compound.

$^1$H-NMR (CDCl$_3$/TMS) δ(ppm): 8.12(2H, d, J=7 Hz), 7.58(1H, t, J=7 Hz), 7.48(2H, t, J=7 Hz), 7.37(2H, t, J=7 Hz), 7.22–7.32(3H, m), 6.26(1H, t, J=9 Hz), 5.67(1H, d, J=7 Hz), 5.49(1H, br), 5.29(1H, br), 4.96(1H, dd, J=2 Hz, 10 Hz), 4.55(1H, br-s), 4.52(1H, dd, J=6 Hz, 11 Hz), 4.31(1H, d, J=8 Hz), 4.20(1H, d, J=8 Hz), 3.99(1H, d, J=7 Hz), 3.79(1H, dd, J=4 Hz, 9 Hz), 2.53(3H, s), 2.49(1H, m), 2.2–2.45(3H, m), 2.28(6H, s), 2.14(1H, m), 1.91(1H, m), 1.82(3H, s), 1.7–1.8(2H, m), 1.64(3H, s), 1.31(9H, s), 1.23(3H, s), 1.16(3H, s), 0.96(1H, t, J=8 Hz), 0.78(9H, t, J=8 Hz), 0.57(6H, m), 0.40(6H, m).

Step 2: 13-O-[(2R,3S)-3-(tert-Butoxycarbonylamino)-2-hydroxy-3-phenylpropionyl]-10-deacetoxy-10-(2-dimethylaminoethyl)baccatin III The compound obtained in the above Step 1 was reacted in the same manner as in Step 5 of Example 16 and then purified to yield the titled compound.

Melting Point: 139°–141° C. (A dioxane solution was freeze-dried.)

$^1$H-NMR (CDCl$_3$/TMS) δ(ppm): 8.11(2H, d, J=7 Hz), 7.60(1H, t, J=7 Hz), 7.49(2H, t, J=7 Hz), 7.35–7.45(4H, m), 7.32(1H, m), 6.18(1H, br-t, J=9 Hz), 5.64(1H, d, J=7 Hz), 5.37(1H, d, J=10 Hz), 5.27(1H, br), 5.00(1H, dd, J=2 Hz, 10 Hz), 4.60(1H, br-s), 4.46(1H, dd, J=7 Hz, 11 Hz), 4.30(1H, d, J=8 Hz), 4.19(1H, d, J=8 Hz), 4.08(1H, dd, J=2 Hz, 9 Hz), 3.92(1H, d, J=7 Hz), 2.86(1H, m), 2.4–2.6(2H, m), 2.37(3H, s), 2.25(6H, s), 2.15–2.35(2H, m), 1.80(3H, d, J=1 Hz), 1.7–2.0(2H, m), 1.62(3H, s), 1.51(1H, m), 1.33(9H, s), 1.21(3H, s), 1.12(3H, s).

EXAMPLE 20

Step 1: 13-O-[(2R,3S)-3-(tert-Butoxycarbonylamino)-2-hydroxy-3-phenylpropionyl]-10-deacetoxy-10-(2-morpholinoethyl)baccatin III

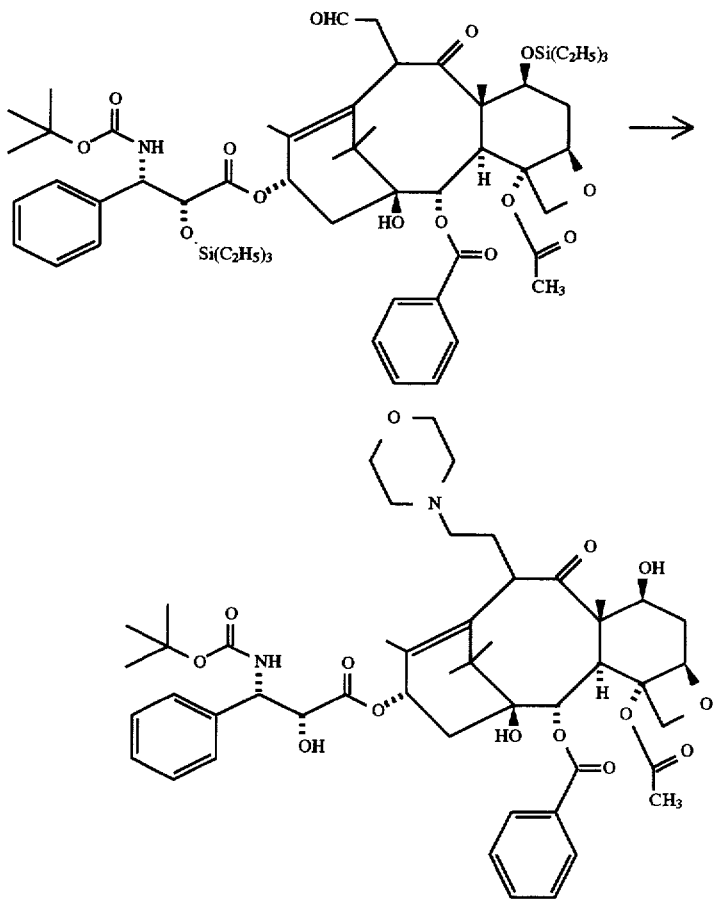

The compound obtained in Step 1 of Example 18 was reacted in the same manner as in Step 1 of Example 19 except for using morpholine in place of dimethylamine and then purified. The resulting compound was reacted in the same manner as in Step 5 of Example 16 and then purified to yield the titled compound.

Melting Point: 145°–149° C. (A dioxane solution was freeze-dried.)

¹H-NMR (CDCl₃/TMS) δ(ppm): 8.11(2H, d, J=7 Hz), 7.61(1H, t, J=7 Hz), 7.50(2H, t, J=7 Hz), 7.35–7.44(4H, m), 7.32(1H, m), 6.17(1H, br), 5.64(1H, d, J=7 Hz), 5.37(1H, d, J=9 Hz), 5.27(1H, br-d, J=9 Hz), 5.00(1H, dd, J=2 Hz, 10 Hz), 4.60(1H, br-s), 4.44(1H, dd, J=6 Hz, 11 Hz), 4.30(1H, d, J=8 Hz), 4.19(1H, d, J=8 Hz), 4.01(1H, dd, J=2 Hz, 9 Hz), 3.94(1H, d, J=7 Hz), 3.68(4H, m), 2.15–2.75(9H, m), 2.38(3H, s), 1.78(3H, s), 1.7–1.95(2H, m), 1.62(3H, s), 1.45–1.55(1H, m), 1.33(9H, s), 1.21(3H, s), 1.11(3H, s).

EXAMPLE 21

13-O-[(2R,3S)-3-(tert-Butoxycarbonylamino)-2-hydroxy-3-phenylpropionyl]-10-deacetoxy-10-(2-piperidinoethyl)baccatin III

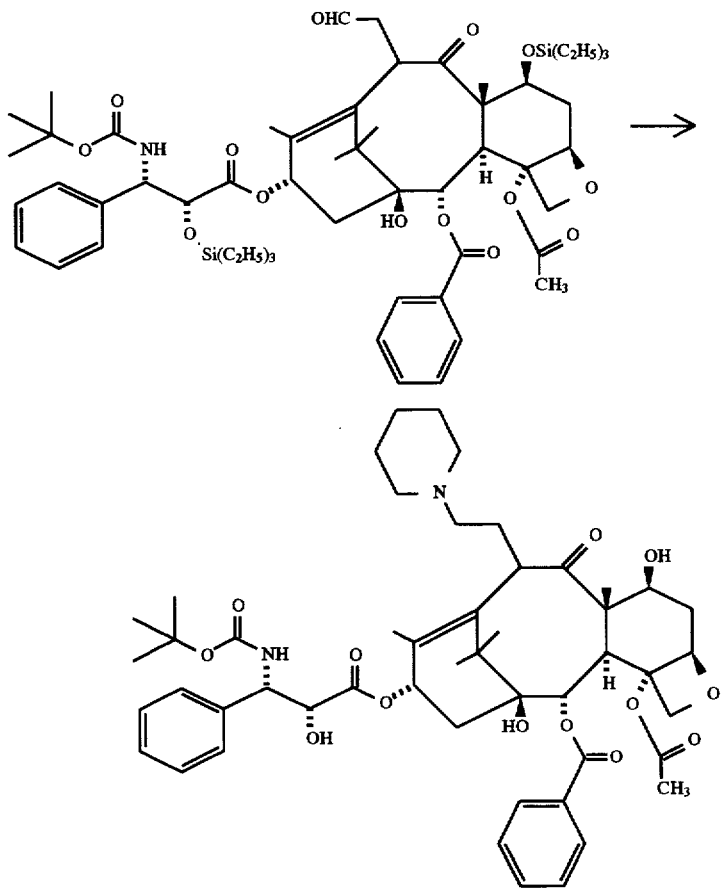

The compound obtained in Step 1 of Example 18 was reacted in the same manner as in Step 1 of Example 19 except for using piperidine in place of dimethylamine and then purified. The resulting compound was reacted in the same manner as in Step 5 of Example 16 and purified to yield the titled compound.

Melting Point: 143°–148° C. (A dioxane solution was freeze-dried.)

¹H-NMR (CDCl₃/TMS) δ(ppm): 8.11(2H, d, J=7 Hz), 7.61(1H, t, J=7 Hz), 7.50(2H, t, J=7 Hz), 7.35–7.44(4H, m), 7.31(1H, m), 6.17(1H, br), 5.63(1H, d, J=7 Hz), 5.40(1H, d, J=9 Hz), 5.27(1H, br-d, J=9 Hz), 4.99(1H, dd, J=2 Hz, 10 Hz), 4.61(1H, br-s), 4.48(1H, dd, J=6 Hz, 11 Hz), 4.29(1H, d, J=8 Hz), 4.18(1H, d, J=8 Hz), 4.14(1H, m), 3.94(1H, d, J=7 Hz), 2.88(1H, m), 2.43–2.75(4H, m), 2.38(3H, s), 2.14–2.40(2H, m), 1.90(1H, m), 1.83(3H, s), 1.45–1.80(8H, m), 1.63(3H, s), 1.33(9H, s), 1.20(3H, s), 1.12(3H, s).

EXAMPLE 22

13-O-[(2R,3S)-3-(tert-Butoxycarbonylamino)-2-hydroxy-3-phenylpropionyl]-10-deacetoxy-10-[2-(4-methylpiperazin-1-yl)ethyl]baccatin III

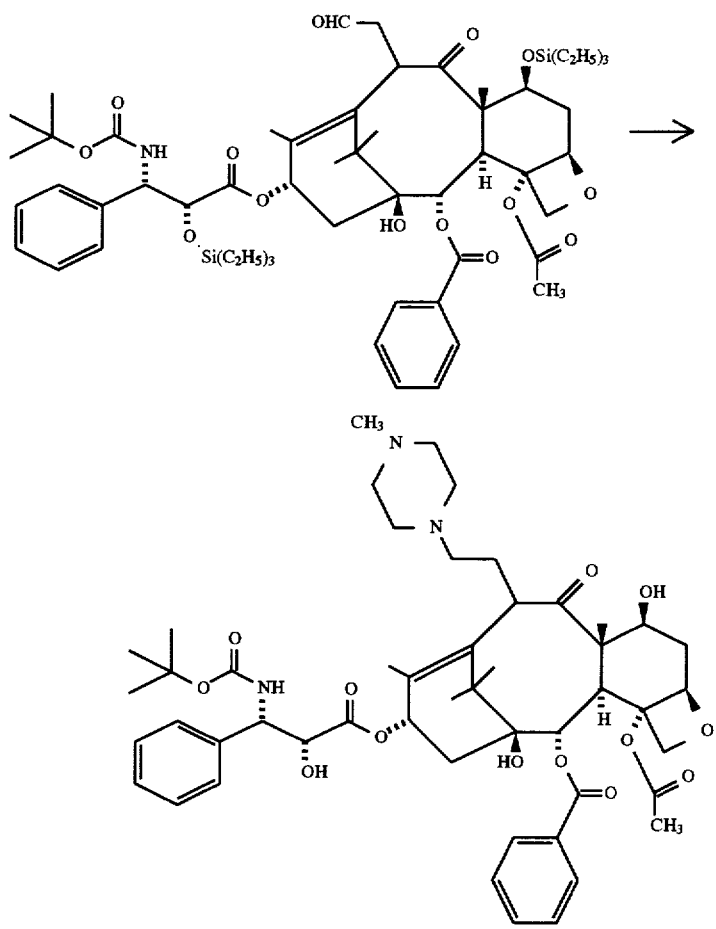

The compound obtained in Step 1 of Example 18 was reacted in the same manner as in Step 1 of Example 19 except for using N-methylpiperazine in place of dimethylamine, followed by purification. The resulting compound was reacted in the same manner as in Step 5 of Example 16, followed by purification to yield the titled compound.

Melting Point: 142°–149° C. (A dioxane solution was freeze-dried.)

$^1$H-NMR (CDCl$_3$/TMS) δ(ppm): 8.11(2H, d, J=7 Hz), 7.61(1H, t, J=7 Hz), 7.50(2H, t, J=7 Hz), 7.35–7.43(4H, m), 7.32(1H, m), 6.17(1H, br), 5.64(1H, d, J=7 Hz), 5.37(1H, d, J=10 Hz), 5.27(1H, br), 5.00(1H, dd, J=2 Hz, 10 Hz), 4.60(1H, br-s), 4.44(1H, dd, J=6 Hz, 11 Hz), 4.30(1H, d, J=8 Hz), 4.19(1H, d, J=8 Hz), 4.00(1H, br-d, J=9 Hz), 3.94(1H, d, J=7 Hz), 2.15–2.80(14H, m), 2.38(3H, s), 2.31(3H, s), 1.88(1H, m), 1.78(3H, s), 1.62(3H, s), 1.45–1.55(1H, m), 1.33(9H, s), 1.21(3H, s), 1.12(3H, s).

EXAMPLE 23

13-O-[(2R,3S)-3-(tert-Butoxycarbonylamino)-2-hydroxy-3-phenylpropionyl]-10-deacetoxy-10-[2-N-pyrrolidino)ethyl]baccatin III

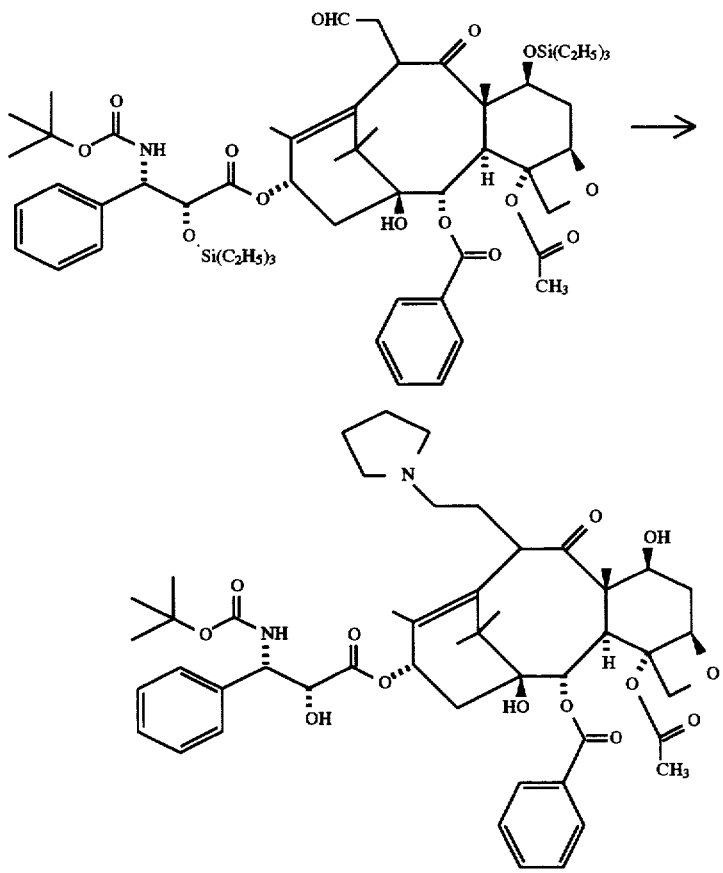

The compound obtained in Step 1 of Example 18 was reacted in the same manner as in Step 1 of Example 19 except for using pyrrolidine in place of dimethylamine, followed by purification. The resulting compound was reacted in the same manner as in Step 5 of Example 16, followed by purification to yield the titled compound.

Melting Point: 146°–150° C. (A dioxane solution was freeze-dried.)

$^1$H-NMR (CDCl$_3$/TMS) δ(ppm): 8.11(2H, d, J=7 Hz), 7.60(1H, t, J=7 Hz), 7.49(2H, t, J=7 Hz), 7.35–7.43(4H, m), 7.31(1H, m), 6.18(1H, br), 5.64(1H, d, J=7 Hz), 5.39(1H, d, J=9 Hz), 5.27(1H, br-d, J=9 Hz), 4.98(1H, dd, J=2 Hz, 9 Hz), 4.60(3H, br-s), 4.48(1H, dd, J=6 Hz, 11 Hz), 4.29(1H, d, J=8 Hz), 4.18(1H, d, J=8 Hz), 4.18–4.23(1H, m), 3.94(1H, d, J=7 Hz), 3.13(1H, m), 2.55–2.95(3H, m), 2.51–2.55(2H, m), 2.49(1H, m), 2.37(3H, s), 2.30(1H, m), 2.20(1H, m), 1.55–1.95(7H, m), 1.85(3H, s), 1.63(3H, s), 1.33(9H, s), 1.21(3H, s), 1.12(3H, s).

EXAMPLE 24
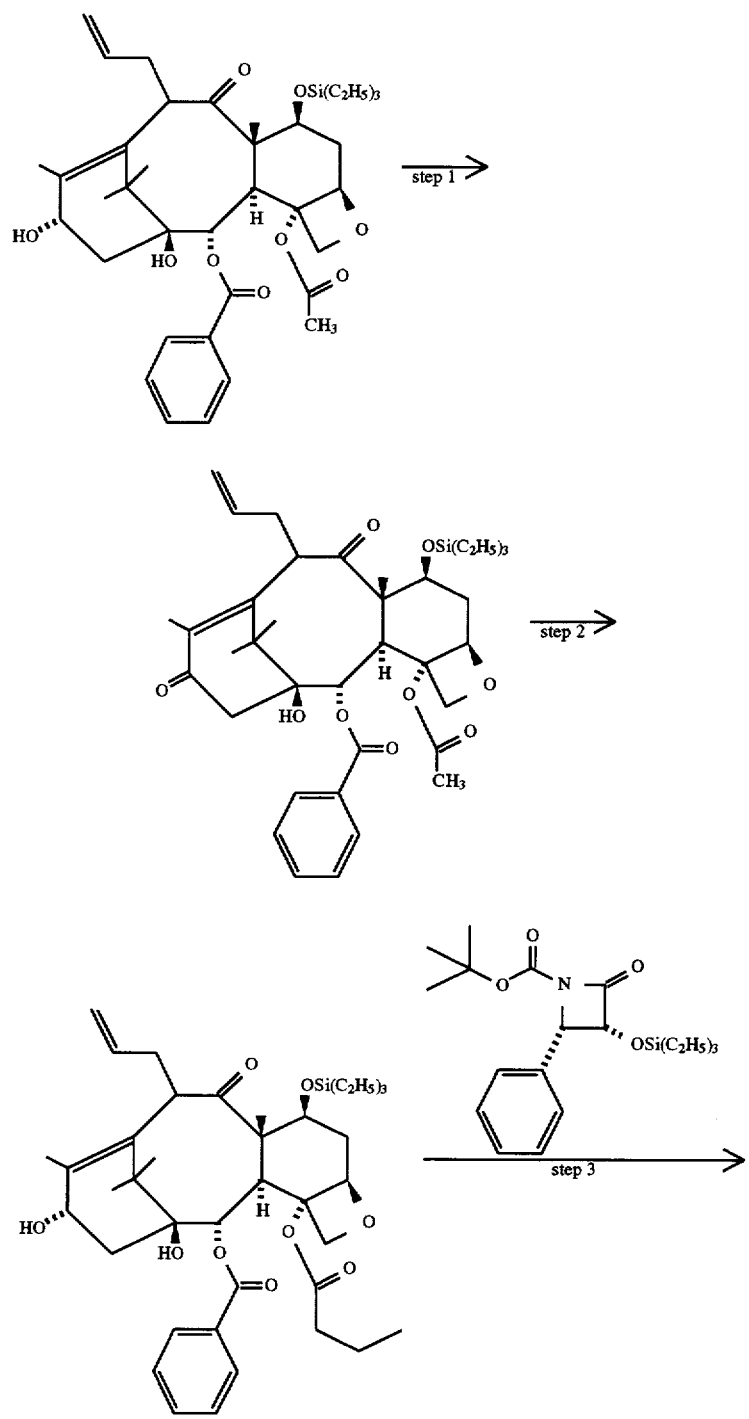

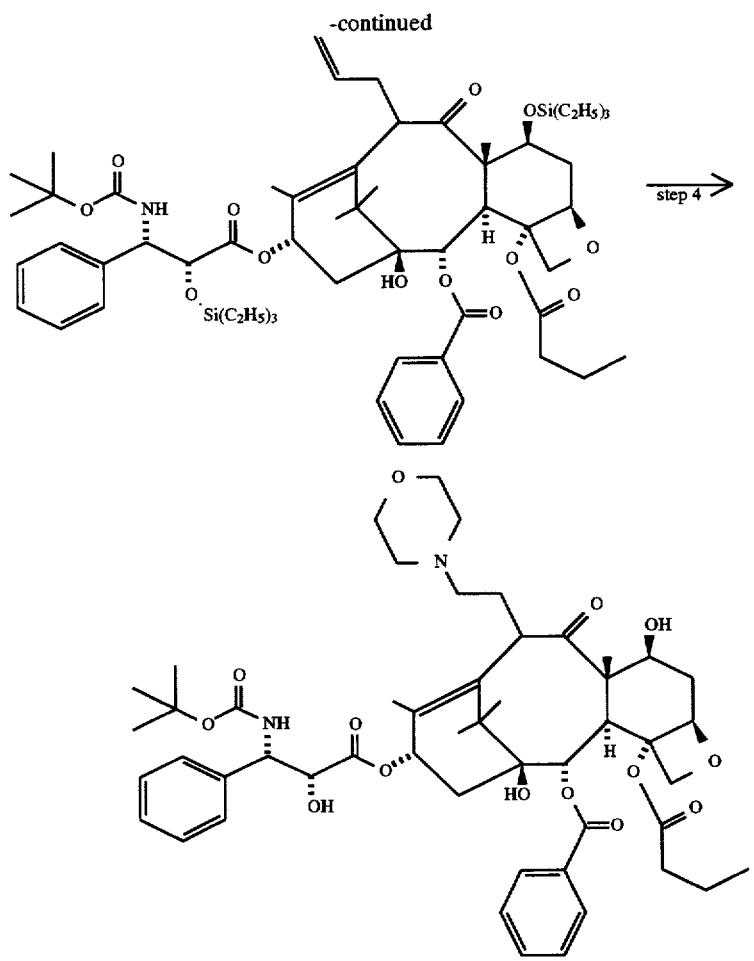

Step 1: 10-Allyl-10-deacetoxy-13-deoxy-13-oxo-7-O-triethylsilylbaccatin III

A mixture of 191 mg of the compound obtained in Step 3 of Example 16, 10 ml of dioxane and 250 mg of manganese dioxide was stirred at room temperature for 5 days. After removing the insoluble material by filtration, the solvent was evaporated under reduced pressure, and the resulting residue was purified by silica gel thin layer chromatography (a developing solvent; chloroform:hexane:acetone=7:2.5:0.5 (v/v)) to yield 150 mg of the titled compound.

$^1$H-NMR (CDCl$_3$/TMS) δ(ppm): 8.08(2H, d, J=7 Hz), 7.62(1H, t, J=7 Hz), 7.49(2H, t, J=7 Hz), 5.76(1H, dddd, J=7 Hz, 9 Hz, 11 Hz, 17 Hz), 5.66(1H, d, J=7 Hz), 5.16(1H, br-d, J=17 Hz), 5.08(1H, br-d, J=11 Hz), 4.93(1H, dd, J=2 Hz, 9.5 Hz), 4.52(1H, dd, J=6.5 Hz, 11 Hz), 4.32(1H, d, J=8 Hz), 4.15(1H, d, J=8 Hz), 4.12(1H, dd, J=5 Hz, 10 Hz), 4.02(1H, d, J=7 Hz), 2.95(1H, d, J=20 Hz), 2.88(1H, ddd, J=5 Hz, 7 Hz, 15 Hz), 2.70(1H, ddd, J=9 Hz, 10 Hz, 15 Hz), 2.62(1H, d, J=20 Hz), 2.49(1H, ddd, J=6.5 Hz, 9.5 Hz, 16 Hz), 2.18(3H, s), 1.98(3H, s), 1.88(1H, ddd, J=2 Hz, 11 Hz, 16 Hz), 1.62(3H, s), 1.22(6H, s), 0.96(9H, t, J=8 Hz), 0.58(6H, m).

Step 2: 10-Allyl-4-O-butanoyl-10-deacetoxy-4-deacetyl-7-O-triethylsilylbaccatin III 150 mg of the compound obtained in the above Step 1 was dissolved in 3 ml of tetrahydrofuran. After cooling to −78° C., 0.88 ml of sodium bis(trimethylsilyl)amide (a 1M tetrahydrofuran solution) was added thereto. After stirring at that temperature for 10 minutes, 0.083 ml of ethyl iodide was added to the mixture, followed by stirring for 80 minutes. A 10% (w/v) aqueous ammonium chloride solution was added to the reaction solution, and the mixture was extracted with ethyl acetate. The organic layer thus obtained was washed with a saturated aqueous sodium chloride solution, the resulting organic layer was dried over anhydrous sodium sulfate. The solvent was evaporated under reduced pressure, and the resulting residue was purified by silica gel thin layer chromatography (a developing solvent; hexane:ethyl acetate=6:1 (v/v)). The thus-obtained compound was dissolved in 4 ml of tetrahydrofuran, and 54 mg of sodium borohydride and 0.2 ml of methanol were successively added thereto while stirring at 0° C., followed by stirring at room temperature for 4 hours. After cooling the reaction solution, a 10% aqueous ammonium chloride solution was added to the reaction solution, and the mixture was extracted with ethyl acetate. The organic layer thus obtained was washed with a saturated aqueous sodium chloride solution and then dried over anhydrous sodium sulfate. The solvent was evaporated under reduced pressure, and the resulting residue was purified by silica gel thin layer chromatography (a developing solvent; hexane:ethyl acetate= 2.5:1 (v/v)) to yield 31 mg of the titled compound.

$^1$H-NMR (CDCl$_3$/TMS) δ(ppm): 8.12(2H, d, J=7 Hz), 7.60(1H, t, J=7 Hz), 7.47(2H, t, J=7 Hz), 5.78(1H, m), 5.60(1H, d, J=7 Hz), 5.09(1H, dd, J=1 Hz, 17 Hz), 5.02(1H, dd, J=1 Hz, 10 Hz), 4.92(1H, dd, J=1 Hz, 9 Hz), 4.83(1H, br), 4.54(1H, dd, J=7 Hz, 11 Hz), 4.30(1H, d, J=8 Hz), 4.17(1H, d, J=8 Hz), 4.04(1H, d, J=7 Hz), 3.90(1H, dd, J=4

Hz, 10 Hz), 2.79(1H, m), 2.56(2H, t, J=7 Hz), 2.45–2.6(2H, m), 2.24(2H, m), 1.92(3H, d, J=1 Hz), 1.88(1H, m), 1.78 (2H, m), 1.63(3H, s), 1.13(3H, s), 1.07(3H, s), 1.05(3H, t, J=7 Hz), 0.96(9H, t, J=8 Hz), 0.57(6H, m).

Step 3: 10-Allyl-4-O-butanoyl-13-O-[(2R,3S)-3-(tert-butoxycarbonylamino)-2-triethylsilyloxy-3-phenylpropionyl]-10-deacetoxy-4-deacetyl-7-O-triethylsilylbaccatin III The compound obtained in the above Step 2 was condensed with (3R,4S)-1-tert-butoxycarbonyl-4-phenyl-3-(triethylsilyloxy)azetidin-2-one in the same manner as in Step 4 of Example 16 to yield the titled compound.

$^1$H-NMR (CDCl$_3$/TMS) δ(ppm): 8.14(2H, d, J=7 Hz), 7.59(1H, t, J=7 Hz), 7.48(2H, t, J=7 Hz), 7.2–7.4(5H, m), 6.20(1H, br), 5.78(1H, m), 5.67(1H, d, J=7 Hz), 5.47(1H, br-d, J=9 Hz), 5.39(1H, br-d, J=9 Hz), 5.10(1H, dd, J=1 Hz, J=17 Hz), 5.04(1H, dd, J=1 Hz, 10 Hz), 4.91(1H, dd, J=2 Hz, 10 Hz), 4.53(1H, br-s), 4.53(1H, dd, J=6 Hz, 11 Hz), 4.31(1H, d, J=8 Hz), 4.21(1H, d, J=8 Hz), 3.99(1H, d, J=7 Hz), 3.85(1H, dd, J=4 Hz, 10 Hz), 2.83(2H, m), 2.61(1H, td, J=7 Hz, 15 Hz), 2.43–2.55(2H, m), 2.38(1H, m), 2.15(1H, m), 1.75–2.0(3H, m), 1.75(3H, s), 1.65(3H, s), 1.32(9H, s), 1.24(3H, s) 1.16(3H, s) 1.05(3H, t, J=7 Hz), 0.96(9H, m), 0.78(9H, t, J=8 Hz), 0.58(6H, m), 0.41(6H, m).

Step 4: 4-O-Butanoyl-13-O-[(2R,3S)-3-(tert-butoxycarbonylamino)-2-hydroxy-3-phenylpropionyl]-10-deacetoxy-4-deacetyl-10-(2-morpholinoethyl)baccatin III The compound obtained in the above Step 3 was reacted in the same manner as in Step 1 of Example 17, followed by purification. The resulting compound was reacted in the same manner as in Step 1 of Example 18, followed by purification. Then, the resulting compound was reacted in the same manner as in Step 1 of Example 19 except for using morpholine in place of dimethylamine, followed by purification. Finally, the resulting compound was reacted in the same manner as in Step 5 of Example 16, followed by purification to yield the titled compound.

Melting Point: 131°–136° C. (A dioxane solution was freeze-dried.)

$^1$H-NMR (CDCl$_3$/TMS) δ(ppm): 8.13(2H, d, J=7 Hz), 7.62(1H, t, J=7 Hz), 7.50(2H, t, J=7 Hz), 7.35–7.44(4H, m), 7.31(1H, m), 6.13(1H, br), 5.64(1H, d, J=7 Hz), 5.30(1H, d, J=9 Hz), 5.23(1H, br-d, J=9 Hz), 4.95(1H, dd, J=2 Hz, 10 Hz), 4.59(1H, br-s), 4.47(1H, dd, J=6 Hz, 11 Hz), 4.30(1H, d, J=8 Hz), 4.20(1H, d, J=8 Hz), 4.01(1H, dd, J=2 Hz, 9 Hz), 3.95(1H, d, J=7 Hz), 3.67(4H, m), 1.77(3H, s), 1.62(3H, s), 1.33(9H, s), 1.21(3H, s), 1.11(3H, s), 0.95(3H, t, J=7 Hz).

EXAMPLE 25

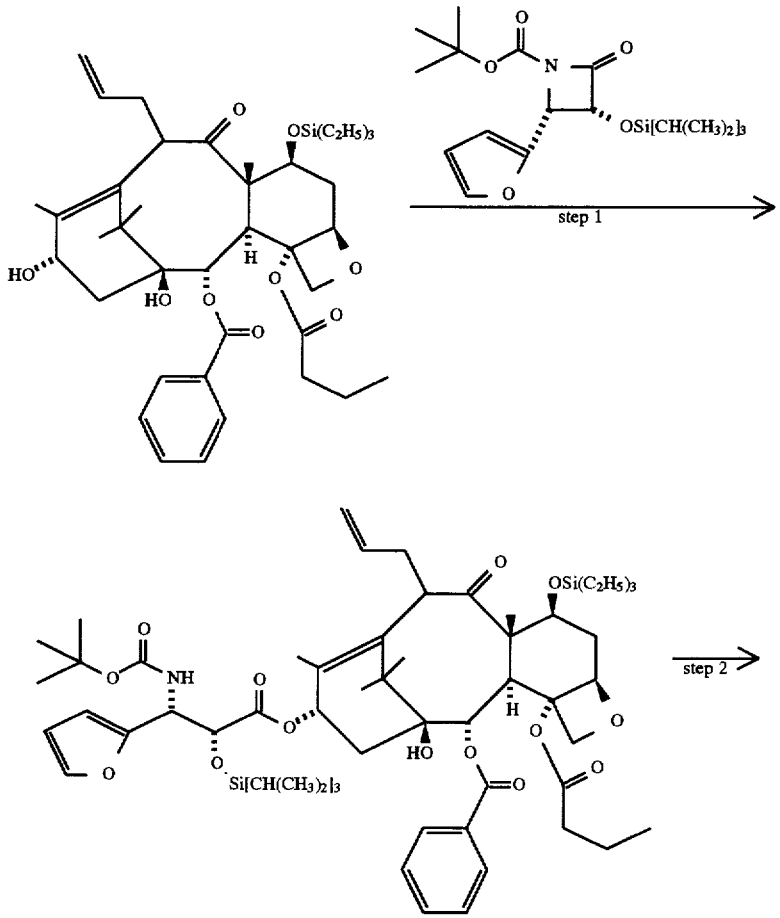

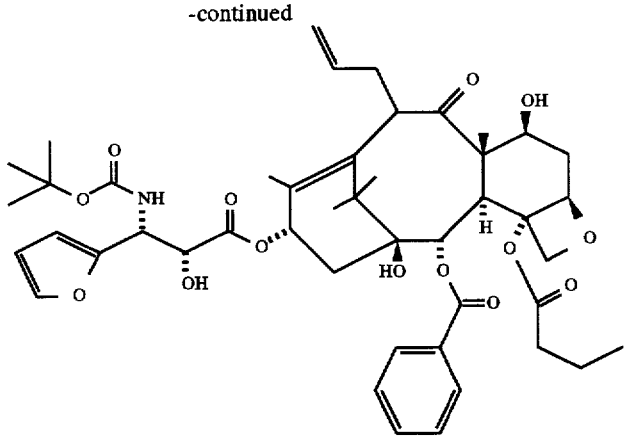

Step 1: 10-Allyl-4-O-butanoyl-13-O-[3-(tert-butoxycarbonylamino)-2-triisopropylsilyloxy-3-(2-furyl)propionyl]-10-deacetoxy-4-deacetyl-7-O-triethylsilylbaccatin III 14.5 mg of the compound obtained in Step 2 of Example 24 and 30.7 mg of (3R,4S)-1-(tert-butoxycarbonyl)-4-(2-furyl)-3-(triisopropylsilyloxy)azetidin-2-one were dissolved in 1 ml of dried tetrahydrofuran, and the solution was cooled to −60° C. Then, 0.082 ml of sodium bis(trimethylsilyl)amide (a 1M tetrahydrofuran solution) was added dropwise thereto, followed by stirring for 25 minutes. A saturated aqueous ammonium chloride solution was added to the reaction solution, and the mixture was extracted with ethyl acetate. The extract was washed with a saturated aqueous sodium chloride solution, dried over anhydrous sodium sulfate, and the solvent was evaporated under reduced pressure. The resulting residue was purified by silica gel thin layer chromatography (a developing solvent; hexane:ethyl acetate=6:1) to yield 18.8 mg of the titled compound as a colorless syrup material.

$^1$H-NMR (CDCl$_3$/TMS) δ(ppm): 0.57(6H, m), 0.84–1.07 (33H, m), 1.16(3H, s), 1.21(3H, s), 1.32(9H, s), 1.63(3H, s), 1.78(3H, s), 1.75–1.95(3H, s), 2.21(1H, dd, J=10 Hz, 15 Hz), 2.36(1H, dd, J=10 Hz, 15 Hz), 2.42–2.63(3H, m), 2.71–2.88(2H, m), 3.86(1H, dd, J=5 Hz, 10 Hz), 3.98(1H, d, J=7 Hz), 4.20(1H, d, J=8.5 Hz), 4.29(1H, d, J=8.5 Hz), 4.52(1H, dd, J=11 Hz, 7 Hz), 4.90(1H, d, J=9 Hz), 4.97(1H, s), 5.02(1H, br-d, J=9.5 Hz), 5.09(1H, d, J=18 Hz), 5.24(1H, d, J=10 Hz), 5.31(1H, d, J=10 Hz), 5.64(1H, d, J=7 Hz), 5.71–5.84(1H, m), 6.15(1H, t, J=8.5 Hz), 6.26(1H, d, J=4 Hz), 6.30–6.40(2H, m), 7.37(1H, s), 7.47(2H, t, J=8 Hz), 7.57(1H, t, J=8 Hz), 8.12(2H, d, J=8 Hz).

Step 2: 10-Allyl-4-O-Butanoyl-13-O-[3-(tert-butoxycarbonylamino)-3-(2-furyl)-2-hydroxypropionyl]-10-deacetoxy-4-deacetylbaccatin III The compound obtained in the above Step 1 was reacted in the same manner as in Step 5 of Example 16, followed by purification to yield the titled compound.

Melting Point: 127°–129° C. (A dioxane solution was freeze-dried).

$^1$H-NMR (CDCl$_3$/TMS) δ(ppm): 0.98(3H, t, J=7.5 Hz), 1.15(3H, s), 1.22(3H, s), 1.33(9H, s), 1.59(3H, s), 1.78(3H, s), 1.65–1.90(3H, m), 2.17–2.43(3H, m), 2.50–2.73(3H, m), 2.89–3.00(1H, m), 3.27(1H, br), 3.89(1H, d, J=7.5 Hz), 4.03(1H, d, J=7.5 Hz), 4.21(1H, d, J=8.5 Hz), 4.31(1H, d, J=8.5 Hz), 4.35(1H, br), 4.69(1H, br), 4.90(1H, dd, J=2 Hz, 10 Hz), 5.01(1H, dd, J=1 Hz, 10 Hz), 5.10(1H, dd, J=1.5 Hz, 17 Hz), 5.18(1H, br-d, J=10 Hz), 5.32(1H, br-d, J=7.5 Hz), 5.68(1H, d, J=7.5 Hz), 5.71–5.85(1H, m), 6.18(1H, br-t, J=8.5 Hz), 6.34(1H, d, J=3.5 Hz), 6.38(1H, dd, J=2 Hz, 3 Hz), 7.41(1H, s), 7.49(2H, t, J=7.5 Hz), 7.60(1H, t, J=7.5 Hz), 8.13(2H, d, J=7.5 Hz).

MS-FAB: 850(MH$^+$)

EXAMPLE 26

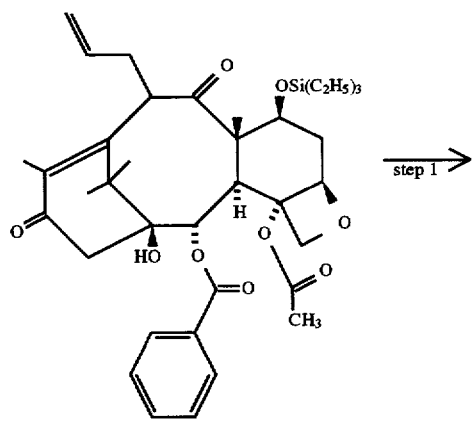

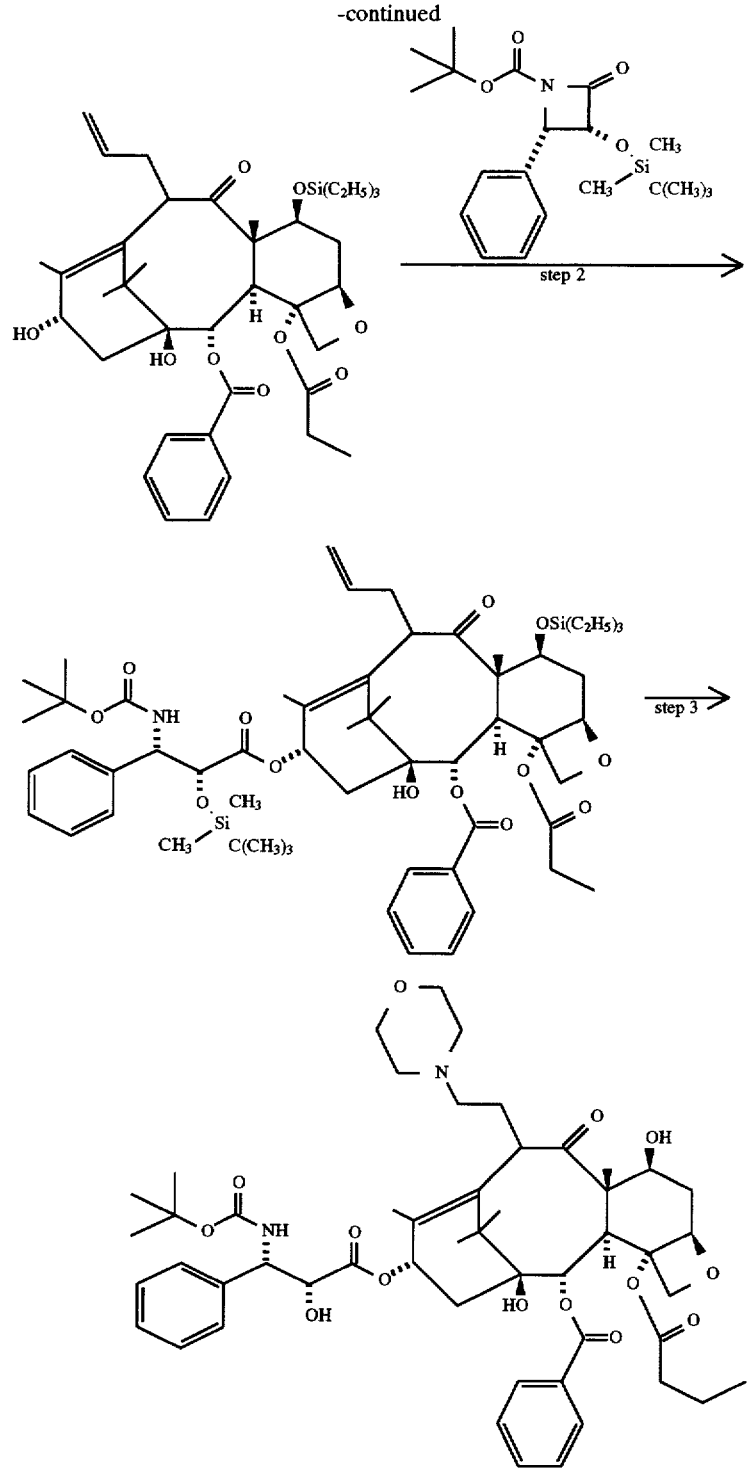

Step 1: 10-Allyl-10-deacetoxy-4-deacetyl-4-O-propanoyl-7-O-triethylsilylbaccatin III The compound obtained in Step 1 of Example 24 was reacted in the same manner as in Step 2 of Example 24 except for using ethyl iodide in place of methyl iodide, followed by purification, and subsequently the product was reduced with sodium borohydride in the same manner as in Step 2 of Example 24 to yield the titled compound.

$^1$H-NMR (CDCl$_3$/TMS) δ(ppm): 0.57(m, 6H), 0.93(m, 9H), 1.06(s, 3H), 1.12(s, 3H), 1.25(m, 3H), 1.62(s, 3H), 1.86(m, 1H), 1.90(s, 3H), 2.22(m, 2H), 2.50(m, 2H), 2.56(m, 2H), 2.77(m, 1H), 3.90(dd, 1H, J=4.5 Hz, 10.5 Hz), 4.05(d, 1H, J=7 Hz), 4.18(d, 1H, J=8.5 Hz), 4.28(d, 1H, J=8.5 Hz), 4.62(dd, 1H, J=6.5 Hz, 10.5 Hz), 4.82(m, 1H), 4.90(d, 1H, J=8 Hz), 5.00(dd, 1H, J=1 Hz, J=10 Hz), 5.05(dd, 1H, J=1 Hz, J=9 Hz), 5.59(d, 1H, J=7 Hz), 5.77(dd, 1H, J=1 Hz, J=17 Hz), 7.43(t, 2H, J=7.5 Hz), 7.59(t, 1H, J=7.5 Hz), 8.10(d, 2H, J=7.5 Hz).

MASS-FAB: 696(M$^+$)

Step 2: 10-Allyl-13-O-[(2R,3S)-3-(tert-butoxycarbonylamino)-2-(tert-butyldimethylsilyloxy)-3-phenylpropionyl]-10-deacetoxy-4-deacetyl-4-O-propionyl-7-O-triethylsilylbaccatin III The compound obtained in Step 1 above was condensed with (3R,4S)-1-(tert-butoxycarbonyl)-4-phenyl-3-(tert-butyldimethylsilyloxy)azetidin-2-one in the same manner as in Step 4 of Example 16 to yield the titled compound.

$^1$H-NMR (CDCl$_3$/TMS) δ(ppm): −0.31(s, 3H), −0.11(s, 3H), 0.57(m, 6H), 0.75(s, 9H), 0.95(m, 9H), 1.16(s, 3H), 1.23(m, 3H), 1.32(br-s, 9H), 1.40(t, 3H, J=7.5 Hz), 1.65(s, 3H), 1.75(s, 3H), 1.90(m, 1H), 2.30–2.35(m, 3H), 2.82(m, 2H), 3.84(dd, 1H, J=4.5 Hz, 10.5 Hz), 3.98(m, 1H), 4.21(d, 1H, J=8.5 Hz), 4.32(d, 1H, J=8.5 Hz), 4.48(s, 1H), 4.53(m, 1H), 4.90(d, 1H, J=8 Hz), 5.03(m, 1H), 5.09(m, 1H), 5.26(m, 1H), 5.43(m, 1H), 5.69(d, 1H, J=7 Hz), 5.78(m, 1H, 6.22(t, 1H, J=6 Hz), 7.28(m, 3H), 7.37(m, 2H), 7.47(t, 2H, J=7.5 Hz), 7.58(t, 1H, J=7.5 Hz), 8.12(d, 2H, J=7.5 Hz).

MASS-FAB: 1074(M$^+$)

Step 3: 13-O-[(2R,3S)-3-(tert-butoxycarbonylamino)-2-hydroxy-3-phenylpropionyl]-10-deacetoxy-4-deacetyl-10-(2-morpholinoethyl)-4-O-propionylbaccatin III The compound obtained in the above Step 2 was reacted in the same manner as in Step 1 of Example 17, followed by purification. The resulting compound was reacted in the same manner as in Step 1 of Example 18, followed by purification. Then, the resulting compound was reacted in the same manner as in Step 1 of Example 19 except for using morpholine in place of dimethylamine, followed by purification. Finally, the resulting compound was reacted in the same manner as in Step 5 of Example 16, followed by purification to yield the titled compound.

Melting Point: 175°–180° C.

$^1$H-NMR (CDCl$_3$/TMS) δ(ppm): 1.11(s, 3H), 1.23(m, 6H), 1.32(br-s, 9H), 1.62(s, 3H), 1.78(s, 3H), 1.88(m, 1H), 2.20(m, 1H), 2.30(m, 2H), 2.38(m, 2H), 2.53(m, 4H), 2.66(m, 4H), 3.92(d, 1H, J=7 Hz), 4.00(d, 1H, J=7 Hz), 4.20(d, 1H, J=8.5 Hz), 4.30(d, 1H, J=8.5 Hz), 4.48(dd, 1H, J=7 Hz, 11 Hz), 4.60(s, 1H), 4.96(d, 1H, J=8 Hz), 5.23(m, 1H), 5.29(m, 1H), 5.64(d, 1H, J=7 Hz), 6.16(m, 1H), 7.40(m, 5H), 7.49(t, 2H, J=7.5 Hz), 7.61(t, 2H, J=7.5 Hz), 8.13(d, 2H, J=7.5 Hz).

IR(KBr): 3796, 3456, 2976, 2936, 1716, 1604, 1586, 1496, 1454, 1396, 1368, 1316.

MASS-FAB: 919(M$^+$)

EXAMPLE 27

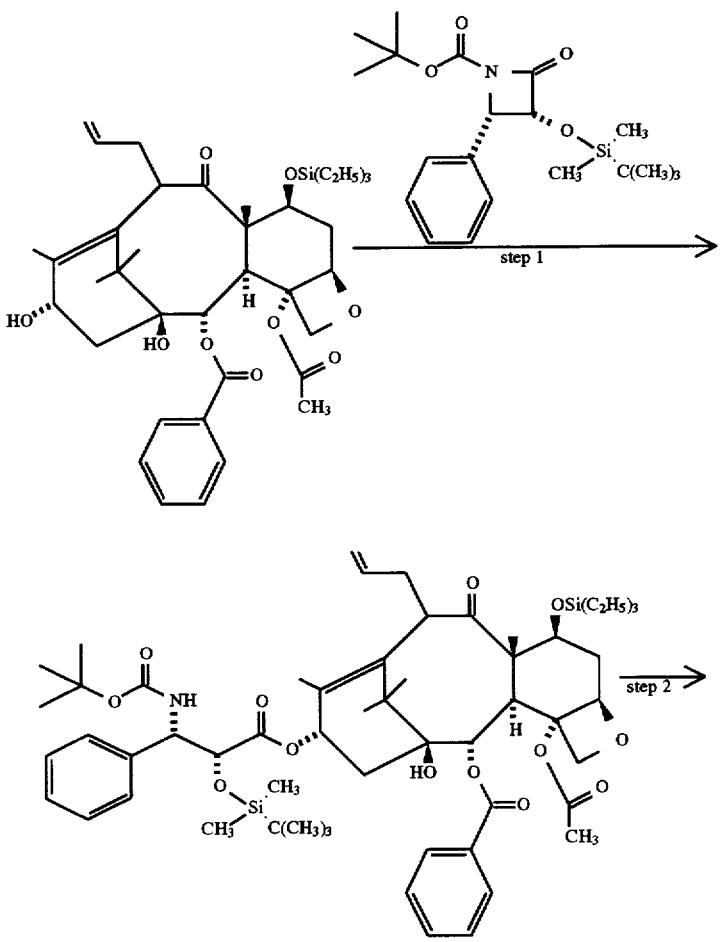

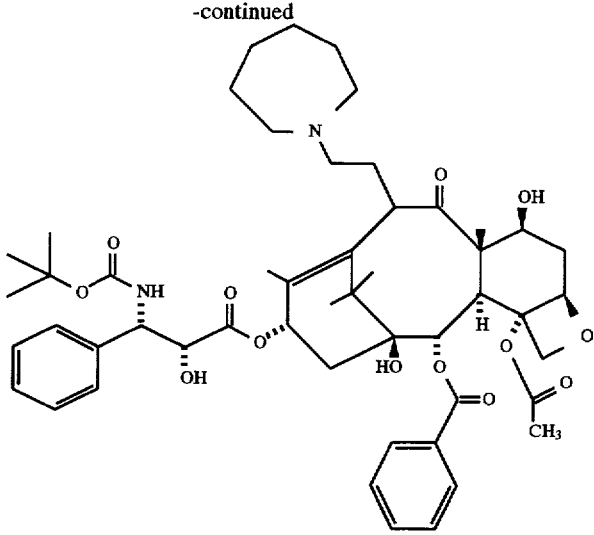

Step 1: 10-Allyl-13-O-[(2R,3S)-3-(tert-butoxycarbonylamino)-2-(tert-butyldimethylsilyloxy)-3-phenylpropionyl]-10-deacetoxy-7-O-triethylsilylbaccatin III The compound obtained in Step 3 of Example 16 was reacted with (3R,4S)-1-tert-butoxycarbonyl-4-phenyl-3-(tert-butyldimethylsilyloxy)azetidin-2-one in the same manner as in Step 4 of Example 16 to yield the titled compound.

$^1$H-NMR (CDCl$_3$/TMS) δ(ppm): −0.31(3H, s), −0.11(3H, s), 0.57(6H, m), 0.75(9H, s), 0.95(9H, m), 1.16(3H, s), 1.23(3H, m), 1.32(9H, br-s), 1.65(3H, s), 1.75(3H, s), 1.90 (1H, m), 2.30–2.35(6H, m), 2.82(2H, m), 3.84(1H, dd, J=4.5 Hz, 10.5 Hz), 3.98(1H, m), 4.21(1H, d, J=8.5 Hz), 4.32(1H, d, J=8.5 Hz), 4.48(1H, s), 4.53(1H, m), 4.90(1H, d, J=8 Hz), 5.03(1H, m), 5.09(1H, m), 5.26(1H, m), 5.43(1H, m), 5.69 (1H, d, J=7 Hz), 5.78(1H, m), 6.22(1H, t, J=6 Hz), 7.28(3H, m), 7.37(2H, m), 7.47(2H, t, J=7.5 Hz), 7.58(1H, t, J=7.5 Hz), 8.12(2H, d, J=7.5 Hz).

MASS-FAB: 1060(M$^+$).

Step 2: 13-O-[(2R,3S)-3-(tert-Butoxycarbonylamino)-2-hydroxy-3-phenylpropionyl]-10-deacetoxy-10-[(2-(1-hexamethyleneimino)ethyl]baccatin III The compound obtained in the above Step 1 was reacted in the same manner as in Step 1 of Example 17, followed by purification. The resulting compound was reacted in the same manner as in Step 1 of Example 18, followed by purification. Then, the resulting compound was reacted in the same manner as in Step 1 of Example 19 except for using hexamethyleneimine in place of dimethylamine, followed by purification. Finally, the resulting compound was reacted in the same manner as in Step 5 of Example 16, followed by purification to yield the titled compound.

Melting Point: 155°–160° C.

$^1$H-NMR (CDCl$_3$/TMS) δ(ppm) 1.11(3H, s), 1.12(3H, s), 1.32(9H, br-s), 1.62(3H, s), 1.68(6H, m), 1.87(5H, m), 1.88(3H, s), 2.20(1H, m), 2.30(2H, m), 2.37(3H, s), 2.49 (1H, m), 2.60(1H, m), 2.90–3.10(6H, br-m), 3.52(1H, m), 3.95(1H, d, J=7 Hz), 4.19(1H, d, J=8.5 Hz), 4.23(1H, m), 4.28(1H, d, J=8.5 Hz), 4.51(1H, dd, J=7 Hz, 11 Hz), 4.60 (1H, s), 4.96(1H, d, J=8 Hz), 5.26(1H, m), 5.42(1H, m), 5.62 (1H, d, J=7 Hz), 6.17(1H, m), 7.31–7.38(5H, m), 7.49(2H, t, J=7.5 Hz), 7.61(1H, t, J=7.5 Hz), 8.13(2H, d, J=7.5 Hz).

MASS-FAB: 915(M$^+$)

IR(KBr): 3840, 3668, 3304, 2936, 2868, 1962, 1860, 1714, 1606, 1496.

EXAMPLE 28

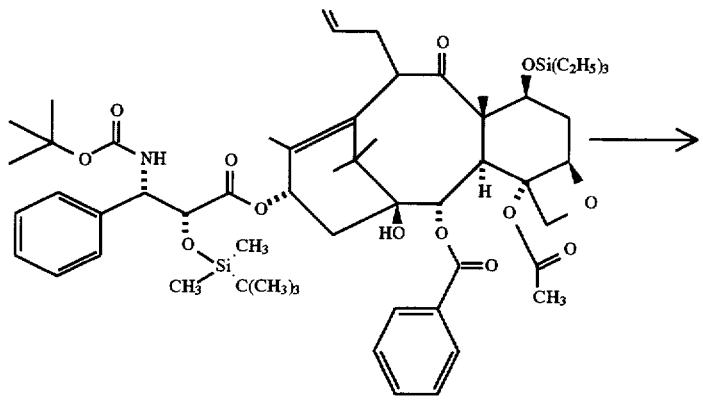

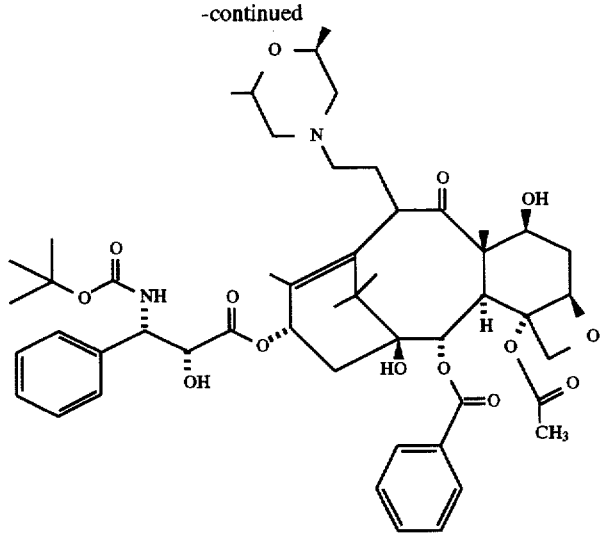

Step 1: 13-O-[(2R,3S)-3-(tert-Butoxycarbonylamino)-2-hydroxy-3-phenylpropionyl]-10-deacetoxy-10-[(2-(cis-2,6-dimethylmorpholino)ethyl]baccatin III The compound obtained in Step 1 of Example 27 was reacted in the same manner as in Step 1 of Example 17, followed by purification. The resulting compound was reacted in the same manner as in Step 1 of Example 18, followed by purification. Then, the resulting compound was reacted in the same manner as in Step 1 of Example 19 except for using cis-2,6-dimethylmorpholine in place of dimethylamine, followed by purification. Finally, the resulting compound was reacted in the same manner as in Step 5 of Example 16, followed by purification to yield the titled compound.

Melting Point: 135°–140° C.

$^1$H-NMR (CDCl$_3$/TMS) δ(ppm): 1.11(3H, s), 1.16(1H, d, J=7 Hz), 1.21(3H, s), 1.32(9H, s), 1.62(3H, s), 1.78(6H, m), 1.87(1H, m), 2.15–2.35(7H, m), 2.37(3H, s), 2.49(1H, m), 2.60(1H, m), 2.72–2.90(2H, m), 3.62(2H, m), 3.92(1H, d, J=7 Hz), 4.00(1H, d, J=7 Hz), 4.19(1H, d, J=8.5 Hz), 4.29(1H, d, J=8.5 Hz), 4.42(1H, dd, J=7 Hz, 11 Hz), 4.60 (1H, s), 5.00(1H, d, J=8 Hz), 5.28(1H, m), 5.38(1H, d, J=9 Hz), 5.62(1H, d, J=6 Hz), 6.18(1H, m), 7.31–7.42(5H, m), 7.49(2H, t, J=7.5 Hz), 7.61(1H, t, J=7.5 Hz), 8.11(2H, d, J=7.5 Hz).

MASS-FAB: 933(M$^+$)

IR(KBr): 3448, 2976, 2936, 2348, 1714, 1604, 1496, 1454.

EXAMPLE 29

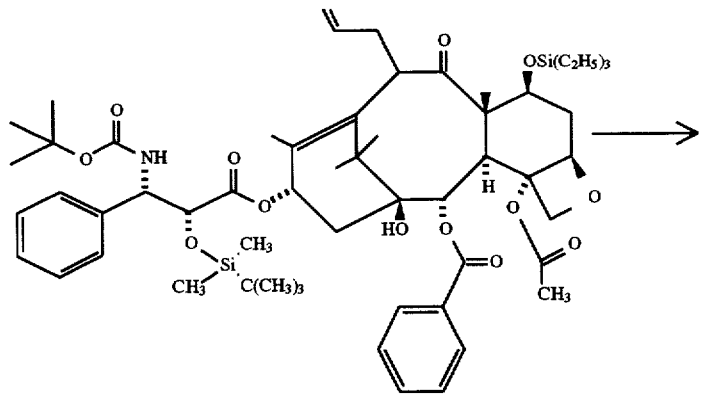

-continued

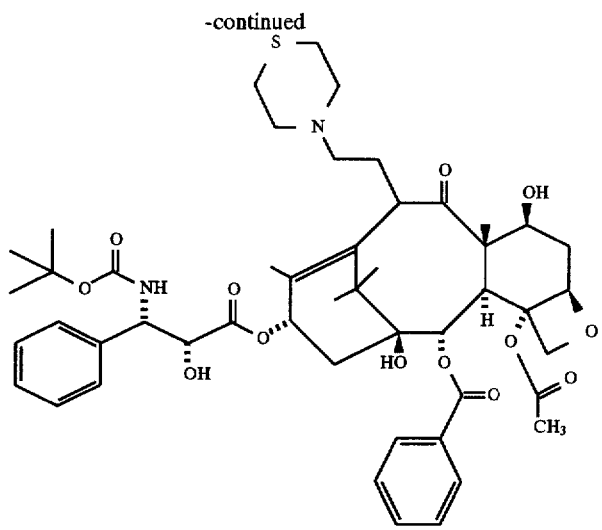

Step 1: 13-O-[(2R,3S)-3-(tert-Butoxycarbonylamino)-2-hydroxy-3-phenylpropionyl]-10-deacetoxy-10-(2-thiomorpholinoethyl)baccatin III The compound obtained in Step 1 of Example 27 was reacted in the same manner as in Step 1 of Example 17, followed by purification. The resulting compound was reacted in the same manner as in Step 1 of Example 18, followed by purification. Then, the resulting compound was reacted in the same manner as in Step 1 of Example 19 except for using thiomorpholine in place of dimethylamine, followed by purification. Finally, the resulting compound was reacted in the same manner as in Step 5 of Example 16, followed by purification to yield the titled compound.

Melting Point: 155°–160° C.

$^1$H-NMR (CDCl$_3$/TMS) δ(ppm): 1.09(3H, s), 1.21(3H, s), 1.32(9H, s), 1.62(3H, s), 1.78(3H, s), 1.87(1H, m), 2.19(1H, m), 2.36(5H, m), 2.37(3H, s), 2.49(1H, m), 2.68(6H, m), 2.78(2H, m), 3.94(2H, m), 4.19(1H, d, J=8.5 Hz), 4.29(1H, d, J=8.5 Hz), 4.42(1H, dd, J=7 Hz, 11 Hz), 4.60(1H, s), 4.98(1H, d, J=8 Hz), 5.24(1H, m), 5.36(1H, m), 5.62(1H, d, J=6 Hz), 6.17(1H, m), 7.31–7.37(5H, m), 7.47(2H, t, J=7.5 Hz), 7.61(1H, t, J=7.5 Hz), 8.11(2H, d, J=7.5 Hz).

MASS-FAB: 920(M$^+$)

IR(KBr): 3448, 2976, 1982, 1714, 1608, 1496, 1454, 1372, 1316, 1248, 1170, 1109, 1070.

EXAMPLE 30

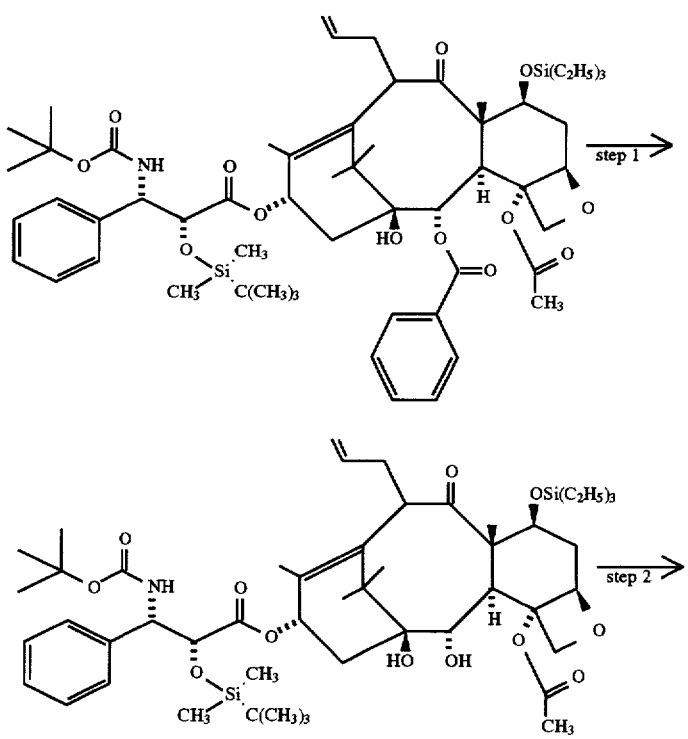

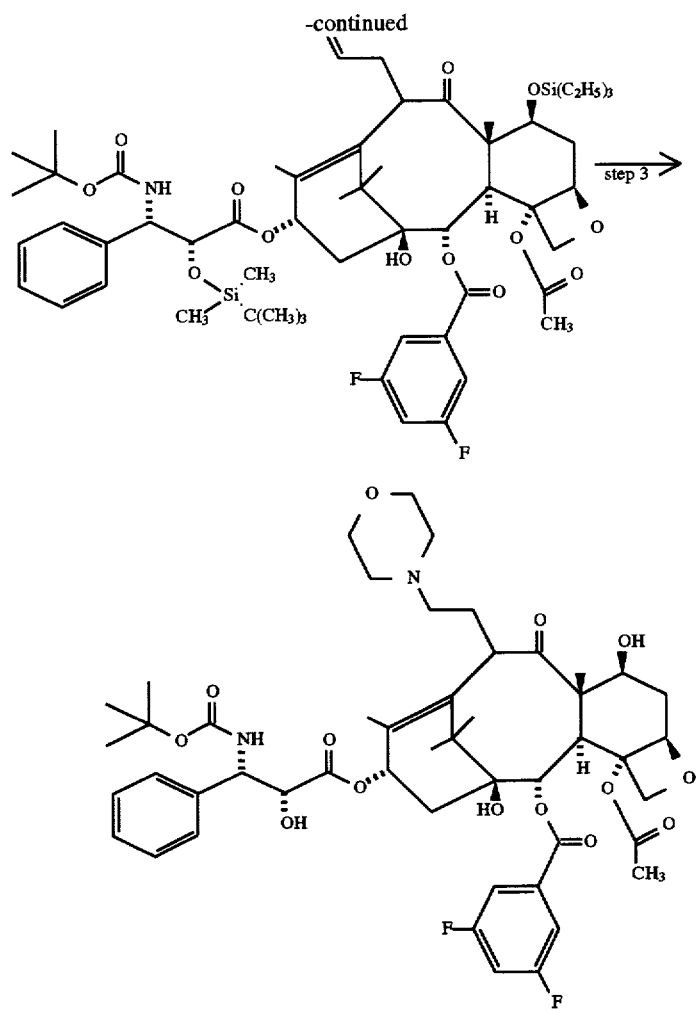

Step 1: 10-Allyl-13-O-[(2R,3S)-3-(tert-Butoxycarbonylamino)-2-(tert-butyldimethylsilyloxy)-3-phenylpropionyl]-10-deacetoxy-2-debenzoyl-7-O-triethylsilylbaccatin III 95 mg of the compound obtained in Step 1 of Example 27 was dissolved in 3 ml of dried tetrahydrofuran, and 4.8 ml of water was added thereto. Then, 36 mg of potassium tert-butoxide was added thereto at −40° C., followed by stirring for 66 hours at 31 20° C. 3 ml of a saturated aqueous ammonium chloride solution was added thereto, and the resulting mixture was extracted with ethyl acetate. The extract was dried over anhydrous magnesium sulfate. After evaporation of the solvent under reduced pressure, the resulting residue was purified by silica gel thin layer chromatography (a developing solvent; chloroform:acetone= 95:5 (v/v)) to yield 17 mg of the titled compound.

$^1$H-NMR (CDCl$_3$/TMS) δ(ppm): −0.31(3H, s), −0.12(3H, s), 0.57(6H, m), 0.73(9H, s), 0.96(9H, m), 1.05(3H, s), 1.26(3H, s), 1.42(9H, s), 1.59(3H, s), 1.69(3H, s), 1.91(1H, m), 2.10(1H, m), 2.30(1H, m), 2.39(3H, s), 2.49(2H, m), 2.78(1H, m), 3.59(1H, d, J=7 Hz), 3.75(1H, dd, J=4 Hz, 10 Hz), 3.90(1H, m), 4.41(2H, m), 4.62(2H, AB type d, J=8.5 Hz), 4.97(1H, d, J=8 Hz), 5.01(1H, d, J=10 Hz), 5.07(1H, d, J=17 Hz), 5.21(1H, d, J=9 Hz), 5.48(1H, d, J=10 Hz), 5.73(1H, m), 6.20(1H, m), 7.27(1H, m), 7.38(1H, m), 7.32 (3H, m).

MASS-FAB: 957(M$^+$)

Step 2: 10-Allyl-13-O-[(2R,3S)-3-(tert-Butoxycarbonylamino)-2-(tert-butyldimethylsilyloxy)-3-phenylpropionyl]-10-deacetoxy-2-debenzoyl-2-O-(3,5-difluorobenzolyl)-7-O-triethylsilylbaccatin III 17 mg of the compound obtained in the above Step 1 was dissolved in 0.5 ml of dried tetrahydrofuran, and 11 μl of 3,5-difluorobenzoyl chloride and 89 μl of lithium hexamethyldisilazide (a 1.0M solution) were added thereto at −78° C., followed by stirring at that temperature for 15 minutes. The reaction was terminated by adding a saturated aqueous ammonium chloride solution, and the reaction mixture was extracted with ethyl acetate. The extract was dried over anhydrous magnesium sulfate. After evaporation of the solvent, the residue was purified by silica gel thin layer chromatography (a developing solvent; hexane:ethyl acetate=8:2 (v/v)) to yield 16 mg of the titled compound.

$^1$H-NMR (CDCl$_3$/TMS) δ(ppm): −0.31(3H, s), −0.12(3H, s), 0.57(6H, m), 0.73(9H, s), 0.96(9H, m), 1.14(3H, s), 1.26(3H, m), 1.30(9H, s), 1.62(3H, s), 1.74(3H, s), 1.91(1H, m), 2.10(1H, m), 2.30(1H, m), 2.49(2H, m), 2.53(3H, s), 2.82(1H, m), 3.83(1H, m), 4.00(1H, d, J=7 Hz), 4.19(1H, d, J=8.5 Hz), 4.32(1H, d, J=8.5 Hz), 4.50(2H, m), 4.98(1H, d, J=8 Hz), 5.05(2H, m), 5.30(1H, m), 5.42(1H, m), 5.61(1H, d, J=7 Hz), 5.76(1H, m), 6.23(1H, t, J=5 Hz), 7.05(1H, m), 7.25–7.39(5H, m), 7.66(2H, br-d, J=5 Hz).

MASS-FAB: 1096(M$^+$)

Step 3: 13-O-[(2R,3S)-3-(tert-Butoxycarbonylamino)-2-hydroxy-3-phenylpropionyl]-10-deacetoxy-2-debenzoyl-2-O-(3,5-difluorobenzoyl)-10-(2-morpholinoethyl)baccatin III The compound obtained in the above Step 2 was reacted in the same manner as in Step 1 of Example 17, followed by purification. The resulting compound was reacted in the same manner as in Step 1 of Example 18, followed by purification. The resulting compound was reacted in the same manner as in Step 1 of Example 19 except for using morpholine in place of dimethylamine, followed by purification. Finally, the resulting compound was reacted in the same manner as in Step 5 of Example 16, followed by purification to yield the titled compound.

$^1$H-NMR (CDCl$_3$/TMS) δ(ppm): 1.09(3H, s), 1.21(3H, s), 1.32(9H, s), 1.62(3H, s), 1.78(3H, s), 1.87(1H, m), 2.19(1H, m), 2.36(5H, m), 2.37(3H, s), 2.49(1H, m), 2.68(6H, m), 2.78(2H, m), 3.94(2H, m), 4.19(1H, d, J=8.5 Hz), 4.29(1H, d, J=8.5 Hz), 4.42(1H, dd, J=7 Hz, 11 Hz), 4.60(1H, s), 4.98(1H, d, J=8 Hz), 5.24(1H, m), 5.36(1H, m), 5.62(1H, d, J=6 Hz), 6.17(1H, m), 7.31–7.37(5H, m), 7.47(2H, t, J=7.5 Hz), 7.61(1H, t, J=7.5 Hz), 8.11(2H, d, J=7.5 Hz).

EXAMPLE 31

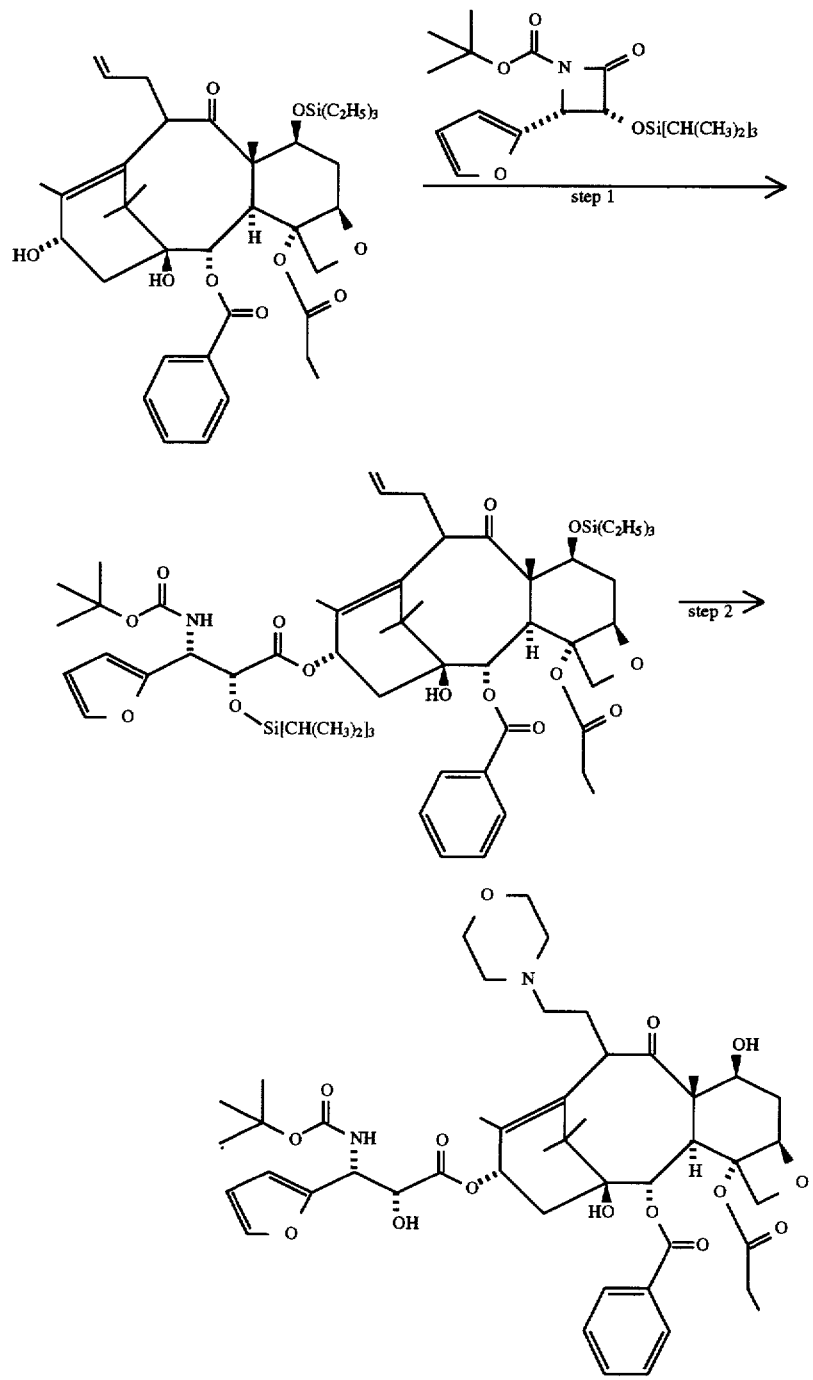

Step 1: 10-Allyl-13-O-[(2R,3S)-3-(tert-Butoxycarbonylamino)-3-(2-furyl)-2-(triisopropylsilyloxy)propionyl]-10-deacetoxy-4-deacetyl-4-O-propionyl-7-O-triethylsilylbaccatin III The compound obtained in Step 1 of Example 26 was reacted with (3R,4S)-1-(tert-butoxycarbonyl)-4-(2-furyl)-3-(triisopropylsilyloxy)azetidin-2-one in the same manner as in Step 4 of Example 16 to yield the titled compound.

$^1$H-NMR (CDCl$_3$/TMS) δ(ppm): 0.57(6H, m), 0.95(30H, m), 1.15(3H, s), 1.21(3H, s), 1.32(9H, s), 1.34(3H, m), 1.61(3H, s), 1.75(3H, s), 1.90(1H, m), 2.21(1H, m), 2.32(1H, m), 2.48(2H, m), 2.72(2H, m), 2.80(1H, m), 3.82(1H, m), 3.96(1H, d, J=7 Hz), 4.21(1H, d, J=8.5 Hz), 4.30(1H, d, J=8.5 Hz), 4.52(1H, dd, J=7 Hz, 11 Hz), 4.90(1H, d, J=7 Hz), 4.99(1H, m), 5.02(1H, d, J=10 Hz), 5.10(1H, d, J=17 Hz), 5.29(2H, m), 5.68(1H, d, J=7 Hz), 5.76(1H, m), 6.16(1H, t, J=6 Hz), 6.26(1H, d, J=3 Hz), 6.33(1H, m), 7.33(1H, s), 7.43(2H, t, J=7.5 Hz), 7.52(1H, m), 8.08(2H, d, J=7.5 Hz).

MASS-FAB: 1106(M$^+$)

Step 2: 13-O-[(2R,3S)-3-(tert-Butoxycarbonylamino)-3-(2-furyl)-2-hydroxypropionyl]-10-deacetoxy-4-deacetyl-10-(2-morpholinoethyl)-4-O-propionylbaccatin III The compound obtained in the above Step 1 was reacted in the same manner as in Step 1 of Example 17, followed by purification. The resulting compound was reacted in the same manner as in Step 1 of Example 18, followed by purification. Then, the resulting compound was reacted in the same manner as in Step 1 of Example 19 except for using morpholine in place of dimethylamine, followed by purification. Finally, the resulting compound was reacted in the same manner as in Step 5 of Example 16, followed by purification to yield the titled compound.

Melting Point: 140°–145° C.

$^1$H-NMR (CDCl$_3$/TMS) δ(ppm): 1.01(3H, s), 1.21(3H, s), 1.22(3H, m), 1.30(9H, s), 1.61(3H, s), 1.79(3H, s), 1.83(1H, m), 2.21(1H, m), 2.30–2.72(12H, m), 3.68(4H, br), 3.92(1H, d, J=7 Hz), 3.99(1H, m), 4.20(1H, d, J=8.5 Hz), 4.30(1H, d, J=8.5 Hz), 4.50(1H, dd, J=7 Hz, 11 Hz), 4.70(1H, s), 4.95(1H, d, J=7 Hz), 5.18(1H, d, J=7 Hz), 5.30(1H, d, J=7 Hz), 5.64(1H, d, J=6 Hz), 6.18(1H, m), 6.32(1H, d, J=3 Hz), 6.38(1H, m), 7.42(1H, s), 7.48(2H, t, J=7.5 Hz), 7.59(1H, t, J=7.5 Hz), 8.11(2H, d, J=7.5 Hz).

MASS-FAB: 909(M$^+$)

EXAMPLE 32

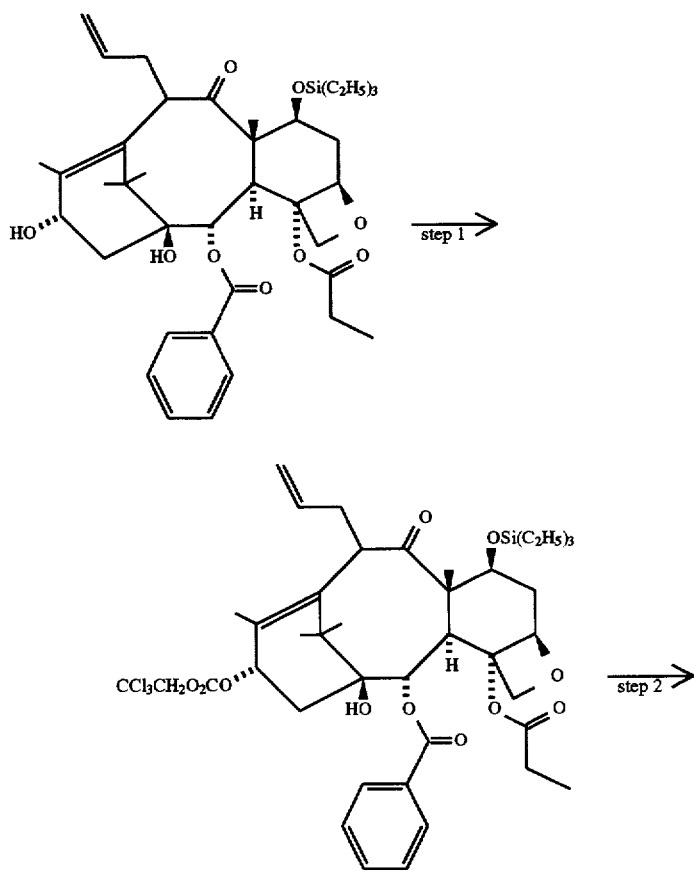

-continued
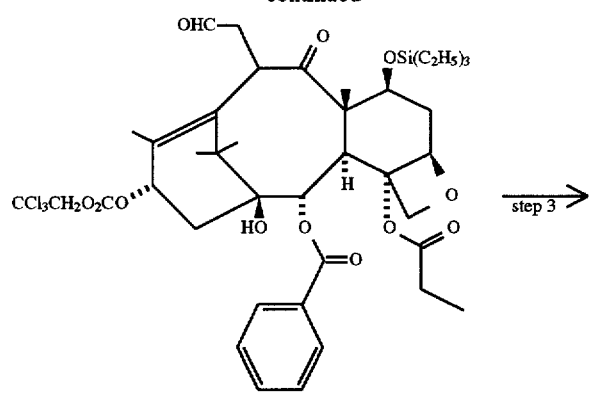
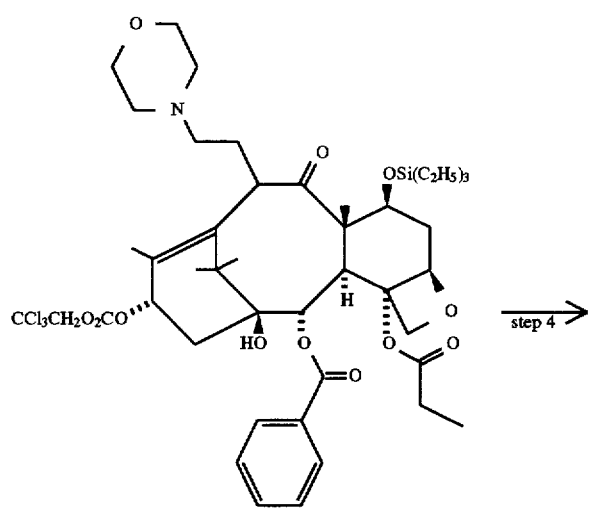
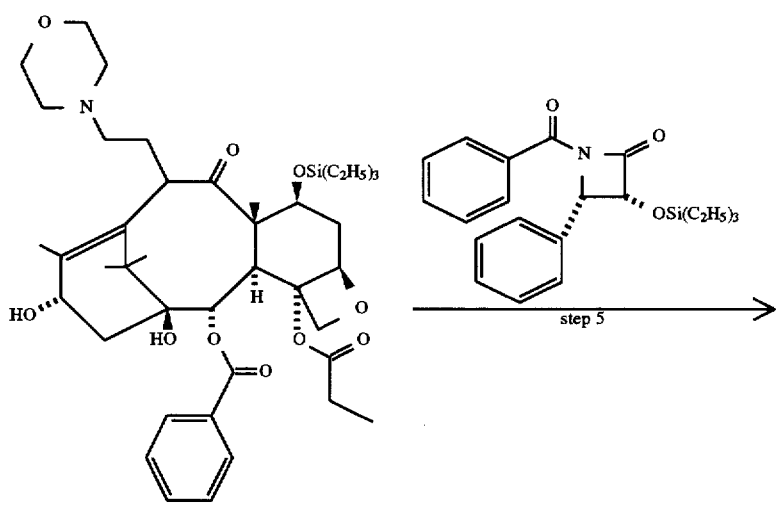

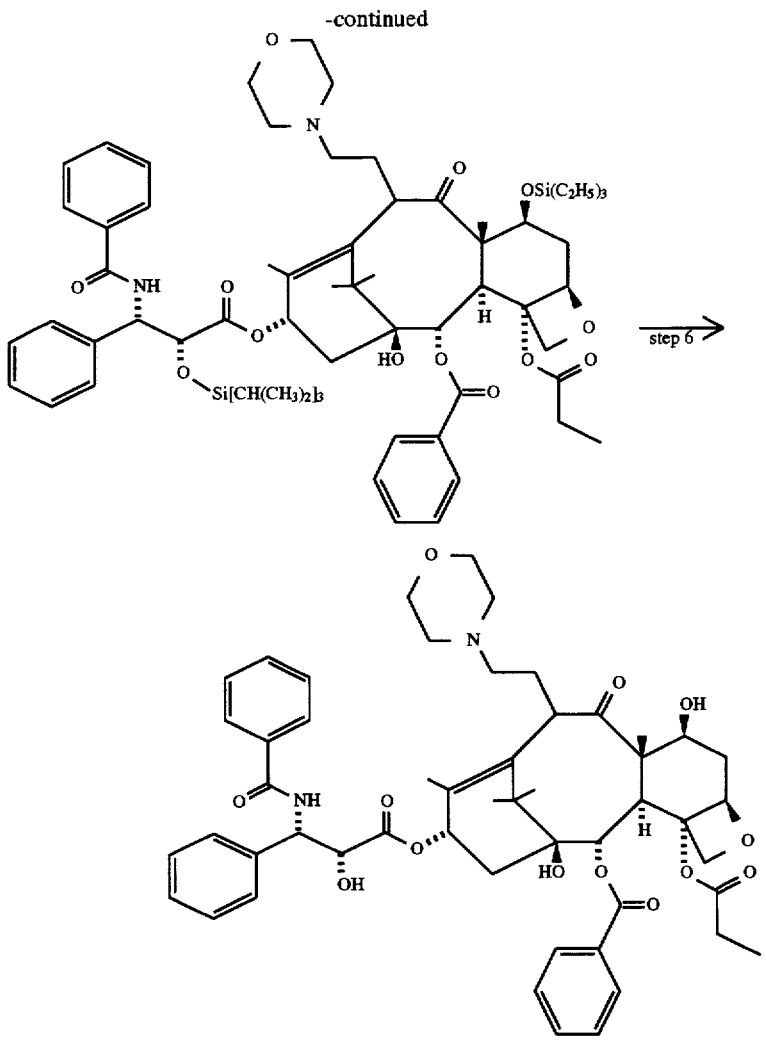

Step 1: 10-Allyl-10-deacetyl-4-O-propionyl-13-O-trichloroethoxycarbonyl-7-O-triethylsilylbaccatin III 118 mg of the compound obtained in Step 1 of Example 26 was dissolved in 3.5 ml of dried pyridine, and 0.11 ml of trichloroethoxycarbonyl chloride was added thereto, followed by reacting at 80° C. for 30 minutes. After allowing to cool to room temperature, ethyl acetate and water were added thereto to terminate the reaction. The reaction mixture was extracted three times with ethyl acetate, the extract was dried over anhydrous magnesium sulfate. The solvent was evaporated under reduced pressure, and the resulting residue was purified by silica gel thin layer chromatography (a developing solvent; chloroform:acetone=97:3 (v/v)) to yield 119 mg of the titled compound.

$^1$H-NMR (CDCl$_3$/TMS) δ(ppm): 0.56(6H, m), 0.99(9H, s), 1.14(3H, s), 1.32(3H, t, J=7.5 Hz), 1.62(3H, s), 1.82(3H, s), 1.88(1H, m), 2.32(1H, m), 2.50(2H, m), 2.68(3H, m), 2.80(1H, m), 3.98(1H, dd, J=4 Hz, 10 Hz), 4.00(1H, d, J=7 Hz), 4.12(1H, d, J=8 Hz), 4.29(1H, d, J=8 Hz), 4.65(1H, dd, J=7 Hz, 10 Hz), 4.82(2H, AB type d, J=12 Hz), 4.89(1H, d, J=8 Hz), 5.00(1H, d, J=10 Hz), 5.12(1H, d, J=17 Hz), 5.61(1H, d, J=7 Hz), 5.74(1H, m), 5.98(1H, t, J=8 Hz), 7.43(2H, t, J=7.5 Hz), 7.58(1H, t, J=7.5 Hz), 8.09(2H, d, J=7.5 Hz).

MASS-FAB: 873(M$^+$).

Step 2: 10-Deacetoxy-4-deacetyl-10-formylmethyl-4-O-propionyl-13-O-trichloroethoxycarbonyl-7-O-triethylsilylbaccatin III The compound obtained in the above Step 1 was reacted in the same manner as in Step 1 of Example 17, followed by purification. The resulting compound was reacted in the same manner in Step 1 of Example 18 to yield the titled compound.

$^1$H-NMR (CDCl$_3$/TMS) δ(ppm): 0.55(6H, m), 0.92(9H, t, J=7.5 Hz), 1.11(3H, s), 1.13(3H, s), 1.32(3H, t, J=7 Hz), 1.62(3H, s), 1.89(1H, m), 1.96(3H, s), 2.25–2.40(2H, m), 2.50–2.62(3H, m), 2.70(2H, m), 3.56(1H, dd, J=5 Hz, 10 Hz), 4.02(1H, d, J=7 Hz), 4.15(1H, d, J=8 Hz), 4.30(1H, d, J=8 Hz), 4.50(1H, m), 4.61(1H, dd, J=7 Hz, 11 Hz), 4.82(AB type d, 2H, J=12 Hz), 4.90(1H, d, J=8 Hz), 5.62(1H, d, J=7 Hz), 5.90(1H, m), 7.46(2H, t, J=7.5 Hz), 7.60(1H, t, J=7.5 Hz), 8.08(2H, d, J=7.5 Hz).

MASS-FAB: 875(M$^+$)

Step 3: 10-Deacetoxy-4-deacetyl-4-O-propionyl-10-(2-morpholinoethyl)-13-O-trichloroethoxycarbonyl-7-O-triethylsilylbaccatin III The compound obtained in the above Step 2 was reacted in the same manner as in Step 1 of Example 19 except for using morpholine in place of dimethylamine, followed by purification to yield the titled compound.

$^1$H-NMR (CDCl$_3$/TMS) δ(ppm): 0.56(6H, m), 0.93(9H, t, J=7.5 Hz), 1.12(6H, s), 1.32(3H, t, J=8 Hz), 1.61(3H, s), 1.86(1H, m), 1.93(3H, s), 2.30–2.52(10H, m), 2.70(2H, m), 3.70(4H, m), 3.86(1H, dd, J=5 Hz, 10 Hz), 4.02(1H, d, J=7

Hz), 4.16(1H, d, J=8 Hz), 4.30(1H, d, J=8 Hz), 4.56(1H, dd, J=7 Hz, 11 Hz), 4.82(2H, AB type d, J=12 Hz), 4.90(1H, m), 5.60(1H, d, J=7 Hz), 5.95(1H, m), 7.42(2H, t, J=7.5 Hz), 7.58(1H, t, J=7.5 Hz), 8.09(2H, d, J=7.5 Hz).

MASS-FAB: 944(M⁺)

Step 4: 10-Deacetoxy-4-deacetyl-4-O-propionyl-10-(2-morpholinoethyl)-7-O-triethylsilylbaccatin III 107 mg of the compound obtained in the above Step 3 was dissolved in a mixed solvent of 4 ml of acetic acid and 4 ml of methanol, and 800 mg of zinc powder was added thereto, followed by reacting at 60° C. for 1 hour. The reaction mixture was diluted with ethyl acetate, and the zinc powder was filtered. The filtrated was concentrated, dissolved in ethyl acetate and washed with a saturated aqueous sodium bicarbonate solution. After drying over anhydrous magnesium sulfate, the solvent was evaporated under reduced pressure, and the resulting residue was purified by silica gel thin layer chromatography (a developing solvent; chloroform:acetone=97:4 (v/v)) to yield 76 mg of the titled compound.

$^1$H-NMR (CDCl$_3$/TMS) δ(ppm): 0.57(6H, m), 0.96(9H, t, J=7.5 Hz), 1.04(3H, s), 1.10(3H, s), 1.22(3H, t, J=7 Hz), 1.61(3H, s), 1.88(1H, m), 1.98(3H, s), 2.22(1H, m), 2.37 (4H, m), 2.50(5H, br), 2.61(3H, m), 3.71(4H, m), 3.84(1H, m), 4.03(1H, d, J=7 Hz), 4.18(1H, d, J=8 Hz), 4.30(1H, d, J=8 Hz), 4.55(1H, dd, J=7 Hz, 11 Hz), 4.81(1H, t, J=8 Hz), 4.91(1H, d, J=7 Hz)), 5.59(1H, d, J=7 Hz), 7.46(2H, t, J=7.5 Hz), 7.59(1H, t, J=7.5 Hz), 8.11(2H, d, J=7.5 Hz).

MASS-FAB: 770(M⁺)

Step 5: 13-O-[(2R,3S)-3-(benzoylamino)-3-phenyl-2-(triethylsilyloxylpropionyl]-10-deacetoxy-4-deacetyl-10-(2-morpholinoethyl)-4-O-propionyl-7-O-triethylsilylbaccatin III 23 mg of the compound obtained in the above Step 4 and 23 mg of (3R,4S)-1-benzoyl-4-phenyl-3-(triethylsilyloxy)-azetindin-2-one were dissolved in 0.7 ml of dried tetrahydrofuran, and 121 µl of sodium hexamethyldisilazide (a 1.0M toluene solution) was added dropwise thereto at −78° C., followed by allowing the mixture to react for 15 minutes at that temperature. The reaction mixture was diluted with ethyl acetate, a saturated aqueous ammonium chloride solution was added thereto, and the mixture was extracted with ethyl acetate. The extract was dried over anhydrous magnesium sulfate and purified by silica gel thin layer chromatography (a developing solvent; chloroform:acetone, 90:10 (v/v)) to yield 14 mg of the titled compound.

$^1$H-NMR (CDCl$_3$/TMS) δ(ppm): 0.48(6H, m), 0.55(6H, m), 0.82(9H, m), 0.99(9H, m), 1.18(3H, s), 1.21(3H, s), 1.35 (3H, m), 1.62(3H, s), 1.85(3H, s), 1.95(1H, m), 2.15–2.50 (11H, m), 2.72–2.80(2H, m), 3.69(4H, br), 3.80(1H, m), 3.92(1H, m), 4.23(1H, m), 4.30(1H, d, J=8.5 Hz), 4.52(1H, m), 4.64(1H, s), 4.89(1H, m), 5.66(2H, m), 6.18(1H, m), 7.10(1H, d, J=8.5 Hz), 7.32–7.60(9H, m), 7.70(2H, m), 8.12(4H, m).

MASS-FAB: 1151(M⁺)

Step 6: 13-O-[(2R,3S)-3-(benzoylamino)-2-hydroxy-3-phenylpropionyl]-10-deacetoxy-4-deacetyl-10-(2-morpholinoethyl)-4-O-propionylbaccatin III 14 mg of the compound obtained in the above Step 5 was reacted in the same manner as in Step 5 of Example 16, followed by purification to yield 5 mg of the titled compound.

Melting Point: 130°–135° C.

$^1$H-NMR (CDCl$_3$/TMS) δ(ppm): 1.10(3H, s), 1.19(6H, m), 1.62(3H, s), 1.76(3H, s), 1.88(1H, m), 2.21–2.70(13H, m), 3.65(4H, br), 3.92(1H, d, J=7 Hz), 3.96(1H, m), 4.21 (1H, d, J=8.5 Hz), 4.30(1H, d, J=8.5 Hz), 4.47(1H, dd, J=7 Hz, 11 Hz), 4.78(1H, m), 4.92(1H, d, J=8 Hz), 5.65(1H, d, J=7 Hz), 5.76(1H, d, J=9 Hz), 6.18(1H, m), 6.88(1H, d, J=8.5 Hz), 7.35–7.50(10H, m), 7.58(1H, m), 7.70(2H, d, J=7 Hz), 8.15(2H, d, J=7 Hz).

MASS-FAB: 923(M⁺)

IR(KBr): 3452, 3068, 3036, 2936, 2860, 2824, 1974, 1730, 1668, 1604, 1582, 1516, 1486, 1454.

EXAMPLE 33

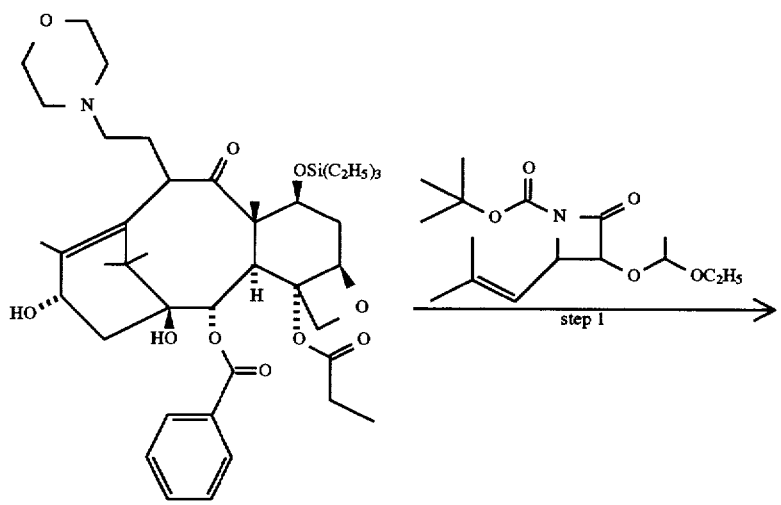

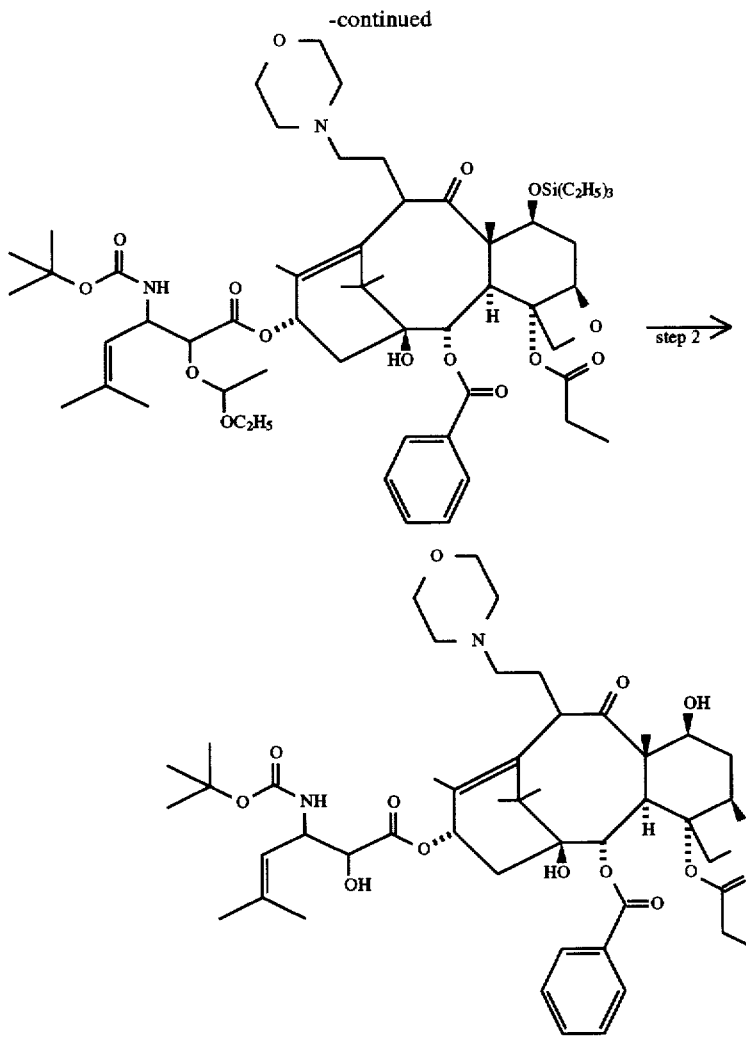

Step 1: 13-O-[3-(tert-Butoxycarbonylamino)-2[(1-ethoxy) ethoxy]-5-methyl-4-hexenoyl]-10-deacetoxy-4-deacetyl-10-(2-morpholinoethyl)-4-O-propionyl-7-O-triethylsilylbaccatin III 29 mg of the compound obtained in Step 4 of Example 32 was reacted with 36 mg of cis1-(tert-butoxycarbonyl)-4-isobutenyl-3-[(1-ethoxy)ethoxy]azetidin-2-one in the same manner as in Step 5 of Example 32, followed by purification to yield 25 mg of the titled compound.

$^1$H-NMR (CDCl$_3$/TMS) δ(ppm): 0.59(6H, m), 0.94(9H, m), 1.12(3H, s), 1.19(6H, br), 1.29–1.42(15H, m), 1.62–1.89 (13H, m), 2.10–2.70(13H, m), 3.70(4H, br), 7.42(2H, m), 7.55(1H, m), 8.05(2H, m).

MASS-FAB: 1083(M+).

Step 2: 13-O-[3-(tert-Butoxycarbonylamino)-2-hydroxy-5-methyl-4-hexenoyl]-10-deacetoxy-4-deacetyl-10-(2-morpholinoethyl)-4-O-propionylbaccatin III 25 mg of the compound obtained in the above Step 1 was reacted in the same manner as in Step 5 of Example 16, purified, and then reacted in the same manner as in Step 6 of Example 32, followed by purification to yield the titled compound (a low polarity isomer A=4 mg, and a high polarity isomer B=8 mg).

Isomer A

Melting Point: 105°–110° C.

$^1$H-NMR (CDCl$_3$/TMS) δ(ppm): 1.10(3H, s), 1.19(3H, s), 1.27(3H, m), 1.39(9H, s), 1.62(3H, s), 1.78(3H, s), 1.82(3H, s), 1.89(1H, m), 2.05(3H, s), 2.13(1H, m), 2.40–2.63(11H, m), 2.77(1H, m), 3.71(4H, br), 3.99(1H, d, J=7 Hz), 4.05 (1H, m), 4.06(1H, s), 4.20(1H, d, J=8.5 Hz), 4.30(1H, d, J=8.5 Hz), 4.52(1H, dd, J=7 Hz, 11 Hz), 4.78(2H, m), 4.97(1H, d, J=8 Hz), 5.30(1H, d, J=7 Hz), 5.64(1H, d, J=7 Hz), 5.95(1H, br), 7.47(2H, t, J=7.5 Hz), 7.61(1H, t, J=7.5 Hz), 8.07(2H, d, J=7.5 Hz).

MASS-FAB: 897(M+)

IR(Kbr): 3456, 2976, 2936, 2824, 1712, 1632, 1604, 1494, 1454, 1394, 1370.

Isomer B

Melting Point: 110°–115° C.

$^1$H-NMR (CDCl$_3$/TMS) δ(ppm): 1.12(3H, s), 1.22(3H, s), 1.25(3H, m), 1.32(9H, s), 1.62(3H, s), 1.79(6H, s), 1.82(3H, s), 1.89(1H, m), 2.08(1H, m), 2.40(1H, m), 2.60–2.70(11H, m), 3.69(4H, m), 3.96(1H, d, J=7 Hz), 4.00(1H, m), 4.18 (1H, s), 4.22(1H, d, J=8.5 Hz), 4.30(1H, d, J=8.5 Hz), 4.49(1H, dd, J=7 Hz, 11 Hz), 4.73(2H, m), 4.97(1H, d, J=8 Hz), 5.37(1H, br), 5.64(1H, d, J=7 Hz), 6.10(1H, br), 7.47 (2H, t, J=7.5 Hz), 7.61(1H, t, J=7.5 Hz), 8.12(2H, d, J=7.5 Hz).

MASS-FAB: 897(M+)

IR(Kbr): 3456, 2976, 2936, 2824, 1712, 1632, 1604, 1494, 1454, 1394, 1370.

EXAMPLE 34
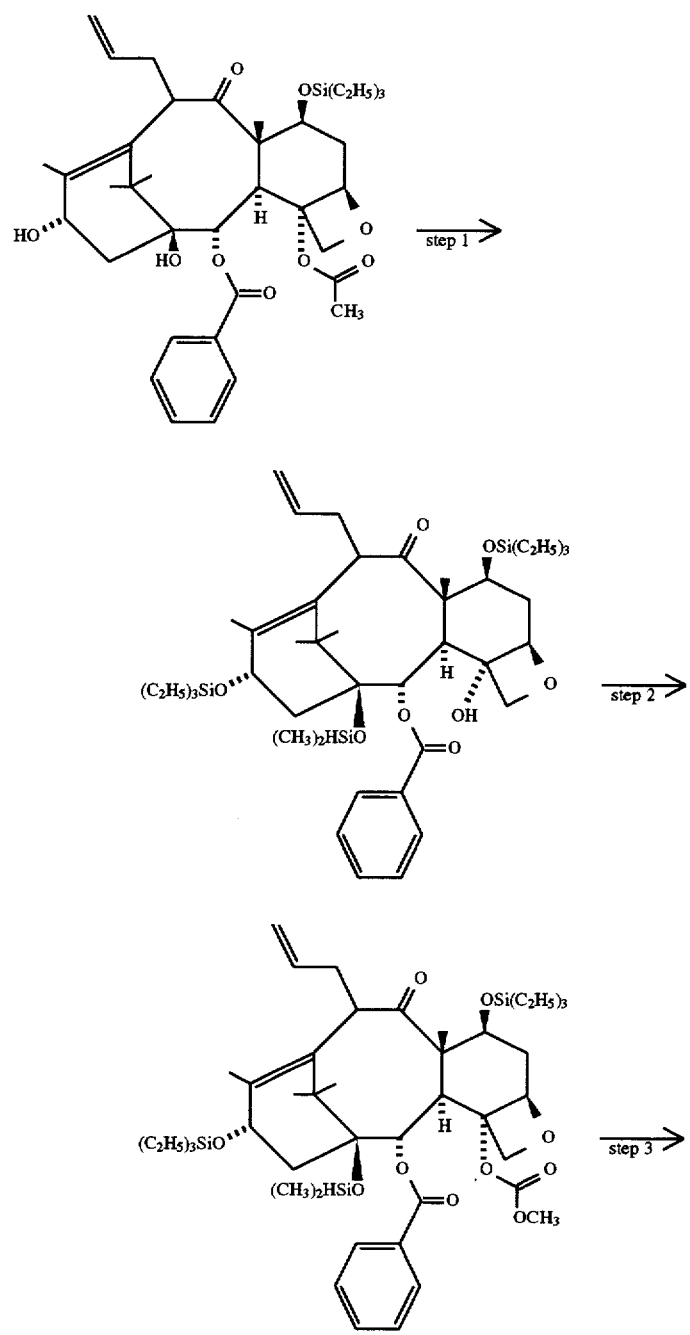

-continued
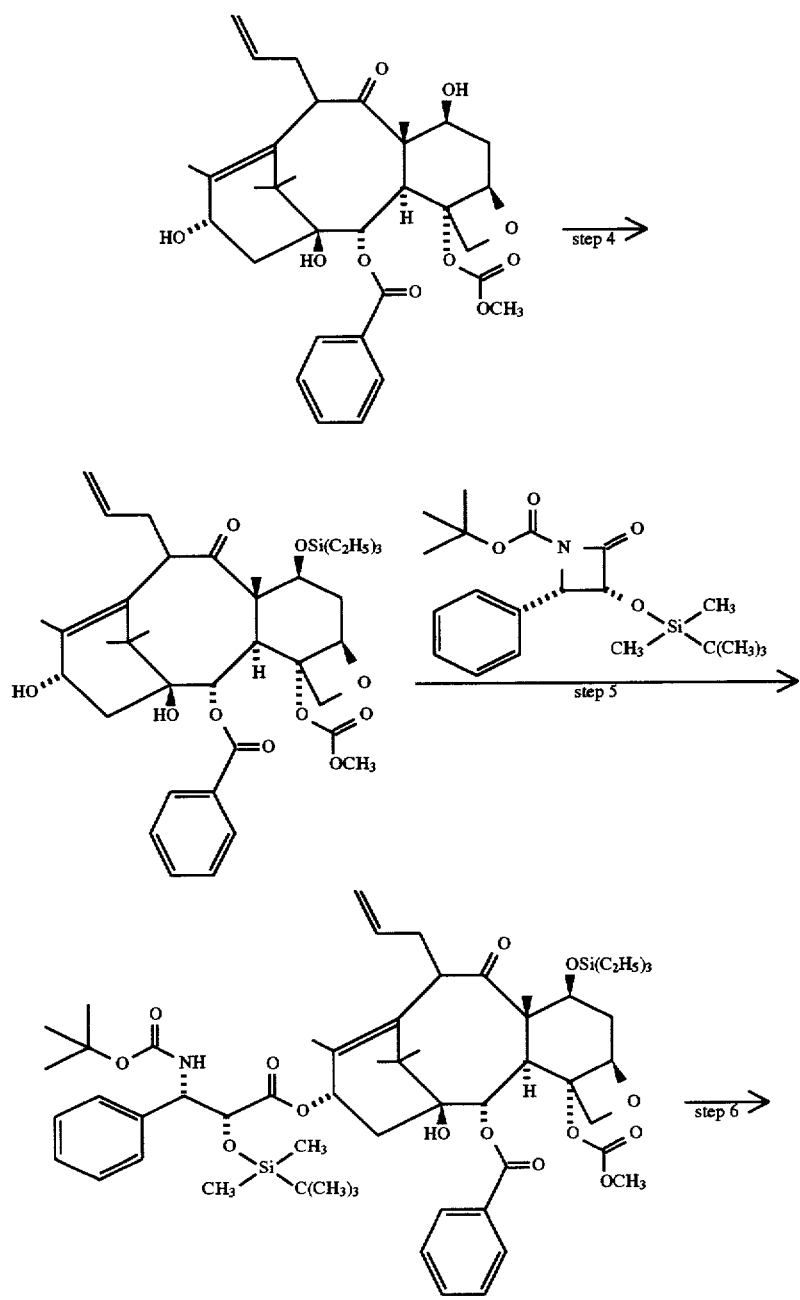

-continued

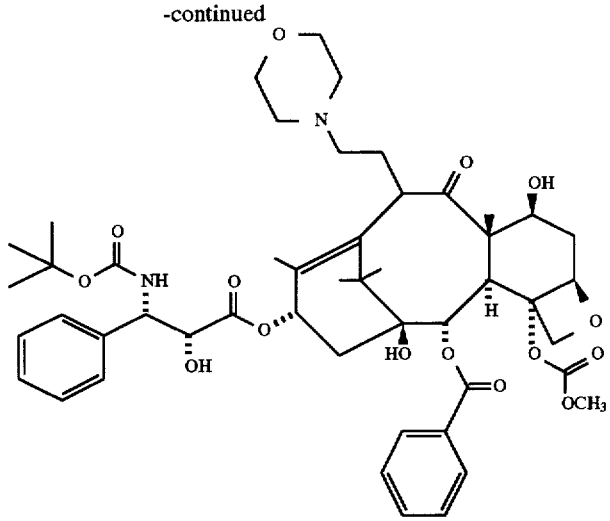

Step 1: 10-Allyl-10-deacetoxy-4-deacetyl-1-O-dimethylsilyl-7,13-bis-O-triethylsilylbaccatin III 450 mg of the compound obtained in Step 1 of Example 26 was dissolved in 9 ml of dried dimethylformamide, and 450 mg of imidazole and 1.10 ml of triethylsilyl chloride were added thereto at 0° C., followed by allowing the mixture to warm to room temperature and then stirring for 1 hour. The mixture was diluted with ethyl acetate, water was added thereto, and the mixture was extracted with ethyl acetate. The extract was dried over anhydrous magnesium sulfate and purified by silica gel column chromatography (a developing solvent; chloroform:acetone=90:10 (v/v)). The product was dissolved in 10.5 ml of dimethylformamide, and 180 mg of imidazole and 0.287 ml of dimethylsilyl chloride were added thereto at 0° C., and the mixture was reacted at that temperature for 30 minutes. The reaction mixture was diluted with ethyl acetate, water was added thereto, and the mixture was extracted with ethyl acetate. The extract was dried over anhydrous magnesium sulfate and purified by silica gel column chromatography (a developing solvent; hexane:ethyl acetate=90:10 (v/v)). The product was dissolved in 9.4 ml of dried tetrahydrofuran, and 0.31 ml of bis(2-methoxyethoxy)aluminum hydride (a 1.0M toluene solution) was added thereto at 0° C., followed by reacting for 5 hours. The reaction mixture was diluted with ethyl acetate, a saturated aqueous potassium tartrate solution was added thereof, and the mixture was extracted with ethyl acetate. The extract was dried over anhydrous magnesium sulfate, the solvent was evaporated under reduced pressure, and the resulting residue was purified by silica gel column chromatography (a developing solvent; hexane:ethyl acetate=90:10 (v/v)) to yield 342 mg of the titled compound.

$^1$H-NMR (CDCl$_3$/TMS) δ(ppm): −0.30(3H, d, J=3 Hz), 0.00(3H, d, J=3 Hz), 0.53(6H, m), 0.78(6H, m), 0.92(12H, m), 1.22(12H, m), 1.51(3H, s), 1.85(3H, s), 1.97(1H, m), 2.35(1H, m), 2.52(1H, m), 2.63(1H, m), 2.73(1H, m), 2.81(1H, m), 3.67(1H, s), 3.70(3H, d, J=6 Hz), 3.88(1H, dd, J=5 Hz, 10 Hz), 4.66(1H, dd, J=6 Hz, 12 Hz), 4.19(1H, d, J=8 Hz), 4.30(1H, d, J=8 Hz), 4.55(1H, m), 4.66(2H, m), 5.03 (2H, m), 5.55(1H, d, J=6 Hz), 5.77(1H, m), 7.42(2H, t, J=7.5 Hz), 7.53(1H, t, J=7.5 Hz), 8.10(2H, d, J=7.5 Hz).

MASS-FAB: 813(M$^+$)

Step 2: 10-Allyl-10-deacetoxy-4-deacetyl-1-O-dimethylsilyl-4-O-methoxycarbonyl-7,13-bis-O-triethylsilylbaccatin III 50 mg of the compound obtained in the above Step 1 was dissolved in 1.5 ml of dried tetrahydrofuran, 92 μl of lithium hexamethyldisilazide (a 1.0M hexane solution) was added thereto at 0° C., followed by reacting for 15 minutes. Then, 7 μl of methoxycarbonyl chloride was added thereto at 0° C., followed by reacting at that temperature for 10 minutes. The reaction mixture was diluted with ethyl acetate, a saturated aqueous solution of potassium tartrate was added thereto, and the mixture was extracted with ethyl acetate. The extract was dried over anhydrous magnesium sulfate, the solvent was evaporated under reduced pressure, and the residue was purified by silica gel thin layer chromatography (a developing solvent; hexane:ethyl acetate=90:10 (v/v)) to yield 42 mg of the titled compound.

$^1$H-NMR (CDCl$_3$/TMS) δ(ppm): −0.30(3H, d, J=3 Hz), 0.07(3H, d, J=3 Hz), 0.53(6H, m), 0.68(6H, m), 0.96(9H, t, J=7.5 Hz), 1.02(9H, t, J=7.5 Hz), 1.12(3H, s), 1.13(3H, s), 1.61(3H, s), 1.89(4H, m), 2.29(2H, d, J=8.5 Hz), 2.46(2H, m), 2.84(1H, m), 3.81(1H, dd, J=4 Hz, 10 Hz), 3.88(3H, s), 3.98(1H, d, J=7 Hz), 4.24(2H, m), 4.48(1H, dd, J=7 Hz, 11 Hz), 4.54(1H, m), 4.98(2H, m), 5.08(1H, dd, J=2 Hz, 14 Hz), 5.70(1H, d, J=7 Hz), 5.77(1H, m), 7.46(2H, t, J=7.5 Hz), 7.57(1H, t, J=7.5 Hz), 8.11(2H, d, J=7.5 Hz).

MASS-FAB: 871(M+)

Step 3: 10-Allyl-10-deacetoxy-4-deacetyl-4-O-methoxycarbonylbaccatin III 42 mg of the compound obtained in the above Step 2 in the same manner as in Step 5 of Example 16, followed by purification to yield 28 mg of the titled compound.

$^1$H-NMR (CDCl$_3$/TMS) δ(ppm): 1.06(3H, s), 1.12(3H, s), 1.61(3H, s), 1.80(1H, m), 1.92(3H, s), 2.21(1H, m), 2.32 (4H, m), 2.91(1H, m), 3.70(1H, m), 3.85(3H, s), 3.92(1H, t, J=7 Hz), 4.13(3H, m), 4.32(2H, m), 4.81(1H, m), 5.00(2H, m), 5.12(1H, dd, J=1.5 Hz, 7 Hz), 5.66(1H, d, J=7 Hz), 5.80(1H, m), 7.49(2H, t, J=7.5 Hz), 7.57(1H, t, J=7.5 Hz), 8.11(2H, d, J=7.5 Hz).

MASS-FAB: 585(M+)

Step 4: 10-Allyl-10-deacetoxy-4-deacetyl-4-O-methoxycarbonyl-7-O-triethylsilylbaccatin III 27 mg of the compound obtained in the above Step 3 was dissolved in 0.5 ml of dried dimethylformamide, and 13 mg of imidazole and 0.03 ml of triethylsilyl chloride were added thereto at 0° C., followed by reacting at that temperature for 30 minutes. The reaction mixture was diluted with ethyl acetate, water was added thereto, and the mixture was extracted with ethyl acetate. The extract was dried over anhydrous magnesium sulfate and purified by silica gel thin layer chromatography (a developing solvent; chloroform:acetone=95:5 (v/v)) to yield 26 mg of the titled compound.

¹H-NMR (CDCl₃/TMS) δ(ppm): 0.58(6H, m), 0.96(9H, t, J=8 Hz), 1.08(3H, s), 1.13(3H, s), 1.61(3H, s), 1.89(1H, m), 1.96(3H, d, J=1 Hz), 2.28(2H, m), 2.52(2H, m), 2.80(1H, m), 3.85(3H, s), 3.92(1H, dd, J=4 Hz, 10 Hz), 4.08(1H, d, J=7 Hz), 4.16(1H, d, J=8 Hz), 4.30(1H, d, J=8 Hz), 4.52(1H, dd, J=7 Hz, 11 Hz), 4.85(1H, m), 5.01(2H, m), 5.10(1H, dd, J=2 Hz, 17 Hz), 5.62(1H, d, J=7 Hz), 5.80(1H, m), 7.49(2H, t, J=7.5 Hz), 7.57(1H, t, J=7.5 Hz), 8.11(2H, d, J=7.5 Hz).

MASS-FAB: 699(M+)

Step 5: 10-Allyl-13-O-[(2R,3S)-3-(tert-butoxycarbonylamino)-2-(tert-butyldimethylsilyloxy)-3-phenylpropionyl]-10-deacetoxy-4-deacetyl-4-O-methoxycarbonyl-7-O-triethylsilylbaccatin III The compound obtained in the above Step 4 was reacted with (3R,4S)-1-(tert-butoxycarbonyl)-4-phenyl-3-(tert-butyldimethylsilyloxy)azetidin-2-one in the same manner as in Step 5 of Example 32, followed by purification to yield the titled compound.

¹H-NMR (CDCl₃/TMS) δ(ppm): −0.34(3H, s), −0.09(3H, s), 0.57(6H, m), 0.75(9H, s), 0.97(9H, m), 1.18(3H, s), 1.23(3H, s), 1.32(9H, s), 1.66(3H, s), 1.80(3H, s), 1.92(1H, m), 2.15(1H, m), 2.49(2H, m), 2.82(1H, m), 3.88(1H, dd, J=4.5 Hz, 10.5 Hz), 4.03(3H, s), 4.12(1H, d, J=7 Hz), 4.28(1H, d, J=8.5 Hz), 4.31(1H, d, J=8.5 Hz), 4.50(1H, dd, J=7 Hz, 11 Hz), 4.57(1H, s), 4.97(1H, d, J=8 Hz), 5.04(1H, d, J=10 Hz), 5.79(1H, m), 6.29(1H, m), 7.30(1H, m), 7.41 (4H, m), 7.44(2H, t, J=7.5 Hz), 7.55(1H, t, J=7.5 Hz), 8.12(2H, d, J=7.5 Hz).

MASS-FAB: 1076(M+)

Step 6: 13-O-[(2R,3S)-3-(tert-butoxycarbonylamino)-2-hydroxy-3-phenylpropionyl]-10-deacetoxy-4-deacetyl-4-O-methoxycarbonyl-10-(2-morpholinoethyl)baccatin III The compound obtained in the above Step 5 was reacted in the same manner as in Step 1 of Example 17, followed by purification. The resulting compound was reacted in the same manner as in Step 1 of Example 18, followed by purification. Then, the resulting compound was reacted in the same manner as in Step 1 of Example 19 except for using morpholine in place of dimethylamine, followed by purification. Finally, the resulting compound was reacted in the same manner as in Step 5 of Example 16, followed by purification to yield the titled compound.

Melting Point: 135°–140° C.

¹H-NMR (CDCl₃/TMS) δ(ppm): 1.11(3H, s), 1.20(3H, s), 1.32(9H, br-s), 1.62(3H, s), 1.81(3H, s), 1.89(1H, m), 2.20 (1H, m), 2.38(3H, m), 2.50– 2.71(7H, m), 3.69(4H, m), 3.82(3H, s), 3.99(2H, m), 4.21(1H, d, J=8.5 Hz), 4.32(1H, d, J=8.5 Hz), 4.42(1H, dd, J=7 Hz, 11 Hz), 4.61(1H, s), 5.01(1H, d, J=8 Hz), 5.30(2H, m), 5.68(1H, d, J=7 Hz), 6.12(1H, m), 7.30(1H, m), 7.40(2H, t, J=7.5 Hz), 7.47(4H, m), 7.59(1H, t, J=7.5 Hz), 8.11(2H, d, J=7.5 Hz).

MASS-FAB: 915(M+).

EXAMPLE 35

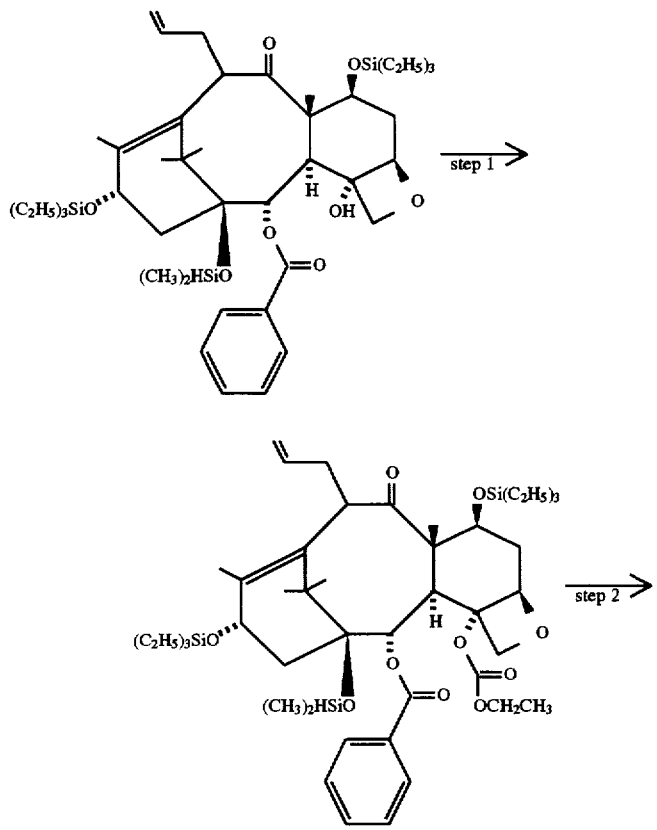

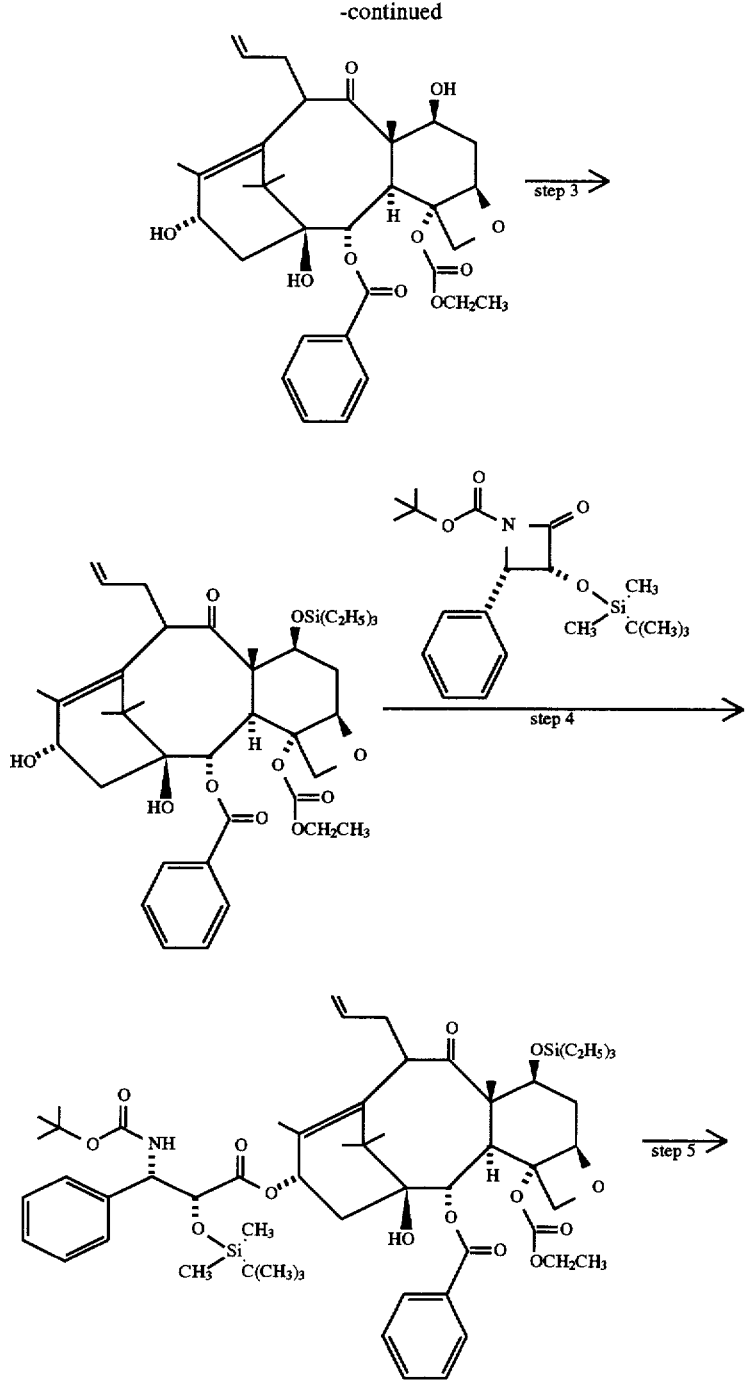

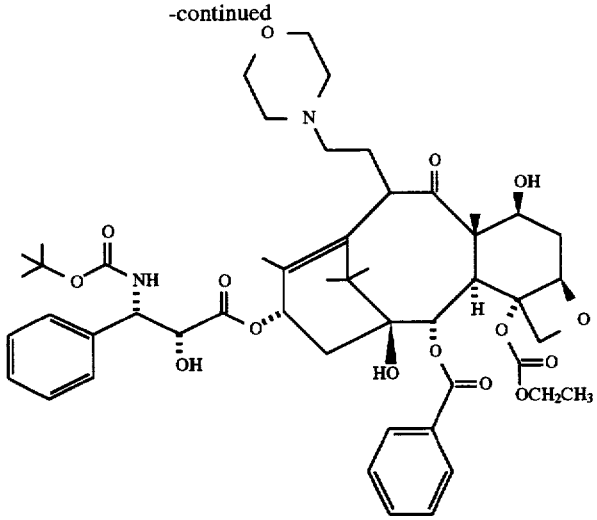

Step 1: 10-Allyl-10-deacetoxy-4-deacetyl-1-O-dimethylsilyl-4-O-ethoxycarbonyl-7,13-bis-O-triethylsilylbaccatin III The compound obtained in Step 1 of Example 34 was reacted in the same manner as in Step 2 of Example 34 except for using ethoxycarbonyl chloride in place of methoxycarbonyl chloride, followed by purification to yield the titled compound.

¹H-NMR (CDCl₃/TMS) δ(ppm): −0.31(3H, d, J=3 Hz), 0.07(3H, d, J=3 Hz), 0.56(6H, m), 0.68(6H, m), 0.98(9H, t, J=8 Hz), 1.02(9H, t, J=8 Hz), 1.12(6H, s), 1.40(3H, t, J=7 Hz), 1.61(3H, s), 1.89(4H, m), 2.29(2H, d, J=8.5 Hz), 2.43(2H, m), 2.82(1H, m), 3.82(1H, dd, J=4 Hz, 10 Hz), 3.99(1H, d, J=7 Hz), 4.24(1H, d, J=8.5 Hz), 4.25(1H, d, J=8.5 Hz), 4.45(2H, m), 4.55(1H, m), 4.98(2H, m), 5.08(1H, d, J=17 Hz), 5.70(1H, d, J=7 Hz), 5.79(1H, m), 7.46(2H, t, J=7.5 Hz), 7.56(1H, t, J=7.5 Hz), 8.10(2H, d, J=7.5 Hz).

MASS-FAB: 885(M+).

Step 2: 10-Allyl-10-deacetoxy-4-deacetyl-4-O-ethoxycarbonylbaccatin III

The compound obtained in the above Step 1 was reacted in the same manner as in Step 5 of Example 16, followed by purification to yield the titled compound.

¹H-NMR (CDCl₃/TMS) δ(ppm): 1.09(3H, s), 1.11(3H, s), 1.39(3H, t, J=7 Hz), 1.60(3H, s), 1.80(1H, m), 1.92(3H, s), 2.25–2.39(3H, m), 2.58(1H, m), 2.92(1H, m), 3.92(1H, t, J=7 Hz), 4.15(3H, m), 4.34(3H, m), 4.81(1H, m), 5.00(1H, m), 5.11(1H, dd, J=1.5 Hz, 17 Hz), 5.66(1H, d, J=7.5 Hz), 5.80(1H, m), 7.48(2H, t, J=7.5 Hz), 7.59(1H, t, J=7.5 Hz), 8.10(2H, d, J=7.5 Hz).

MASS-FAB: 599(M+)

Step 3: 10-Allyl-10-deacetoxy-4-deacetyl-4-O-ethoxycarbonyl-7-O-triethylsilylbaccatin III The compound obtained in the above Step 2 was reacted in the same manner as in Step 4 of Example 34, followed by purification to yield the titled compound.

¹H-NMR (CDCl₃/TMS) δ(ppm): 0.58(6H, m), 0.97(9H, t, J=7.5 Hz), 1.09(3H, s), 1.12(3H, s), 1.39(3H, t, J=7 Hz), 1.61(3H, s), 1.89(1H, m), 1.93(3H, s), 2.28(1H, m), 2.50(2H, m), 2.80(1H, m), 3.91(1H, dd, J=4 Hz, 10 Hz), 4.08(1H, d, J=7 Hz), 4.20(2H, m), 4.32(2H, m), 4.50(1H, dd, J=7 Hz, 11 Hz), 4.81(1H, m), 5.00(2H, m), 5.10(1H, dd, J=1.5 Hz, 17 Hz), 5.61(1H, d, J=7 Hz), 5.79(1H, m), 7.46(2H, t, J=7.5 Hz), 7.58(1H, t, J=7.5 Hz), 8.10(2H, d, J=7.5 Hz).

MASS-FAB: 713(M+).

Step 4: 10-Allyl-13-O-[(2R,3S)-3-(tert-butoxycarbonylamino)-2-(tert-butyldimethylsilyloxy)-3-phenylpropionyl]-10-deacetoxy-4-deacetyl-4-O-ethoxycarbonyl-7-O-triethylsilylbaccatin III The compound obtained in the above Step 3 was reacted with (3R,4S)-1-(tert-butoxycarbonyl)-4-phenyl-3-(tert-butyldimethylsilyloxy)azetidin-2-one in the same manner as in Step 5 of Example 32, followed by purification to yield the titled compound.

¹H-NMR (CDCl₃/TMS) δ(ppm): −0.33(3H, s), −0.09(3H, s), 0.58(6H, m), 0.75(9H, s), 0.97(9H, m), 1.18(3H, s), 1.22(3H, s), 1.28(3H, m), 1.32(9H, s), 1.65(3H, s), 1.80(3H, s), 1.94(1H, m), 2.13(1H, m), 2.48(2H, m), 2.82(1H, m), 3.88(1H, dd, J=4 Hz, 10 Hz), 4.12(1H, d, J=7 Hz), 4.26(1H, d, J=8 Hz), 4.30(1H, d, J=8 Hz), 4.50(4H, m), 4.95(1H, d, J=8 Hz), 5.03(1H, d, J=10 Hz), 5.11(1H, d, J=17 Hz), 5.39(1H, m), 5.44(1H, m), 5.69(1H, d, J=7 Hz), 5.78(1H, m), 6.22(1H, m), 7.29(1H, m), 7.39(4H, m), 7.45(2H, t, J=7.5 Hz), 7.56(1H, t, J=7.5 Hz), 8.13(2H, d, J=7.5 Hz).

MASS-FAB: 1090(M+).

Step 5: 13-O-[(2R,3S)-3-(tert-Butoxycarbonylamino)-2-hydroxy-3-phenylpropionyl]-10-deacetoxy-4-deacetyl4-O-ethoxycarbonyl-10-(2-morpholinoethyl)baccatin III The compound obtained in the above Step 4 was reacted in the same manner as in Step 1 of Example 17, followed by purification. The resulting compound was reacted in the same manner as in Step 1 of Example 18, followed by purification. Then, the resulting compound was reacted in the same manner as in Step 1 of Example 19 except for using morpholine in place of dimethylamine, followed by purification. Finally, the resulting compound was reacted in the same manner as in Step 5 of Example 16, followed by purification to yield the titled compound.

Melting Point: 125°–130° C.

¹H-NMR (CDCl₃/TMS) δ(ppm): 1.11(3H, s), 1.19(3H, s), 1.28(3H, m), 1.33(9H, s), 1.62(3H, s), 1.80(3H, s), 1.90(1H, m), 2.20–2.75(11H, m), 3.68(4H, m), 4.00(2H, m), 4.20(1H, d, J=8.5 Hz), 4.33(1H, d, J=8.5 Hz), 4.40(3H, m), 4.60(1H, s), 5.00(1H, d, J=8 Hz), 5.29(1H, m), 5.40(1H, m), 5.68(1H, d, J=7 Hz), 6.07(1H, m), 7.29(1H, m), 7.38(2H, m), 7.43 (4H, m), 7.59(1H, t, J=7.5 Hz), 8.11(2H, d, J=7.5 Hz).

EXAMPLE 36
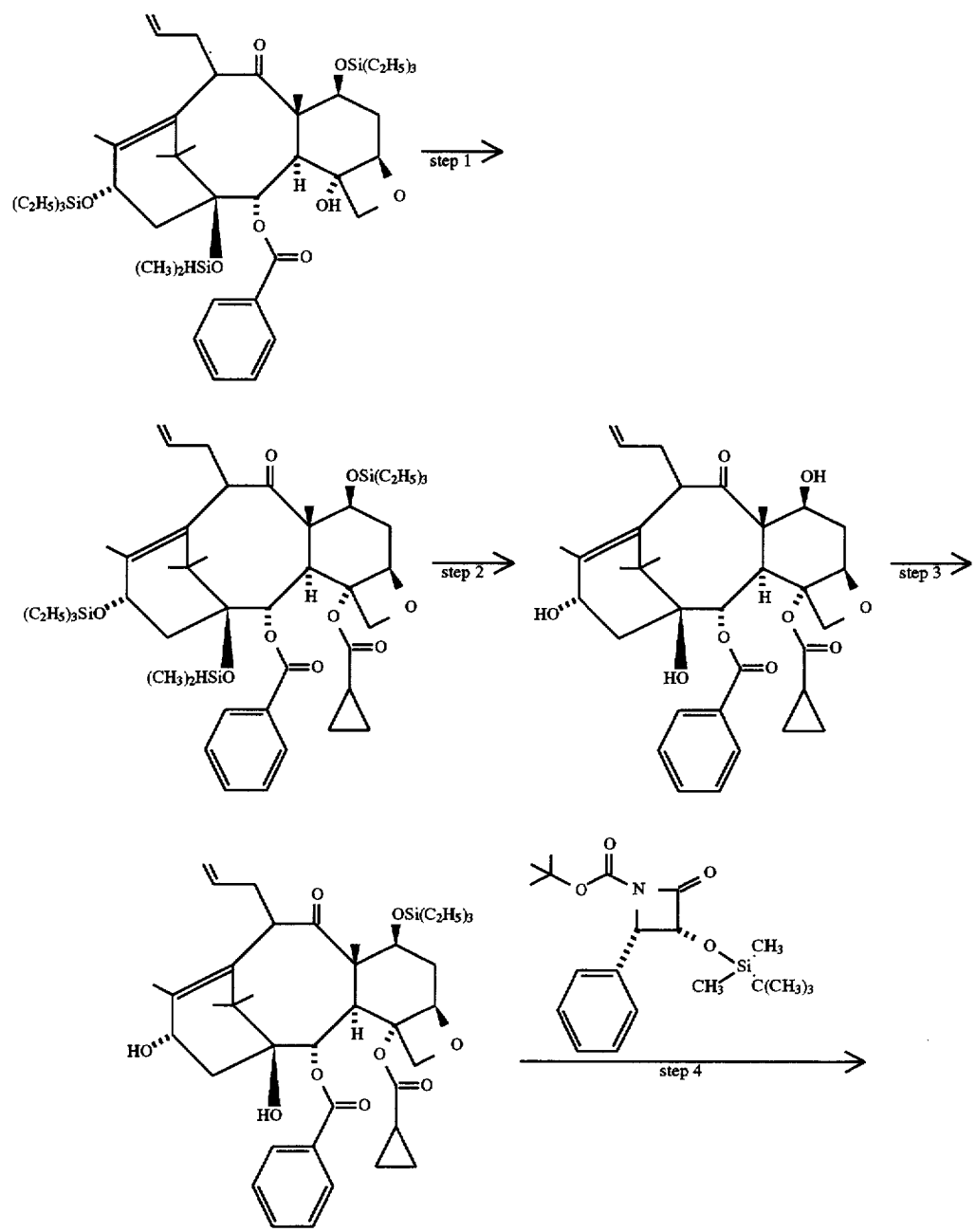

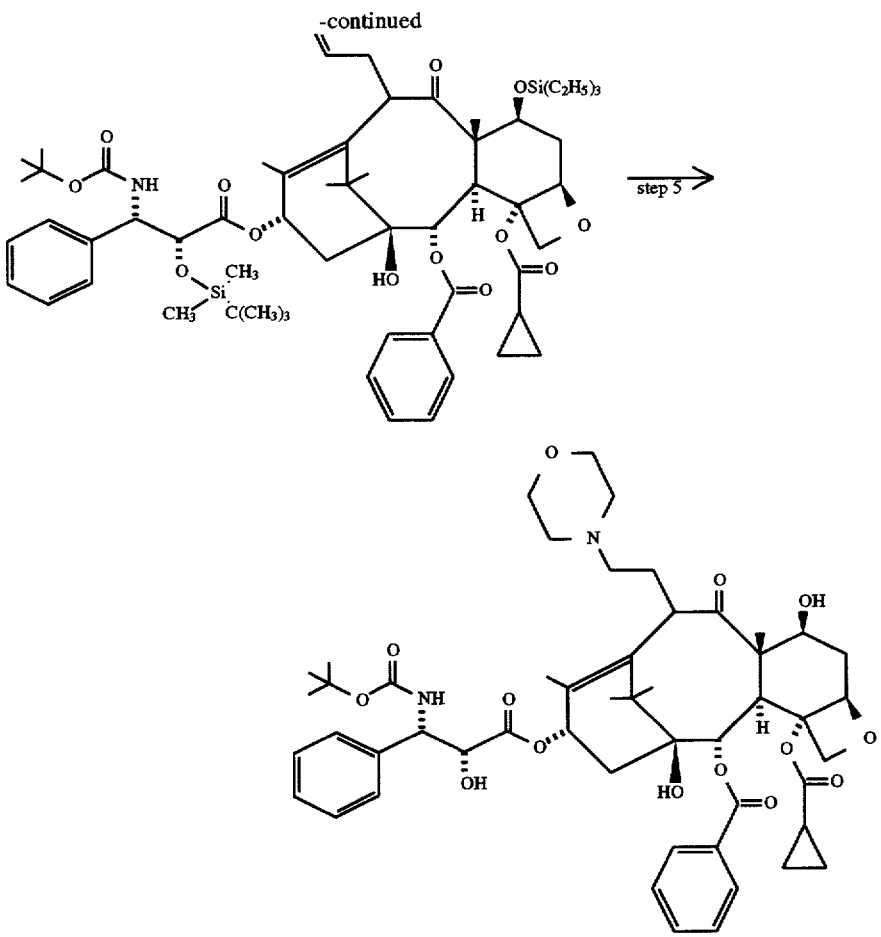

Step 1: 10-Allyl-4-O-cyclopropylcarbonyl-10-deacetoxy-4-deacetyl-1-O-dimethylsilyl-7,13-bis-O-triethylsilylbaccatin III The compound obtained in Step 1 of Example 34 was reacted in the same manner as in Step 2 of Example 34 except for using cyclopropylcarbonyl chloride in place of methoxycarbonyl chloride, followed by purification to yield the titled compound.

$^1$H-NMR (CDCl$_3$/TMS) δ(ppm): −0.29(3H, d, J=3 Hz), 0.08(3H, d, J=3 Hz), 0.55(6H, m), 0.68(6H, m), 0.94(9H, t, J=7 Hz), 1.02(11H, m), 1.13(3H, s), 1.14(3H, s), 1.26(2H, br), 1.61(3H, s), 1.72(1H, m), 1.88(3H, s), 2.30(2H, m), 2.43(2H, m), 2.82(1H, m), 3.82(1H, dd, J=4 Hz, 10 Hz), 3.96(1H, d, J=7 Hz), 4.20(1H, d, J=8.5 Hz), 4.21(1H, d, J=8.5 Hz), 4.48(1H, dd, J=7 Hz, 11 Hz), 4.57(1H, m), 4.83(1H, dd, J=2 Hz, 8 Hz), 4.99(2H, m), 5.08(1H, d, J=17 Hz), 5.69(1H, d, J=7 Hz), 5.78(1H, m), 7.46(2H, t, J=7.5 Hz), 7.58(1H, t, J=7.5 Hz), 8.08(2H, d, J=7.5 Hz).

MASS-FAB: 881 (M+)

Step 2: 10-Allyl-4-O-cyclopropylcarbonyl-10-deacetoxy-4-deacetylbaccatin III

The compound obtained in the above Step 1 was reacted in the same manner as in Step 5 of Example 16, followed by purification to yield the titled compound.

$^1$H-NMR (CDCl$_3$/TMS) δ(ppm): 1.08(3H, s), 1.11(3H, s), 1.24(4H, m), 1.63(3H, s), 1.79(2H, m), 1.91(3H, d, J=1 Hz), 2.27(2H, d, J=8 Hz), 2.34(1H, m), 2.53(1H, m), 2.92(1H, m), 3.90(1H, t, J=7 Hz), 4.10(1H, d, J=7 Hz), 4.20(1H, d, J=8 Hz), 4.31(1H, d, J=8 Hz), 4.34(1H, m), 4.80(1H, m), 4.88(1H, dd, J=8 Hz), 5.00(1H, dd, J=1 Hz, 10 Hz), 5.10(1H, dd, J=1.5 Hz, 17 Hz), 5.64(1H, d, J=7 Hz), 5.79(1H, m), 7.48(2H, t, J=7.5 Hz), 7.60(1H, t, J=7.5 Hz), 8.10(2H, d, J=7.5 Hz).

MASS-FAB: 595(M+)

Step 3: 10-Allyl-4-O-cyclopropylcarbonyl-10-deacetoxy-4-deacetyl-7-O-triethylsilylbaccatin III The compound obtained in the above Step 2 was reacted in the same manner as in Step 4 of Example 34, followed by purification to yield the titled compound.

$^1$H-NMR (CDCl$_3$/TMS) δ(ppm): 0.57(6H, m), 0.95(9H, t, J=8 Hz), 1.05(2H, m), 1.08(3H, s), 1.13(3H, s), 1.24(2H, m), 1.62(3H, s), 1.79(1H, m), 1.88(1H, m), 1.92(3H, d, J=1 Hz), 2.26(1H, m), 2.42–2.58(2H, m), 2.79(1H, m), 3.89(1H, dd, J=4 Hz, 10 Hz), 4.05(1H, d, J=7 Hz), 4.19(1H, d, J=8 Hz), 4.29(1H, d, J=8 Hz), 4.50(1H, dd, J=7 Hz, 11 Hz), 4.82(1H, m), 4.86(1H, m), 5.02(1H, dd, J=1.5 Hz, 10 Hz), 5.10(1H, dd, J=1.5 Hz, 17 Hz), 5.61(1H, d, J=7 Hz), 5.79(1H, m), 7.47(2H, t, J=7.5 Hz), 7.60(1H, t, J=7.5 Hz), 8.11(2H, d, J=7.5 Hz).

MASS-FAB: 709(M+)

Step 4: 10-Allyl-13-O-[(2R,3S)-3-(tert-butoxycarbonylamino)-2-(tert-butyldimethylsilyloxy)-3-phenylpropionyl]-4-O-cyclopropylcarbonyl-10-deacetoxy-4-deacetyl-7-O-triethylsilylbaccatin III The compound obtained in the above Step 3 was reacted with (3R,4S)-1-(tert-butoxycarbonyl)-4-phenyl-3-(tert-butyldimethylsilyloxy)azetidin-2-one in the same manner as in Step 5 of Example 32, followed by purification to yield the titled compound.

$^1$H-NMR (CDCl$_3$/TMS) δ(ppm): −0.30(3H, s), −0.05(3H, s), 0.57(6H, m), 0.74(9H, s), 0.96(9H, m), 1.17(3H, s), 1.24(4H, m), 1.27(3H, s), 1.33(9H, s), 1.62(3H, s), 1.78(3H, s), 1.90(2H, m), 2.14(1H, m), 2.46(3H, m), 2.82(1H, m), 3.84(1H, dd, J=4 Hz, 10 Hz), 4.00(1H, d, J=7 Hz), 4.21(1H, d, J=8 Hz), 4.23(1H, d, J=8 Hz), 4.51(1H, dd, J=7 Hz, 11 Hz), 4.60(1H, s), 4.81(1H, d, J=8 Hz), 5.04(1H, d, J=10 Hz), 5.10(1H, d, J=17 Hz), 5.32(1H, m), 5.42(1H, m), 5.68(1H, d, J=7 Hz), 5.79(1H, m), 6.23(1H, m), 7.25(3H, m), 7.34 (2H, m), 7.48(2H, t, J=7.5 Hz), 7.59(1H, t, J=7.5 Hz), 8.09(2H, d, J=7.5 Hz).

MASS-FAB: 1086(M+)

Step 5: 13-O-[(2R,3S)-3-(tert-butoxycarbonylamino)-2-hydroxy-3-phenylpropionyl]-4-O-cyclopropylcarbonyl-10-deacetoxy-10-(2-morpholinoethyl)baccatin III The compound obtained in the above Step 4 was reacted in the same manner as in Step 1 of Example 17, followed by purification. The resulting compound was reacted in the same manner as in Step 1 of Example 18, followed by purification. Then, the resulting compound was reacted in the same manner as in Step 1 of Example 19 except for using morpholine in place of dimethylamine, followed by purification. Finally, the resulting compound was reacted in the same manner as in Step 5 of Example 16, followed by purification to yield the titled compound.

Melting Point: 135°–140° C.

$^1$H-NMR (CDCl$_3$/TMS) δ(ppm): 0.90(2H, m), 1.10(3H, s), 1.20(5H, m), 1.32(9H, s), 1.60(3H, s), 1.78(3H, s), 1.85(1H, m), 2.25–2.75(12H, m), 3.66(4H, m), 3.95(1H, d, J=7 Hz), 4.01(1H, d, J=6 Hz), 4.19(1H, d, J=8.5 Hz), 4.22(1H, d, J=8.5 Hz), 4.42(1H, dd, J=7 Hz, 11 Hz), 4.69 (1H, s), 4.88(1H, d, J=8 Hz), 5.29(1H, m), 5.32(1H, m), 5.62(1H, d, J=7 Hz), 6.09(1H, m), 7.30(1H, m), 7.38(4H, m), 7.49(2H, t, J=7.5 Hz), 7.60(1H, t, J=7.5 Hz), 8.08(2H, d, J=7.5 Hz).

EXAMPLE 37

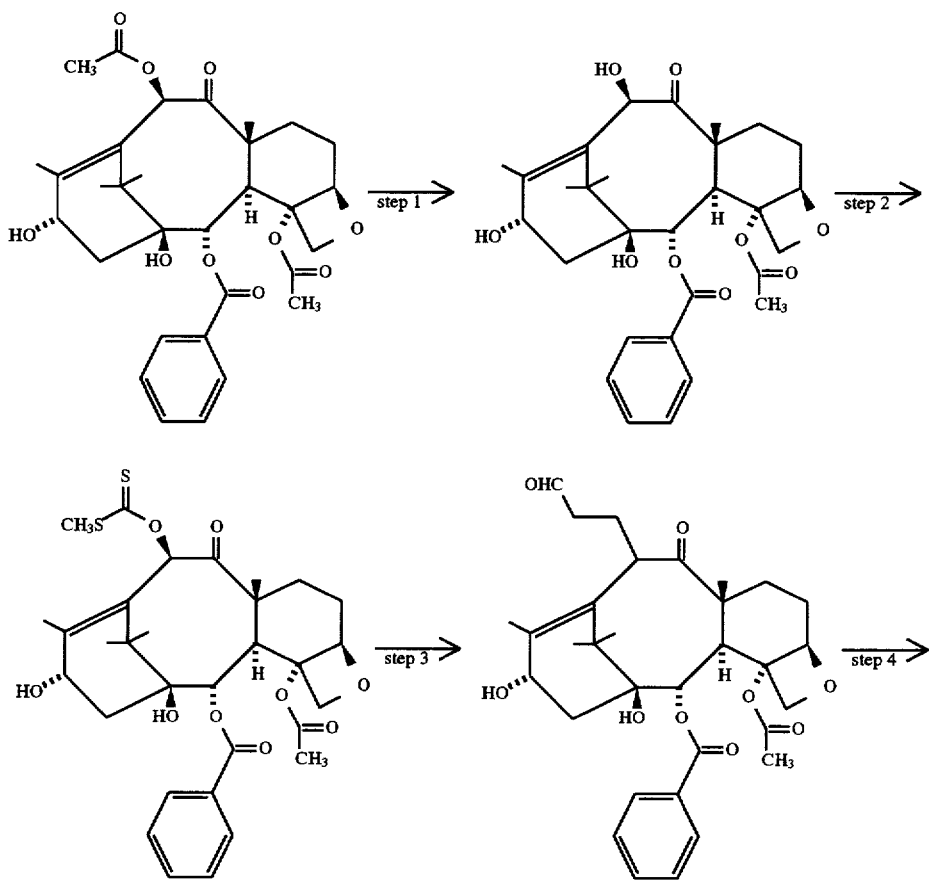

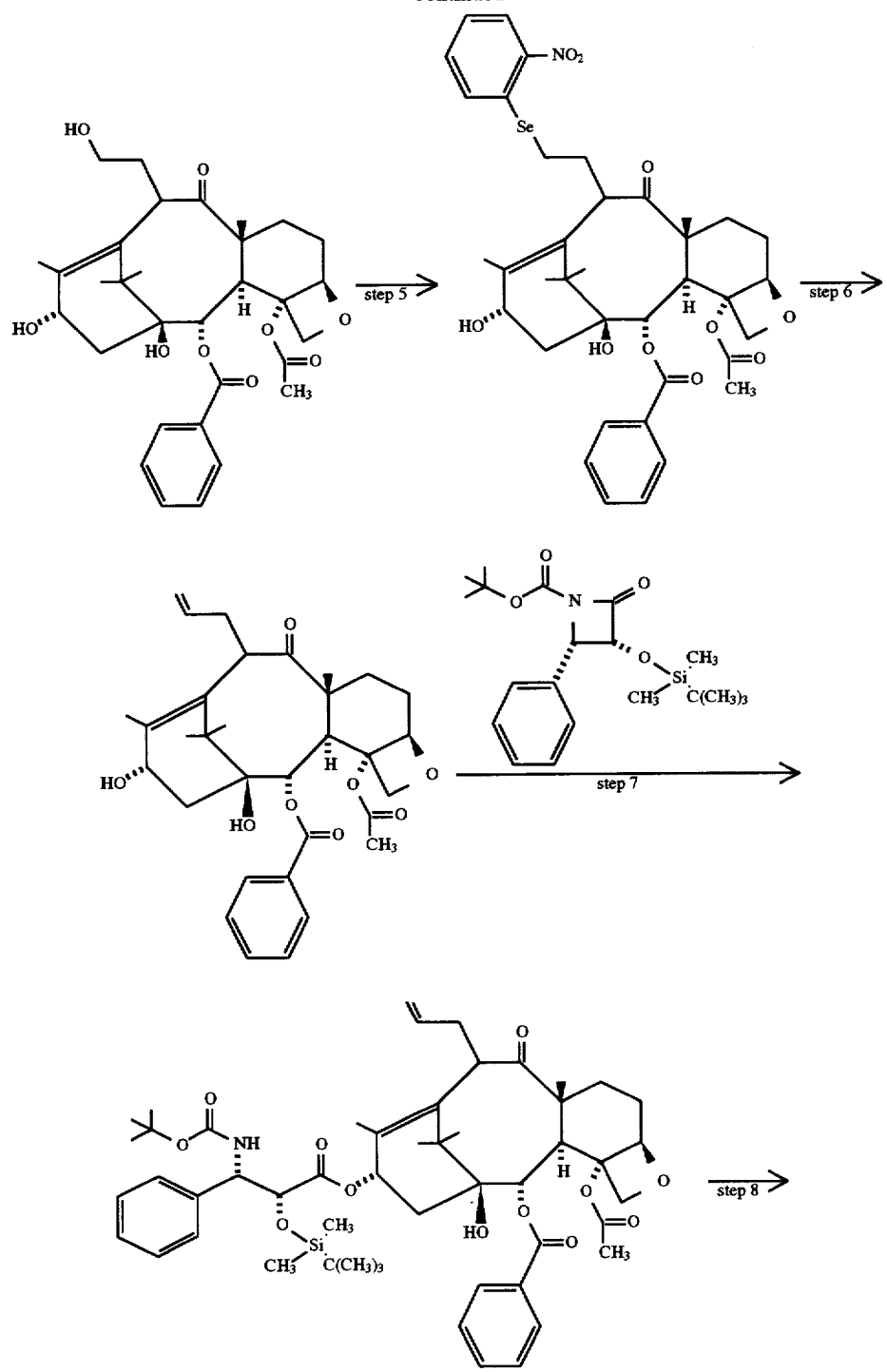

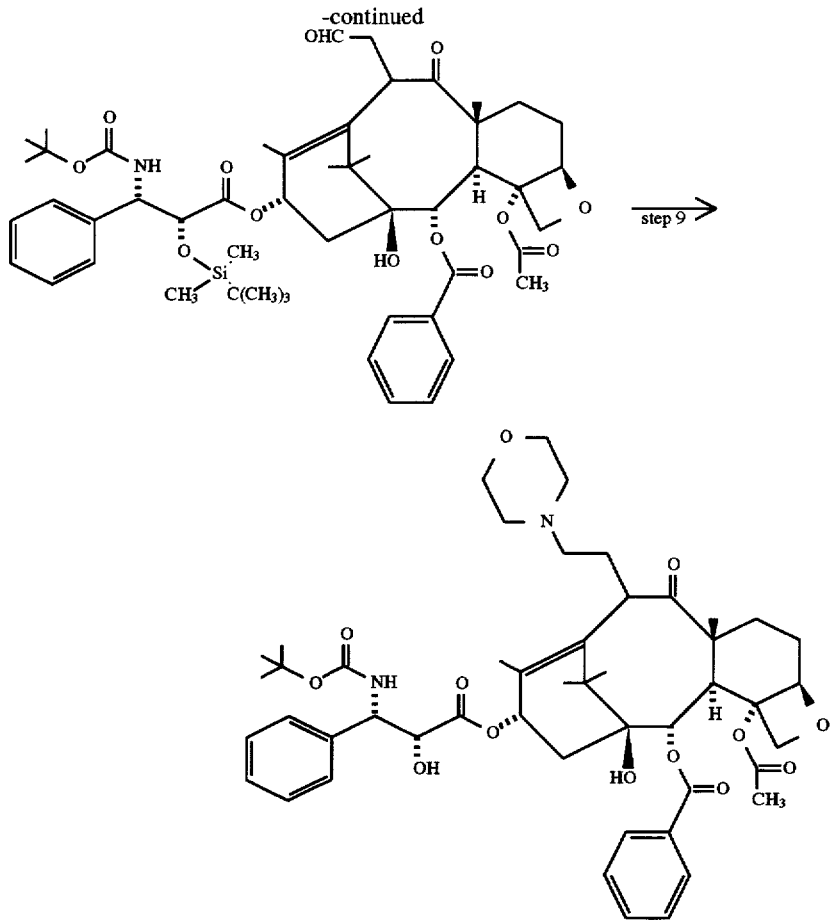

Step 1: 10-Deacetyl-7-deoxybaccatin III 6.85 g of 7-deoxybaccatin III was dissolved in 250 ml of 95% ethanol, and 25 ml of hydrazine monohydrate was added thereto, followed by stirring at room temperature for 7 hours. Ethyl acetate was added to the reaction solution, the resulting mixture was washed successively with water and a saturated aqueous sodium chloride solution, and the organic layer was dried over anhydrous sodium sulfate. The solvent was evaporated under reduced pressure, and the resulting residue was purified by silica gel thin layer chromatography (a developing solvent; hexane:ethyl acetate=3:2 (v/v)) to yield 3.34 g of the titled compound as colorless crystals.

$^1$H-NMR (CDCl$_3$/TMS) δ(ppm): 1.06(3H, s), 1.09(3H, s), 1.45–1.7(1H, m), 1.80(3H, s), 1.9–2.2(2H, m), 2.06(3H, d, J=1 Hz), 2.2–2.4(2H, m), 2.29(3H, s), 3.92(1H, d, J=7 Hz), 4.18(1H, d, J=1 Hz), 4.22(1H, d, J=8 Hz), 4.33(1H, d, J=8 Hz), 4.87(1H, m), 4.97(1H, dd, J=2 Hz, 9 Hz), 5.24(1H, d, J=1 Hz), 5.62(1H, d, J=7 Hz), 7.49(1H, d, J=7 Hz), 7.59(2H, t, J=7 Hz), 8.12(2H, d, J=7 Hz).

Step 2: 10-Deacetyl-7-deoxy-10-O-[(methylthio)thiocarbonyl]-baccatin III 2.20 g of the compound obtained in the above Step 1 was dissolved in 30 ml of dried tetrahydrofuran, and then a hexane solution of n-butyl lithium (a 1.6M concentration) was added thereto at −48° C., followed by stirring at that temperature for 10 minutes. 0.36 ml of carbon disulfide and 0.36 ml of methyl iodide were added successively to the reaction solution, and thereafter the resulting mixture was stirred for 2 hours while gradually elevating the temperature up to −10° C. A 10% aqueous of ammonium chloride solution was added thereto, and the mixture was extracted twice with ethyl acetate. The resulting organic layer was washed with a saturated aqueous sodium chloride solution, dried over anhydrous sodium sulfate, and the solvent was evaporated under reduced pressure. The resulting residue was purified by silica gel thin layer chromatography (a developing solvent; hexane:ethyl acetate=3:2 (v/v)) to yield 2.12 g of the titled compound as colorless crystals.

$^1$H-NMR (CDCl$_3$/TMS) δ(ppm): 1.11(3H, s), 1.16(3H, s), 1.2–1.4(1H, m), 1.5–1.7(1H, m), 1.73(3H, s), 1.8–2.5(4H, m), 2.09(3H, s), 2.29(3H, s), 2.64(3H, s), 3.83(1H, d, J=7 Hz), 4.19(1H, d, J=8 Hz), 4.32(1H, d, J=8 Hz), 4.87(1H, m), 4.97(1H, d, J=9 Hz), 5.64(1H, d, J=7 Hz), 7.46(1H, s), 7.48(2H, t, J=7 Hz), 7.61(1H, d, J=7 Hz), 8.12(2H, d, J=7 Hz).

Step 3: 10-Deacetoxy-7-deoxy-10-(3-oxopropyl)baccatin III

The compound obtained in the above Step 2 was reacted in the same manner as in Step 1 of Example 1 except for using acrolein in place of acrylonitrile to yield the titled compound.

$^1$H-NMR (CDCl$_3$/TMS) δ(ppm): 1.06(3H, s), 1.07(3H, s), 1.2–1.5(1H, m), 1.6–2.7(9H, m), 1.69(3H, s), 1.92(3H, d, J=1 Hz), 2.29(3H, s), 3.84(1H, t, J=6 Hz), 3.98(1H, d, J=7 Hz), 4.23(1H, d, J=8 Hz), 4.31(1H, d, J=8 Hz), 4.84(1H, m), 4.96(1H, dd, J=2 Hz, 9 Hz), 5.60(1H, d, J=7 Hz), 7.48(2H, t, J=7 Hz), 7.61(1H, t, J=7 Hz), 8.12(2H, d, J=7 Hz), 9.80(1H, s).

Step 4: 10-Deacetoxy-7-deoxy-10-(3-hydroxypropyl)baccatin III

The compound obtained in the above Step 3 was reacted in the same manner as in Step 2 of Example 6 to yield the titled compound as a white powder.

¹H-NMR (CDCl₃/TMS) δ(ppm): 1.06(6H, s), 1.3–1.7(4H, m), 1.74(3H, s), 1.8–2.0(1H, m), 1.92(3H, s), 2.1–2.4(5H, m), 2.29(3H, s), 3.5–3.75(2H, m), 3.81(1H, t, J=6 Hz), 4.03(1H, d, J=7 Hz), 4.23(1H, d, J=8 Hz), 4.31(1H, d, J=8 Hz), 4.82(1H, d, J=8 Hz), 4.97(1H, dd, J=3 Hz, 10 Hz), 5.60(1H, d, J=7 Hz), 7.48(2H, t, J=7 Hz), 7.60(1H, t, J=7 Hz), 8.12(2H, d, J=7 Hz).

Step 5: 10-Deacetoxy-7-deoxy-10-[3-(2-nitrophenylseleno)propyl]baccatin III 399 mg of the compound obtained in the above Step 4 and 195 mg of o-nitrophenyl selenocyanate were dissolved in 8 ml of dried tetrahydrofuran, and 0.27 ml of tri-n-butyl phosphine was added thereto while stirring at room temperature, followed by stirring for 2 hours. The solvent was evaporated under reduced pressure, the resulting residue was purified by silica gel thin layer chromatography (a developing solvent; hexane:ethyl acetate=2:3 (v/v)) to yield 394 mg of the titled compound as a yellow powder.

¹H-NMR (CDCl₃/TMS) δ(ppm): 1.04(3H, s), 1.06(3H, s), 1.5–1.8(4H, m), 1.70(3H, s), 1.8–2.1(1H, m), 1.90(3H, d, J=1 Hz), 2.1–2.5(5H, m), 2.29(3H, s), 2.91(1H, m), 3.03(1H, m), 3.82(1H, t, J=6 Hz), 4.00(1H, d, J=7 Hz), 4.23(1H, d, J=8 Hz), 4.31(1H, d, J=8 Hz), 4.83(1H, t, J=8 Hz), 4.97(1H, dd, J=3 Hz, 10 Hz), 5.61(1H, d, J=7 Hz), 7.32(1H, m), 7.48(2H, t, J=7 Hz), 7.53(2H, m), 7.61(1H, t, J=7 Hz), 8.12(2H, d, J=7 Hz), 8.29(1H, d, J=8 Hz).

Step 6: 10-Allyl-10-deacetoxy-7-deoxybaccatin III 394 mg of the compound obtained in the above Step 5 was dissolved in 20 ml of tetrahydrofuran, and 95 mg of m-chloroperbenzoic acid was added thereto while stirring at 0° C., followed by stirring at room temperature for 2 hours. After adding 100 ml of ethyl acetate to the reaction solution, the mixture was washed successively with a saturated aqueous sodium hydrogencarbonate solution and a saturated aqueous sodium chloride solution, and the organic layer was dried over anhydrous sodium sulfate. The solvent was evaporated under reduced pressure, and the resulting residue was purified by silica gel thin layer chromatography (a developing solvent; hexane:ethyl acetate=13:7 (v/v)), followed by recrystallization from ethyl acetate-hexane to yield 236 mg of the titled compound as colorless crystals.

¹H-NMR (CDCl₃/TMS) δ(ppm): 1.07(6H, s), 1.45(1H, dd, J=7 Hz, 11 Hz), 1.70(3H, s), 1.85–2.2(1H, m), 1.90(3H, s), 2.1–2.4(5H, m), 2.29(3H, s), 2.95(1H, dt, J=15 Hz, 6 Hz), 3.92(1H, t, J=7 Hz), 4.02(1H, d, J=7 Hz), 4.25(1H, d, J=8 Hz), 4.32(1H, d, J=8 Hz), 4.85(1H, t, J=8 Hz), 4.98(1H, dd, J=3 Hz, 9 Hz), 5.01(1H, d, J=11 Hz), 5.09(1H, d, J=17 Hz), 5.62(1H, d, J=7 Hz), 5.82(1H, m), 7.48(2H, t, J=7 Hz), 7.60(1H, t, J=7 Hz), 8.13(2H, d, J=7 Hz).

Step 7: 10-Allyl-13-O-[(2R,3S)-3-(tert-butoxycarbonylamino)-2-(tert-butyldimethylsilyloxy)-3-phenylpropionyl]-10-deacetoxy-7-deoxybaccatin III The compound obtained in the above Step 6 was reacted with (3R,4S)-1-(tert-butoxycarbonyl)-4-phenyl-3-(tert-butyldimethylsilyloxy)azetidin-2-one in the same manner as in Step 4 of Example 16 to yield the titled compound.

¹H-NMR (CDCl₃/TMS) δ(ppm): −0.34(3H, s), −0.11(3H, s), 0.74(9H, s), 1.11(3H, s), 1.23(3H, s), 1.28(9H, s), 1.4–1.5(1H, m), 1.72(3H, s), 1.74(3H, s), 1.8–2.35(5H, m), 2.43(1H, dd, J=10 Hz, 15 Hz), 2.54(3H, s), 2.96(1H, dt, J=15 Hz, 7 Hz), 3.88(1H, t, J=7 Hz), 3.93(1H, d, J=7 Hz), 4.27(1H, d, J=8 Hz), 4.33(1H, d, J=8 Hz), 4.50(1H, br.s), 4.97(1H, dd, J=3 Hz, 9 Hz), 5.03(1H, d, J=11 Hz), 5.10(1H, d, J=17 Hz), 5.33(1H, br-d, J=8 Hz), 5.45(1H, br-d, J=8 Hz), 5.67(1H, d, J=7 Hz), 5.82(1H, m), 6.27(1H, t, J=8 Hz), 7.2–7.35(3H, m), 7.37(2H, t, J=7 Hz), 7.49(2H, t, J=7 Hz), 7.58(1H, t, J=7 Hz), 8.14(2H, d, J=7 Hz).

Step 8: 13-O-[(2R,3S -3-(tert-butoxycarbonylamino)-2-(tert-butyldimethylsilyloxy)-3-phenylpropionyl]-10-deacetoxy-7-deoxy-10-formylmethylbaccatin III The compound obtained in the above Step 7 was reacted in the same manner as in Step 1 of Example 17, followed by purification. The resulting compound was then reacted in the same manner as in Step 1 of Example 18, followed by purification to yield the titled compound.

¹H-NMR (CDCl₃/TMS) δ(ppm): −0.33(3H, s), −0.12(3H, s), 0.74(9H, s), 1.07(3H, s), 1.22(3H, s), 1.28(9H, s), 1.48(1H, dd, J=6 Hz, 12 Hz), 1.71(3H, s), 1.79(3H, s), 1.95(1H, m), 2.11(1H, dd, J=8 Hz, 15 Hz), 2.23(1H, dd, J=3 Hz, 17 Hz), 2.2–2.35(2H, m), 2.43(1H, dd, J=10 Hz, 15 Hz), 2.55(3H, s), 3.49(1H, dd, J=10 Hz, 17 Hz), 3.92(1H, d, J=7 Hz), 4.26(1H, d, J=8 Hz), 4.33(1H, d, J=8 Hz), 4.51(1H, br-s), 4.64(1H, dd, J=3 Hz, 10 Hz), 4.98(1H, dd, J=3 Hz, 9 Hz), 5.33(1H, br-d, J=8 Hz), 5.43(1H, br-d, J=8 Hz), 5.65(1H, d, J=7 Hz), 6.24(1H, t, J=9 Hz), 7.2–7.35(3H, m), 7.38(2H, t, J=7 Hz), 7.49(2H, t, J=7 Hz), 7.58(1H, t, J=7 Hz), 8.14(2H, d, J=7 Hz), 9.87(1H, s).

Step 9: 13-O-[(2R,3S)-3-(tert-Butoxycarbonylamino)-2-hydroxy-3-phenylpropionyl]-10-deacetoxy-7-deoxy-10-(2-morpholinoethyl)baccatin III The compound obtained in the above Step 8 was reacted in the same manner as in Step 1 of Example 19 except for using morpholine in place of dimethylamine, followed by purification. The resulting compound was reacted in the same manner as in Step 5 of Example 16, followed by purification to yield the titled compound.

¹H-NMR (CDCl₃/TMS) δ(ppm): 1.09(3H, s), 1.20(3H, s), 1.31(9H, s), 1.3–1.6(2H, m), 1.71(3H, s), 1.80(3H, s), 1.85–2.05(1H, m), 2.1–2.6(11H, m), 2.40(3H, s), 3.68(4H, m), 3.92(1H, d, J=7 Hz), 4.08(1H, t, J=5 Hz), 4.24(1H, d, J=8 Hz), 4.32(1H, d, J=8 Hz), 4.60(1H, br-s), 4.95(1H, dd, J=3 Hz, 9 Hz), 5.28(1H, br-d, J=9 Hz), 5.37(1H, d, J=9 Hz), 5.65(1H, d, J=7 Hz), 6.20(1H, t, J=9 Hz), 7.31(1H, t, J=7 Hz), 7.37(2H, t, J=7 Hz), 7.40(2H, t, J=7 Hz), 7.51(2H, t, J=7 Hz), 7.61(1H, t, J=77 Hz), 8.14(2H, d, J=7 Hz).

EXAMPLE 38

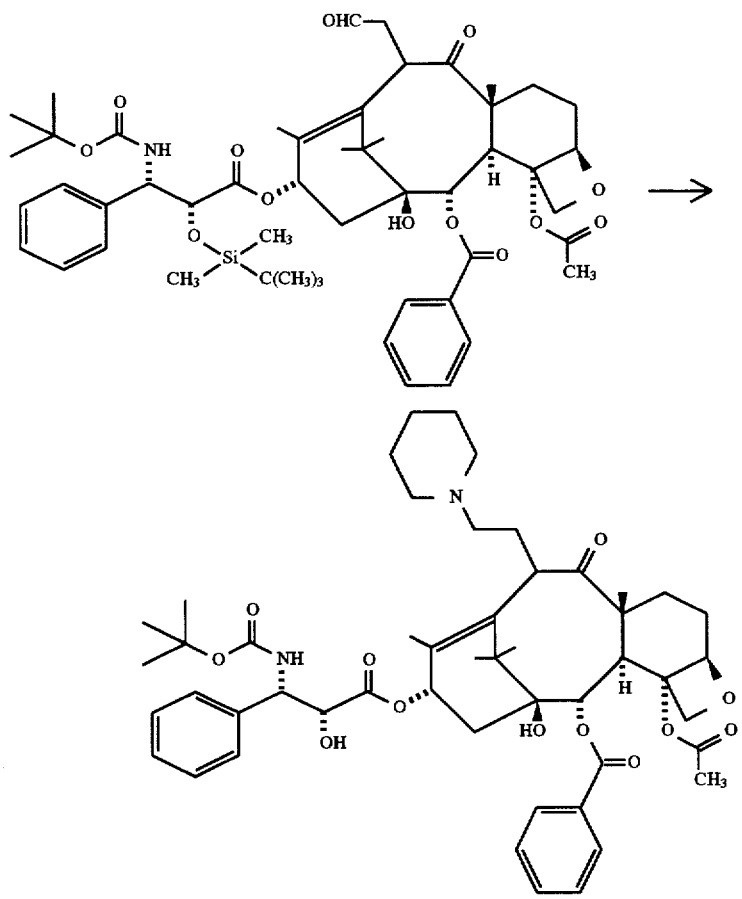

13-O-[(2R,3S)-3-(tert-Butoxycarbonylamino)-2-hydroxy-3-phenylpropionyl]-10-deacetoxy-7-deoxy-10-(2-piperidinoethyl)baccatin III The compound obtained in Step 8 of Example 37 was reacted in the same manner as in Step 1 of Example 19 except for using piperidine in place of dimethylamine, followed by purification. The resulting compound was reacted in the same manner as in Step 5 of Example 16, followed by purification to yield the titled compound.

$^1$H-NMR (CDCl$_3$/TMS) δ(ppm): 1.09(3H, s), 1.20(3H, s), 1.31(9H, s), 1.3–1.8(8H, m), 1.70(3H, s), 1.79(3H, s), 1.8–2.6(12H, m), 2.39(3H, s), 3.91(1H, d, J=7 Hz), 4.03(1H, br-t, J=6 Hz), 4.24(1H, d, J=8 Hz), 4.31(1H, d, J=8 Hz), 4.60(1H, br-s), 4.95(1H, dd, J=3 Hz, 10 Hz), 5.28(1H, br-d, J=10 Hz), 5.39(1H, d, J=10 Hz), 5.64(1H, d, J=7 Hz), 6.19(1H, t, J=8 Hz), 7.31(1H, br-t, J=7 Hz), 7.35–7.45(4H, m), 7.50(2H, t, J=7 Hz), 7.60(1H, t, J=7 Hz), 8.13(2H, d, J=7 Hz).

[EFFECTS OF THE INVENTION]

The antitumor effect of the compounds of the present invention is shown in the following test example.

TEST EXAMPLE

Each of three tumor cells, P388, PC-6 and PC-12, were inoculated in a 96-well microplate in amounts of 5.0×10$^2$ cells/150 μl/well of P388, 5.0×10$^3$ cells/150 μl/well of PC-6, and 1.0×10$^3$ cells/150 μl/well of PC-12, and after 2 hours in the case of P388 or after 24 hours in the cases of PC-6 and PC-12, test compound was added to the well in an amount of 50 μl/well in each case. Cells were cultivated for 3 days. Then, a 5 mg/ml solution of MTT [3-(4,5-dimethylthiazol-2-yl)-2,5-diphenyl-2H-tetrazolium bromide] was added to the well in an amount of 20 μl/well. After 4 hours, the culture liquid was removed, dimethylsulfoxide was added to the well in an amount of 150 μl/well, and the absorbance at 540 nm was measured. The antitumor effect was determined in terms of a concentration of the test compound required for suppressing the cell growth in the medicated group to 50% of the cell growth in the control group, i.e., a GI$_{50}$ value (ng/ml).

The results obtained are shown in Table 1 below.

TABLE 1

| Test Compound | GI$_{50}$ Value (ng/ml) | | |
|---|---|---|---|
| | P388 | PC-6 | PC-12 |
| Taxol | 30.4 | 3.51 | 136 |
| Taxotel | 5.30 | 1.72 | 49.7 |
| Example 7 | 3.30 | 0.771 | 24.4 |
| Example 16 | 1.16 | 0.677 | 7.87 |
| Example 18 | 1.19 | 0.983 | 12.9 |
| Example 20 | 3.07 | 0.603 | 13.5 |

TABLE 1-continued

| Test Compound | GI$_{50}$ Value (ng/ml) | | |
|---|---|---|---|
| | P388 | PC-6 | PC-12 |
| Example 24 | 0.845 | 1.67 | 4.99 |
| Example 25 | 0.226 | 0.771 | 1.34 |
| Example 26 | 1.07 | 1.22 | 5.64 |
| Example 31 | 0.136 | 1.03 | 1.26 |
| Example 33 Isomer B | 0.690 | 4.13 | 4.16 |
| Example 35 | 0.729 | 1.83 | 2.95 |
| Example 36 | 0.505 | 1.64 | 1.81 |

We claim:

1. A compound represented by the general formula (I)

wherein

R$^1$ represents an alkyl group, an alkenyl group or an alkynyl group, in which said alkyl, alkenyl and alkynyl groups may have one or more substituents selected from the group consisting of a carboxyl group, an alkoxyl group, an aryloxy group, an alkoxycarbonyl group, an aryloxycarbonyl group, a cyano group, a hydroxy group, an amino group, an alkylamino group, an acyl group, an acylamino group, an acyloxy group, an alkoxycarbonylamino group, an alkylthio group, an alkylsulfinyl group, an alkylsulfonyl group and a saturated or unsaturated 3- to 8-membered nitrogen containing heterocyclic group represented by the formula:

wherein X represents an oxygen atom, a sulfur atom, CH$_2$, CH—Y, NH or N—Y, in which Y represents an alkyl group, and said heterocyclic group may have one or more alkyl groups on the carbon atom which is a constituent atom of the ring;

R$^2$ represents a hydrogen atom, a hydroxy group, a halogen atom or an alkyl group;

R$^3$ represents a hydrogen atom, a hydroxy group, a halogen atom or an alkyl group;

R$^4$ represents an alkyl group, an alkenyl group, an alkynyl group, a cycloalkyl group, an aryl group or a heterocyclic group, in which said alkyl, alkenyl, alkynyl, cycloalkyl, aryl and heterocyclic groups may have one or more substituents selected from the group consisting of a halogen atom, a hydroxy group, a carboxyl group, an alkyl group, an alkoxyl group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group;

R$^5$ represents an alkyl group, an aryl group or an alkoxyl group, in which said alkyl, aryl and alkoxyl groups may have one or more substituents selected from the group consisting of a halogen atom, a hydroxy group, a carboxyl group, an alkyl group, an alkoxyl group, a phenyl group, an amino group, an alkylamino group, an aminoalkyl group, an alkylaminoalkyl group, an alkoxycarbonyl group, an aryloxycarbonyl group, an acyl group, an acylamino group and an acyloxy group;

R$^6$ represents a hydrogen atom or a hydroxy group;

R represents an alkyl group, an alkyl group having one or more substituents, an alkenyl group, an alkenyl group having one or more substituents, an alkynyl group, an alkynyl group having one or more substituents, an alkoxyl group, or an alkoxyl group having one or more substituents, a cycloalkyl group or a cycloalkyl group having one or more substituents, in which said substituent is selected from the group consisting of a halogen atom, a hydroxy group, a carboxyl group, an alkoxyl group, an aryloxy group, a phenyl group, an amino group, an alkylamino group, an alkoxycarbonyl group, an aryloxycarbonyl group, an acyl group, an acylamino group and an acyloxy group; and Z represents a phenyl group which may be substituted by one or more halogen atoms, alkyl groups or alkoxyl groups; and a salt thereof.

2. A compound or a salt thereof as claimed in claim 1, wherein R$^1$ and R$^2$ are fluorine atoms.

3. A compound or a salt thereof as claimed in claim 1, wherein R$^2$ is a hydroxy group, and R$^3$ is a hydrogen atom.

4. A compound or a salt thereof as claimed in claim 1, wherein R$^2$ is a hydroxy group, and R$^3$ is a methyl group.

5. A compound or a salt thereof as claimed in any of claims 1 to 4, wherein R$^5$ is a phenyl group.

6. A compound or a salt thereof as claimed in any of claims 1 to 4, wherein R$^5$ is a tertiary butoxy group.

7. A compound or a salt thereof as claimed in claim 1, wherein R$^4$ is a 2-methyl-1-propenyl group.

8. A compound or a salt thereof as claimed in claim 1, wherein R$^4$ is a phenyl group.

9. A compound or a salt thereof as claimed in claim 1, wherein R$^4$ is a heterocyclic group.

10. A compound or a salt thereof as claimed in claim 9, wherein the heterocyclic group is a monocyclic heterocyclic group.

11. A compound or a salt thereof as claimed in claim 9, wherein the heterocyclic group is a monocyclic 5- or 6-membered heterocyclic group.

12. A compound or a salt thereof as claimed in claim 9, wherein the heterocyclic group is a monocyclic 5- or 6-membered heterocyclic group containing one of an oxygen atom, a nitrogen atom and a sulfur atom as a constituent atom of the ring structure thereof.

13. A compound or a salt thereof as claimed in claim 9, wherein the heterocyclic group is a monocyclic unsaturated 5-membered or 6-membered heterocyclic group containing one of an oxygen atom, a nitrogen atom or a sulfur atom as a constituent atom of the ring structure thereof.

14. A compound or a salt thereof as claimed in claim 1, wherein R$^4$ is a furyl group, a pyrrolyl group or a pyridyl group.

15. A compound or a salt thereof as claimed in claim 1, wherein R$^1$ is an alkyl group or an alkenyl group each having a substituent.

16. A compound or a salt thereof as claimed in claim 1, wherein R$^1$ is an alkyl group having from 1 to 6 carbon atoms and having, as a substituent, an alkoxycarbonyl group, a hydroxy group, a cyano group, an acyl group, an alkylamino group, an alkylthio group or a saturated 5- or 6-membered heterocyclic group containing a nitrogen atom represented by the formula:

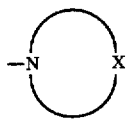

wherein X represents an oxygen atom, a sulfur atom, CH$_2$, CH—Y, NH or N—Y, in which Y represents an alkyl group, and said heterocyclic ring may have one or more alkyl groups on the carbon atom which is a constituent atom of the ring thereof; or an alkenyl group having from 2 to 6 carbon atoms.

17. A compound or a salt thereof as claimed in claim 1, wherein R$^1$ is an alkyl group having 1 to 6 carbon atoms and having, as a substituent, a saturated 5-membered or 6-membered heterocyclic group containing a nitrogen atom represented by the formula:

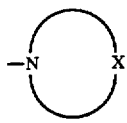

wherein X represents an oxygen atom, a sulfur atom, CH$_2$, CH—Y, NH or N—Y, in which Y represents an alkyl group, and said heterocyclic ring may have one or a plurality of an alkyl group on the carbon atom which is a constituent atom of the ring thereof; or an allyl group.

18. A compound or a salt thereof as claimed in claim 1, wherein R$^1$ is an alkyl group having 1 to 4 carbon atoms, and having as a substituent, a morpholino group or a thiomorpholino group; or an allyl group.

19. A compound or a salt thereof as claimed in claim 1, wherein R is an alkyl group having 1 to 8 carbon atoms, an alkoxyl group having 1 to 6 carbon atoms and a cycloalkyl group having 3 to 6 carbon atoms.

20. A compound or a salt thereof as claimed in claim 1, wherein R is a methyl group, an ethyl group, a propyl group, a methoxy group, an ethoxy group or a cyclopropyl group.

21. A compound or a salt thereof as claimed in claim 1, wherein R$^1$ is an alkyl group having 2 or 3 carbon atoms and having a morpholino group or a thiomorpholino group, in which said morpholino group or said thiomorpholino group may have one or more methyl groups on the carbon atom which is a constituent atom of the ring thereof, R$^2$ is a hydroxy group, R$^3$ is a hydrogen atom, R$^4$ is a furyl group or a phenyl group, R$^5$ is a tertiary butoxy group, and R is a methyl group, an ethyl group or a propyl group.

22. A compound or a salt thereof as claimed in claim 1, which has a steric configuration represented by the formula (Ia).

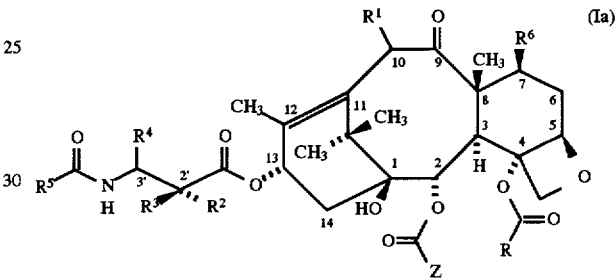

* * * * *